US009248450B2

(12) United States Patent
Bauer

(10) Patent No.: US 9,248,450 B2
(45) Date of Patent: Feb. 2, 2016

(54) DROPLET OPERATIONS PLATFORM

(75) Inventor: William Craig Bauer, Raleigh, NC (US)

(73) Assignee: ADVANCED LIQUID LOGIC, INC., San Diego, CA (US)

(*) Notice: Subject to any disclaimer, the term of this patent is extended or adjusted under 35 U.S.C. 154(b) by 63 days.

(21) Appl. No.: 13/638,324

(22) PCT Filed: Mar. 30, 2011

(86) PCT No.: PCT/US2011/030543
§ 371 (c)(1),
(2), (4) Date: Jan. 22, 2013

(87) PCT Pub. No.: WO2011/126892
PCT Pub. Date: Oct. 13, 2011

(65) Prior Publication Data
US 2013/0217103 A1 Aug. 22, 2013

Related U.S. Application Data

(60) Provisional application No. 61/361,576, filed on Jul. 6, 2010, provisional application No. 61/318,851, filed on Mar. 30, 2010.

(51) Int. Cl.
B01L 7/00 (2006.01)
B01F 13/00 (2006.01)
B01L 3/00 (2006.01)

(52) U.S. Cl.
CPC ............ B01L 7/525 (2013.01); B01F 13/0071 (2013.01); B01F 13/0076 (2013.01);
(Continued)

(58) Field of Classification Search
CPC ............. B01L 7/525; B01L 2400/424; B01L 2400/427

USPC ......... 422/408, 412, 428, 502, 504, 509, 518, 422/105, 106; 204/408, 600–602, 607–608
See application file for complete search history.

(56) References Cited

U.S. PATENT DOCUMENTS 4,636,785 A 1/1987 Le Pesant
5,181,016 A 1/1993 Lee et al.
(Continued)

FOREIGN PATENT DOCUMENTS

JP 2006329899 A 12/2006
JP 2006329904 A 12/2006
(Continued)

OTHER PUBLICATIONS

Benton et al., "Library Preparation Method 1 DNA Library Construction for Illumina SBS Sequencing Platforms using NEBNext® Library Preparation Reagents", Application Note, NuGEN, 2011.
(Continued)

Primary Examiner — Brian R Gordon
(74) Attorney, Agent, or Firm — William A. Barrett; Ward & Smith, P.A.; Ryan K. Simmons

(57) ABSTRACT

The invention relates to a droplet actuator device and methods for integrated sample preparation and analysis of a biological sample. A droplet actuator device is provided for conducting droplet operations. The droplet actuator device may include a bottom substrate and a top substrate separated from each other to form a gap therebetween; an arrangement of droplet operations electrodes arranged on one or both of the bottom and/or top substrates for conducting droplet operations thereon; a reagent storage layer comprising one or more compartments bound to the top substrate; and one or more openings arranged to provide a fluidic path from the one or more compartments into the gap, upon breach of a breachable seal separating the one or more compartments and openings.

22 Claims, 30 Drawing Sheets

(52) U.S. Cl.
CPC .... *B01L 3/502784* (2013.01); *B01L 3/502707* (2013.01); *B01L 3/502715* (2013.01); *B01L 3/502761* (2013.01); *B01L 7/54* (2013.01); *B01L 2200/027* (2013.01); *B01L 2200/0668* (2013.01); *B01L 2200/16* (2013.01); *B01L 2300/1805* (2013.01); *B01L 2300/1827* (2013.01); *B01L 2400/043* (2013.01); *B01L 2400/0427* (2013.01); *B01L 2400/0677* (2013.01); *B01L 2400/0683* (2013.01)

(56) References Cited

U.S. PATENT DOCUMENTS

| | | | |
|---|---|---|---|
| 5,486,337 A | 1/1996 | Ohkawa et al. | |
| 6,063,339 A | 5/2000 | Tisone et al. | |
| 6,130,098 A | 10/2000 | Handique et al. | |
| 6,294,063 B1 | 9/2001 | Becker et al. | |
| 6,565,727 B1 | 5/2003 | Shenderov | |
| 6,773,566 B2 | 8/2004 | Shenderov | |
| 6,790,011 B1 | 9/2004 | Le Pesant et al. | |
| 6,911,132 B2 | 6/2005 | Pamula et al. | |
| 6,924,792 B1 | 8/2005 | Jessop | |
| 6,977,033 B2 | 12/2005 | Becker et al. | |
| 6,989,234 B2 | 1/2006 | Kolar et al. | |
| 7,052,244 B2 | 5/2006 | Fouillet et al. | |
| 7,068,367 B2 | 6/2006 | Stobrawa | |
| 7,163,612 B2 | 1/2007 | Sterling et al. | |
| 7,211,223 B2 | 5/2007 | Fouillet et al. | |
| 7,255,780 B2 | 8/2007 | Shenderov | |
| 7,328,979 B2 | 2/2008 | Decre et al. | |
| 7,329,545 B2 | 2/2008 | Pamula et al. | |
| 7,439,014 B2 | 10/2008 | Pamula et al. | |
| 7,458,661 B2 | 12/2008 | Kim et al. | |
| 7,531,072 B2 | 5/2009 | Roux et al. | |
| 7,547,380 B2 | 6/2009 | Velev | |
| 7,569,129 B2 | 8/2009 | Pamula et al. | |
| 7,641,779 B2 | 1/2010 | Becker et al. | |
| 7,727,466 B2 | 6/2010 | Meathrel et al. | |
| 7,727,723 B2 | 6/2010 | Pollack et al. | |
| 7,759,132 B2 | 7/2010 | Pollack et al. | |
| 7,763,471 B2 | 7/2010 | Pamula et al. | |
| 7,815,871 B2* | 10/2010 | Pamula et al. | 422/404 |
| 7,816,121 B2* | 10/2010 | Pollack et al. | 435/286.5 |
| 7,822,510 B2 | 10/2010 | Paik et al. | |
| 7,851,184 B2 | 12/2010 | Pollack et al. | |
| 7,875,160 B2 | 1/2011 | Jary | |
| 7,901,947 B2* | 3/2011 | Pollack et al. | 436/180 |
| 7,919,330 B2 | 4/2011 | De Guzman et al. | |
| 7,922,886 B2 | 4/2011 | Fouillet et al. | |
| 7,939,021 B2 | 5/2011 | Smith et al. | |
| 7,943,030 B2 | 5/2011 | Shenderov | |
| 7,989,056 B2 | 8/2011 | Plissonier et al. | |
| 7,998,436 B2* | 8/2011 | Pollack et al. | 422/509 |
| 8,007,739 B2* | 8/2011 | Pollack et al. | 422/509 |
| 8,041,463 B2 | 10/2011 | Pollack et al. | |
| 8,048,628 B2 | 11/2011 | Pollack et al. | |
| 8,075,754 B2 | 12/2011 | Sauter-Starace et al. | |
| 8,088,578 B2* | 1/2012 | Hua et al. | 435/6.1 |
| 8,093,062 B2 | 1/2012 | Winger et al. | |
| 8,093,064 B2 | 1/2012 | Shah et al. | |
| 8,137,917 B2 | 3/2012 | Pollack et al. | |
| 8,147,668 B2 | 4/2012 | Pollack et al. | |
| 8,202,686 B2 | 6/2012 | Pamula et al. | |
| 8,208,146 B2 | 6/2012 | Srinivasan et al. | |
| 8,221,605 B2 | 7/2012 | Pollack et al. | |
| 8,236,156 B2 | 8/2012 | Sarrut et al. | |
| 8,268,246 B2 | 9/2012 | Srinivasan et al. | |
| 8,287,711 B2 | 10/2012 | Pollack et al. | |
| 8,304,253 B2 | 11/2012 | Yi et al. | |
| 8,313,698 B2* | 11/2012 | Pollack et al. | 422/82.05 |
| 8,317,990 B2 | 11/2012 | Pamula et al. | |
| 8,342,207 B2 | 1/2013 | Raccurt et al. | |
| 8,349,276 B2* | 1/2013 | Pamula et al. | 422/504 |
| 8,364,315 B2 | 1/2013 | Sturmer et al. | |
| 8,388,909 B2* | 3/2013 | Pollack et al. | 422/504 |
| 8,389,297 B2 | 3/2013 | Pamula et al. | |
| 8,394,249 B2 | 3/2013 | Pollack et al. | |
| 8,394,641 B2 | 3/2013 | Winger | |
| 8,426,213 B2 | 4/2013 | Eckhardt et al. | |
| 8,440,392 B2 | 5/2013 | Pamula et al. | |
| 8,444,836 B2 | 5/2013 | Fouillet et al. | |
| 8,658,111 B2* | 2/2014 | Srinivasan et al. | 422/502 |
| 2002/0005354 A1 | 1/2002 | Spence et al. | |
| 2002/0036139 A1 | 3/2002 | Becker et al. | |
| 2002/0043463 A1 | 4/2002 | Shenderov | |
| 2002/0058332 A1 | 5/2002 | Quake et al. | |
| 2002/0143437 A1 | 10/2002 | Handique et al. | |
| 2003/0164295 A1 | 9/2003 | Sterling | |
| 2003/0183525 A1 | 10/2003 | Elrod et al. | |
| 2003/0205632 A1 | 11/2003 | Kim et al. | |
| 2004/0031688 A1 | 2/2004 | Shenderov | |
| 2004/0055891 A1 | 3/2004 | Pamula et al. | |
| 2004/0058450 A1 | 3/2004 | Pamula et al. | |
| 2004/0231987 A1 | 11/2004 | Sterling et al. | |
| 2006/0021875 A1 | 2/2006 | Griffith et al. | |
| 2006/0054503 A1 | 3/2006 | Pamula et al. | |
| 2006/0164490 A1 | 7/2006 | Kim et al. | |
| 2006/0194331 A1 | 8/2006 | Pamula et al. | |
| 2006/0231398 A1 | 10/2006 | Sarrut et al. | |
| 2007/0023292 A1 | 2/2007 | Kim et al. | |
| 2007/0037294 A1 | 2/2007 | Pamula et al. | |
| 2007/0045117 A1 | 3/2007 | Pamula et al. | |
| 2007/0064990 A1 | 3/2007 | Roth | |
| 2007/0086927 A1 | 4/2007 | Natarajan et al. | |
| 2007/0207513 A1 | 9/2007 | Sorensen et al. | |
| 2007/0217956 A1 | 9/2007 | Pamula et al. | |
| 2007/0241068 A1 | 10/2007 | Pamula et al. | |
| 2007/0242105 A1 | 10/2007 | Srinivasan et al. | |
| 2007/0242111 A1 | 10/2007 | Pamula et al. | |
| 2007/0243634 A1 | 10/2007 | Pamula et al. | |
| 2007/0267294 A1 | 11/2007 | Shenderov | |
| 2007/0275415 A1 | 11/2007 | Srinivasan et al. | |
| 2008/0006535 A1 | 1/2008 | Paik et al. | |
| 2008/0038810 A1 | 2/2008 | Pollack et al. | |
| 2008/0044893 A1 | 2/2008 | Pollack et al. | |
| 2008/0044914 A1 | 2/2008 | Pamula et al. | |
| 2008/0050834 A1 | 2/2008 | Pamula et al. | |
| 2008/0053205 A1* | 3/2008 | Pollack et al. | 73/61.71 |
| 2008/0105549 A1 | 5/2008 | Pamela et al. | |
| 2008/0124252 A1 | 5/2008 | Marchand et al. | |
| 2008/0142376 A1 | 6/2008 | Fouillet et al. | |
| 2008/0151240 A1 | 6/2008 | Roth | |
| 2008/0210558 A1 | 9/2008 | Sauter-Starace et al. | |
| 2008/0230386 A1* | 9/2008 | Srinivasan et al. | 204/450 |
| 2008/0247920 A1 | 10/2008 | Pollack et al. | |
| 2008/0264797 A1 | 10/2008 | Pamula et al. | |
| 2008/0274513 A1 | 11/2008 | Shenderov et al. | |
| 2008/0281471 A1 | 11/2008 | Smith et al. | |
| 2008/0283414 A1 | 11/2008 | Monroe et al. | |
| 2008/0302431 A1 | 12/2008 | Marchand et al. | |
| 2008/0305481 A1 | 12/2008 | Whitman et al. | |
| 2009/0014394 A1 | 1/2009 | Yi et al. | |
| 2009/0042319 A1 | 2/2009 | De Guzman et al. | |
| 2009/0127123 A1 | 5/2009 | Raccurt et al. | |
| 2009/0134027 A1 | 5/2009 | Jary | |
| 2009/0142564 A1 | 6/2009 | Plissonnier et al. | |
| 2009/0155902 A1 | 6/2009 | Pollack et al. | |
| 2009/0192044 A1 | 7/2009 | Fouillet | |
| 2009/0260988 A1 | 10/2009 | Pamula et al. | |
| 2009/0263834 A1 | 10/2009 | Sista et al. | |
| 2009/0280251 A1 | 11/2009 | De Guzman et al. | |
| 2009/0280475 A1 | 11/2009 | Pollack et al. | |
| 2009/0280476 A1 | 11/2009 | Srinivasan et al. | |
| 2009/0283407 A1 | 11/2009 | Shah et al. | |
| 2009/0288710 A1 | 11/2009 | Viovy et al. | |
| 2009/0291433 A1 | 11/2009 | Pollack et al. | |
| 2009/0304944 A1 | 12/2009 | Sudarsan et al. | |
| 2009/0311713 A1 | 12/2009 | Pollack et al. | |
| 2009/0321262 A1 | 12/2009 | Adachi et al. | |
| 2010/0025242 A1* | 2/2010 | Pamula et al. | 204/450 |
| 2010/0025250 A1 | 2/2010 | Pamula et al. | |
| 2010/0028920 A1 | 2/2010 | Eckhardt | |
| 2010/0032293 A1 | 2/2010 | Pollack et al. | |
| 2010/0041086 A1 | 2/2010 | Pamula et al. | |

(56) References Cited

U.S. PATENT DOCUMENTS

| | | |
|---|---|---|
| 2010/0048410 A1 | 2/2010 | Shenderov et al. |
| 2010/0062508 A1 | 3/2010 | Pamula et al. |
| 2010/0068764 A1 | 3/2010 | Sista et al. |
| 2010/0087012 A1 | 4/2010 | Shenderov et al. |
| 2010/0096266 A1 | 4/2010 | Kim et al. |
| 2010/0116640 A1* | 5/2010 | Pamula et al. ............ 204/156 |
| 2010/0118307 A1 | 5/2010 | Srinivasan et al. |
| 2010/0120130 A1* | 5/2010 | Srinivasan et al. ........ 435/283.1 |
| 2010/0126860 A1 | 5/2010 | Srinivasan et al. |
| 2010/0130369 A1 | 5/2010 | Shenderov et al. |
| 2010/0140093 A1* | 6/2010 | Pamula et al. ............ 204/547 |
| 2010/0143963 A1 | 6/2010 | Pollack |
| 2010/0151439 A1 | 6/2010 | Pamula et al. |
| 2010/0190263 A1 | 7/2010 | Srinivasan et al. |
| 2010/0194408 A1 | 8/2010 | Sturmer et al. |
| 2010/0221713 A1 | 9/2010 | Pollack et al. |
| 2010/0236927 A1 | 9/2010 | Pope et al. |
| 2010/0236928 A1 | 9/2010 | Srinivasan et al. |
| 2010/0236929 A1 | 9/2010 | Pollack et al. |
| 2010/0258441 A1 | 10/2010 | Sista et al. |
| 2010/0270156 A1 | 10/2010 | Srinivasan et al. |
| 2010/0279374 A1 | 11/2010 | Sista et al. |
| 2010/0282608 A1 | 11/2010 | Srinivasan et al. |
| 2010/0282609 A1 | 11/2010 | Pollack et al. |
| 2010/0307917 A1 | 12/2010 | Srinivasan et al. |
| 2010/0320088 A1 | 12/2010 | Fouillet et al. |
| 2010/0323405 A1 | 12/2010 | Pollack et al. |
| 2011/0076692 A1 | 3/2011 | Sista et al. |
| 2011/0086377 A1 | 4/2011 | Thwar et al. |
| 2011/0091989 A1 | 4/2011 | Sista et al. |
| 2011/0097763 A1 | 4/2011 | Pollack et al. |
| 2011/0100823 A1* | 5/2011 | Pollack et al. ............ 204/601 |
| 2011/0104725 A1 | 5/2011 | Pamula et al. |
| 2011/0104747 A1 | 5/2011 | Pollack et al. |
| 2011/0104816 A1 | 5/2011 | Pollack et al. |
| 2011/0114490 A1 | 5/2011 | Pamula et al. |
| 2011/0118132 A1 | 5/2011 | Winger et al. |
| 2011/0147215 A1 | 6/2011 | Fuchs et al. |
| 2011/0180571 A1 | 7/2011 | Srinivasan et al. |
| 2011/0186433 A1* | 8/2011 | Pollack et al. ............ 204/549 |
| 2011/0203930 A1 | 8/2011 | Pamula et al. |
| 2011/0209998 A1 | 9/2011 | Shenderov |
| 2011/0213499 A1 | 9/2011 | Sturmer et al. |
| 2011/0303542 A1 | 12/2011 | Srinivasan et al. |
| 2011/0311980 A1 | 12/2011 | Pollack et al. |
| 2012/0018306 A1* | 1/2012 | Srinivasan et al. ........ 204/547 |
| 2012/0044299 A1 | 2/2012 | Winger |
| 2012/0132528 A1 | 5/2012 | Shenderov et al. |
| 2012/0136147 A1 | 5/2012 | Winger |
| 2012/0165238 A1* | 6/2012 | Pamula et al. ............ 510/244 |
| 2012/0261264 A1* | 10/2012 | Srinivasan et al. ........ 204/643 |
| 2013/0059366 A1 | 3/2013 | Pollack et al. |
| 2013/0092539 A1* | 4/2013 | Pollack et al. ............ 204/452 |
| 2013/0118901 A1* | 5/2013 | Pollack et al. ............ 204/451 |

FOREIGN PATENT DOCUMENTS

| | | |
|---|---|---|
| WO | 0069565 A1 | 11/2000 |
| WO | 0073655 A1 | 12/2000 |
| WO | 2004029585 A1 | 4/2004 |
| WO | 2004030820 | 4/2004 |
| WO | 2004030820 A2 | 4/2004 |
| WO | 2005047696 A1 | 5/2005 |
| WO | 2006013303 A1 | 2/2006 |
| WO | 2006070162 A1 | 7/2006 |
| WO | 2006081558 | 8/2006 |
| WO | 2006124458 A2 | 11/2006 |
| WO | 2006127451 A2 | 11/2006 |
| WO | 2006134307 A1 | 12/2006 |
| WO | 2006138543 | 12/2006 |
| WO | 2007003720 A1 | 1/2007 |
| WO | 2007012638 A1 | 2/2007 |
| WO | 2007033990 A1 | 3/2007 |
| WO | 2007048111 | 4/2007 |
| WO | 2007120240 A2 | 10/2007 |
| WO | 2007120241 A2 | 10/2007 |
| WO | 2007123908 A2 | 11/2007 |
| WO | 2008051310 A2 | 5/2008 |
| WO | 2008055256 A3 | 5/2008 |
| WO | 2008068229 A1 | 6/2008 |
| WO | 2008091848 A2 | 7/2008 |
| WO | 2008098236 A2 | 8/2008 |
| WO | 2008101194 A2 | 8/2008 |
| WO | 2008106678 A1 | 9/2008 |
| WO | 2008109664 A1 | 9/2008 |
| WO | 2008112856 A1 | 9/2008 |
| WO | 2008116209 A1 | 9/2008 |
| WO | 2008116221 A1 | 9/2008 |
| WO | 2008118831 A2 | 10/2008 |
| WO | 2008124846 A2 | 10/2008 |
| WO | 2008131420 A2 | 10/2008 |
| WO | 2008134153 A1 | 11/2008 |
| WO | 2009002920 A1 | 12/2008 |
| WO | 2009003184 A1 | 12/2008 |
| WO | 2009011952 A1 | 1/2009 |
| WO | 2009021173 A1 | 2/2009 |
| WO | 2009021233 A2 | 2/2009 |
| WO | 2009026339 A2 | 2/2009 |
| WO | 2009029561 A2 | 3/2009 |
| WO | 2009032863 A2 | 3/2009 |
| WO | 2009052095 A1 | 4/2009 |
| WO | 2009052123 A2 | 4/2009 |
| WO | 2009052321 A2 | 4/2009 |
| WO | 2009052345 A1 | 4/2009 |
| WO | 2009052348 A2 | 4/2009 |
| WO | 2009076414 | 6/2009 |
| WO | 2009076414 A1 | 6/2009 |
| WO | 2009086403 A2 | 7/2009 |
| WO | 2009111769 A2 | 9/2009 |
| WO | 2009135205 A2 | 11/2009 |
| WO | 2009137415 A2 | 11/2009 |
| WO | 2009140373 A2 | 11/2009 |
| WO | 2009140671 A2 | 11/2009 |
| WO | 2010004014 A1 | 1/2010 |
| WO | 2010006166 A2 | 1/2010 |
| WO | 2010009463 A2 | 1/2010 |
| WO | 2010019782 A2 | 2/2010 |
| WO | 2010027894 A2 | 3/2010 |
| WO | 2010042637 A2 | 4/2010 |
| WO | 2010077859 A3 | 7/2010 |
| WO | 2011002957 A2 | 1/2011 |
| WO | 2011020011 A2 | 2/2011 |
| WO | 2011057197 A2 | 5/2011 |
| WO | 2011084703 A2 | 7/2011 |
| WO | 2011126892 A2 | 10/2011 |
| WO | 2012009320 A2 | 1/2012 |
| WO | 2012012090 A2 | 1/2012 |
| WO | 2012037308 A2 | 3/2012 |
| WO | 2012068055 A3 | 5/2012 |

OTHER PUBLICATIONS

Bottausci et al., "Fully Integrated EWOD Based Bio-Analysis Device", Labautomation 2011, Palm Springs Convention Center, Palm Springs, CA, USA; Abstract in Proceedings on line, poster distributed, Jan. 29-Feb. 2, 2011.

Burton et al., "Diagnosis of Fabry and Gaucher diseases from the Pilot Screening of Newborns for Lysosomal Storage Disorders in Illinois", APHL Newborn Screening and Genetic Testing Symposium, San Diego, 2011.

Chakrabarty, "Automated Design of Microfluidics-Based Biochips: connecting Biochemistry of Electronics CAD", IEEE International Conference on Computer Design, San Jose, CA, Oct. 1-4, 2006, 93-100.

Chakrabarty et al., "Design Automation Challenges for Microfluidics-Based Biochips", DTIP of MEMS & MOEMS, Montreux, Switzerland, Jun. 1-3, 2005.

Chakrabarty et al., "Design Automation for Microfluidics-Based Biochips", ACM Journal on Engineering Technologies in Computing Systems , 1(3), Oct. 2005, 186-223.

(56) References Cited

OTHER PUBLICATIONS

Chakrabarty, "Design, Testing, and Applications of Digital Microfluidics-Based Biochips", Proceedings of the 18th International Conf. on VLSI held jointly with 4th International Conf. on Embedded Systems Design (VLSID'05), IEEE, Jan. 3-7, 2005.

Chen et al., "Development of Mesoscale Actuator Device with Micro Interlocking Mechanism", J. Intelligent Material Systems and Structures, vol. 9, No. 4, Jun. 1998, pp. 449-457.

Chen et al., "Mesoscale Actuator Device with Micro Interlocking Mechanism", Proc. IEEE Micro Electro Mechanical Systems Workshop, Heidelberg, Germany, Jan. 1998, pp. 384-389.

Chen et al., "Mesoscale Actuator Device: Micro Interlocking Mechanism to Transfer Macro Load", Sensors and Actuators, vol. 73, Issues 1-2, Mar. 1999, pp. 30-36.

Cotten et al., "Digital Microfluidics: a novel platform for multiplexed detection of lysosomal storage diseases", Abstract # 3747.9. Pediatric Academic Society Conference, 2008.

Delapierre et al., "SmartDrop: An Integrated System from Sample Collection to Result using real-time PCR," 4th National Bio-Threat Conference, Dec. 7-9, 2010, New Orleans, LA, USA; Abstract in Proceedings, Poster presented at conference.

Delattre, Movie in news on TF1 (at 12'45" Cyril Delattre), http://videos.tf1.fr/jt-we/zoom-sur-grenoble-6071525.html, 2009.

Delattre, Movie in talk show "C Dans l'air" (at 24" Cyril Delattre), http://www.france5.fr/c-dans-l-air/sante/bientot-vous-ne-serez-plus-malade-31721, 2009.

Delattre, Movie on Web TV—Cite des sciences (at 3'26" Cyril Delattre), http://www.universcience.tv/video-laboratoire-de-poche-793.html, 2009.

Delattre et al., "SmartDrop: an integrated system from sample preparation to analysis using real-time PCR", 10th International Symposium on Protection against Chemical and Biological Warfare Agents; Stockholm, Sweden; poster, Jun. 10, 2010.

Delattre et al., "SmartDrop: An integrated system from sample preparation to analysis using real-time PCR", 10th International Symposium on Protection against Chemical and Biological Warfare Agents; Stockholm, Sweden; Abstract,paper,, Jun. 8-11, 2010.

Delattre et al., "Towards an industrial fabrication process for electrowetting chip using standard MEMS Technology", μTAS2008, San Diego; poster presented, Oct. 15, 2008.

Delattre et al., "Towards an industrial fabrication process for electrowetting chip using standard MEMS Technology", μTAS2008, San Diego; Abstract in proceedings, Oct. 13-16, 2008, 1696-1698.

Dewey, "Towards a Visual Modeling Approach to Designing Microelectromechanical System Transducers", Journal of Micromechanics and Microengineering, vol. 9, Dec. 1999, 332-340.

Dewey et al., "Visual modeling and design of microelectromechanical system tansducers", Microelectronics Journal, vol. 32, Apr. 2001, 373-381.

Eckhardt et al., "Development and validation of a single-step fluorometric assay for Hunter syndrome", APHL Newborn Screening and Genetic Testing Symposium, San Diego, 2011.

Emani et al., "Novel Microfluidic Platform for Point of Care Hypercoagulability Panel Testing", Circulation, vol. 122, 2010, A14693.

Fair et al., "A Micro- Watt Metal-Insulator-Solution-Transport (MIST) Device for Scalable Digital Bio-Microfluidic Systems", IEEE IEDM Technical Digest, 2001, 16.4.1-4.

Fair et al., "Advances in droplet-based bio lab-on-a-chip", BioChips 2003, Boston, 2003.

Fair et al., "Bead-Based and Solution-Based Assays Performed on a Digital Microfluidic Platform", Biomedical Engineering Society (BMES) Fall Meeting, Baltimore, MD, Oct. 1, 2005.

Fair, "Biomedical Applications of Electrowetting Systems", 5th International Electrowetting Workshop, Rochester, NY, May 31, 2006.

Fair et al., "Chemical and Biological Applications of Digital-Microfluidic Devices", IEEE Design & Test of Computers, vol. 24(1), Jan.-Feb. 2007, 10-24.

Fair et al., "Chemical and biological pathogen detection in a digital microfluidic platform", DARPA Workshop on Microfluidic Analyzers for DoD and National Security Applications, Keystone, CO, 2006.

Fair, "Digital microfluidics: is a true lab-on-a-chip possible?", Microfluid Nanofluid, vol. 3, Mar. 8, 2007, 245-281.

Fair, "Droplet-based microfluidic Genome sequencing", NHGRI PI's meeting, Boston, 2005.

Fair et al., "Electrowetting-based On-Chip Sample Processing for Integrated Microfluidics", IEEE Inter. Electron Devices Meeting (IEDM), 2003, 32.5.1-32.5.4.

Fair et al., "Integrated chemical/biochemical sample collection, pre-concentration, and analysis on a digital microfluidic lab-on-a-chip platform", Lab-on-a-Chip: Platforms, Devices, and Applications, Conf. 5591, SPIE Optics East, Philadelphia, Oct. 25-28, 2004.

Fair, "Scaling of Digital Microfluidic Devices for Picoliter Applications", The 6th International Electrowetting Meeting, Aug. 20-22, 2008, p. 14.

Fouillet, "Bio-Protocol Integration in Digital Microfluidic Chips", The 6th International Electrowetting Meeting, Aug. 20-22, 2008, p. 15.

Fouillet et al., "Design and Validation of a Complex Generic Fluidic Microprocessor Based on EWOD Droplet for Biological Applications", 9th International Conference on Miniaturized Systems for Chem and Life Sciences, Boston, MA, Oct. 9-13, 2005, 58-60.

Fouillet et al., "Digital microfluidic design and optimization of classic and new fluidic functions for lab on a chip systems", Microfluid Nanofluid, vol. 4, 2008, 159-165.

Graham et al., "Development of Quality Control Spots for Lysosomal Storage Disorders under cGMP", APHL Newborn Screening and Genetic Testing Symposium, San Diego, 2011.

Hua et al., "Multiplexed real-time polymerase chain reaction on a digital microfluidic platform", Analytical Chemistry, vol. 82, No. 6, Mar. 15, 2010, Published on Web, Feb. 12, 2010, 2310-2316.

Hua et al., "Rapid Detection of Methicillin-Resistant *Staphylococcus aureus* (MRSA) Using Digital Microfluidics", 12th Intl Conference on Miniaturized Systems for Chemistry and Life Sciences, Proc. μTAS, Oct. 12-16, 2008.

Jary et al., "Development of complete analytical system for Environment and homeland security", 14th International Conference on Biodetection Technologies 2009, Technological Responses to Biological Threats, Baltimore, MD; Abstract in Proceedings, poster distributed at conference, Jun. 25-26, 2009, 663.

Jary et al., "SmartDrop, Microfluidics for Biology", Forum 4i 2009, Grenoble, France; Flyer distributed at booth, May 14, 2009.

Jun et al., "Valveless Pumping using Traversing Vapor Bubbles in Microchannels", J. Applied Physics, vol. 83, No. 11, Jun. 1998, pp. 5658-5664.

Kim et al., "MEMS Devices Based on the Use of Surface Tension", Proc. Int. Semiconductor Device Research Symposium (ISDRS'99), Charlottesville, VA, Dec. 1999, pp. 481-484.

Kim, "Microelectromechanical Systems (MEMS) at the UCLA Micromanufacturing Lab", Dig. Papers, Int. Microprocesses and Nanotechnology Conf. (MNC'98), Kyungju, Korea, Jul. 1998, pp. 54-55.

Kim et al., "Micromachines Driven by Surface Tension", AIAA 99/3800, 30th AIAA Fluid Dynamics Conference, Norfolk, VA, (Invited lecture), Jun. 1999, pp. 1-6.

Kleinert et al., "Electric Field Assisted Convective Assembly of Colloidal Crystal Coatings", Symposium MM: Evaporative Self Assembly of Polymers, Nanoparticles, and DNA, 2010 MRS Spring Meeting, San Francisco, CA., Apr. 6-8, 2010.

Kleinert et al., "Electric Field-Assisted Convective Assembly of Large-Domain Colloidal Crystals", The 82nd Colloid & Surface Science Symposium, ACS Division of Colloid & Surface Science, North Carolina State University, Raleigh, NC. www.colloids2008.org., Jun. 15-18, 2008.

Kleinert, "Electric-Field-Assisted Convective Assembly of Colloidal Crystal Coatings", Langmuir, vol. 26(12), May 13, 2010, 10380-10385.

(56) References Cited

OTHER PUBLICATIONS

Lee et al., "Microactuation by Continuous Electrowetting Phenomenon and Silicon Deep Rie Process", Proc. MEMS (DSC—vol. 66) ASME Int. Mechanical Engineering Congress and Exposition, Anaheim, CA, Nov. 1998, 475-480.

Lee et al., "Liquid Micromotor Driven by Continuous Electrowetting", Proc. IEEE Micro Electro Mechanical Systems Workshop, Heidelberg, Germany, Jan. 1998, pp. 538-543.

Lee et al., "Theory and Modeling of Continuous Electrowetting Microactuation", Proc. MEMS (MEMS—vol. 1), ASME Int. Mechanical Engineering Congress and Exposition, Nashville, TN, Nov. 1999, pp. 397-403.

Malk et al., "EWOD in coplanar electrode configurations", Proceedings of ASME 2010 3rd Joint US-European Fluids Engineering Summer Meeting and 8th International Conference on Nanochannels, Microchannels, and Minichannels, http://asmedl.org/getabs/servlet/GetabsServlet?prog=normal&id=ASMECP002010054501000023900000, Aug. 1-5, 2010.

Marchand et al., "Organic Synthesis in Soft Wall-Free Microreactors: Real-Time Monitoring of Fluorogenic Reactions", Analytical Chemistry, vol. 80, Jul. 2, 2008, 6051-6055.

Millington et al., "Digital microfluidics: a future technology in the newborn screening laboratory", Seminars in Perinatology, vol. 34, Apr. 2010, 163-169.

Millington et al., "Digital Microfluidics: a novel platform for multiplexed detection of LSDs with potential for newborn screening", Association of Public Health Laboratories Annual Conference, San Antonio, TX, Nov. 4, 2008.

Millington et al., "Digital Microfluidics: A Novel Platform for Multiplexing Assays Used in Newborn Screening", Proceedings of the 7th International and Latin American Congress. Oral Presentations. Rev Invest Clin; vol. 61 (Supl. 1), 2009, 21-33.

Paik et al., "A digital-microfluidic approach to chip cooling", IEEE Design & Test of Computers, vol. 25, Jul. 2008, 372-381.

Paik et al., "Adaptive Cooling of Integrated Circuits Using Digital Microfluidics", IEEE Transactions on VLSI, vol. 16, No. 4, 2008, 432-443.

Paik et al., "Adaptive Cooling of Integrated Circuits Using Digital Microfluidics", accepted for publication in IEEE Transactions on VLSI Systems, 2007, and Artech House, Norwood, MA, 2007.

Paik, "Adaptive Hot-Spot Cooling of Integrated Circuits Using Digital Microfluidics", Dissertation, Dept. of Electrical and Computer Engineering, Duke University, Apr. 25, 2006, 1-188.

Paik et al., "Adaptive hot-spot cooling of integrated circuits using digital microfluidics", Proceedings ASME International Mechanical Engineering Congress and Exposition, Orlando, Florida, USA. IMECE2005-81081, Nov. 5-11, 2005, 1-6.

Paik et al., "Coplanar Digital Microfluidics Using Standard Printed Circuit Board Processes", 9th International Conference on Miniaturized Systems for Chemistry and Life Sciences (MicroTAS), Boston, MA; Poster, 2005.

Paik et al., "Coplanar Digital Microfluidics Using Standard Printed Circuit Board Processes", 9th Int'l Conf. on Miniaturized Systems for Chemistry and Life Sciences, Boston, MA, Oct. 9-13, 2005, 566-68.

Paik et al., "Droplet-Based Hot Spot Cooling Using Topless Digital Microfluidics on a Printed Circuit Board", Int'l Workshops on Thermal Investigations of ICs and Systems (THERMINIC), 2005, 278-83.

Paik et al., "Electrowetting-based droplet mixers for microfluidic systems", Lab on a Chip (LOC), vol. 3. (more mixing videos available, along with the article, at LOC's website), 2003, 28-33.

Paik et al., "Programmable Flow-Through Real Time PCR Using Digital Microfluidics", 11th International Conference on Miniaturized Systems for Chemistry and Life Sciences, Paris, France, Oct. 7-11, 2007, 1559-1561.

Paik et al., "Programmable flow-through real-time PCR using digital microfluidics", Proc. Micro Total Analysis Systems (μTAS), Handout, 2007.

Paik et al., "Programmable flow-through real-time PCR using digital microfluidics", Proc. Micro Total Analysis Systems (μTAS), Poster, 2007.

Paik et al., "Rapid Droplet Mixers for Digital Microfluidic Systems", Masters Thesis, Duke Graduate School., 2002, 1-82.

Paik et al., "Rapid droplet mixers for digital microfluidic systems", Lab on a Chip, vol. 3. (More mixing videos available, along with the article, at LOC's website.), 2003, 253-259.

Paik et al., "Thermal effects on Droplet Transport in Digital Microfluids with Application to Chip Cooling Processing for Integrated Microfluidics", International Conference on Thermal, Mechanics, and Thermomechanical Phenomena in Electronic Systems (ITherm), 2004, 649-654.

Pamula, "A digital microfluidic platform for multiplexed explosive detection", Chapter 18, Electronics Noses and Sensors for the Detection of Explosives, Eds., J.W. Gardner and J. Yinon, Kluwer Academic Publishers, 2004.

Pamula et al., "A droplet-based lab-on-a-chip for colorimetric detection of nitroaromatic explosives", Proceedings of Micro Electro Mechanical Systems, 2005, 722-725.

Pamula et al., "Cooling of integrated circuits using droplet-based microfluidics", Proc. ACM Great Lakes Symposium on VLSI, Apr. 2003, 84-87.

Pamula, "Digital microfluidic lab-on-a-chip for multiplexing tests in newborn screening", Newborn Screening Summit: Envisioning a Future for Newborn Screening, Bethesda, MD, Dec. 7, 2009.

Pamula et al., "Digital microfluidic lab-on-a-chip for protein crystallization", 5th Protein Structure Initiative "Bottlenecks" Workshop, NIH, Bethesda, MD, Apr. 13-14, 2006, I-16.

Pamula et al., "Digital Microfluidic Methods in Diagnosis of Neonatal Biochemical Abnormalities", Developing Safe and Effective Devices and Instruments for Use in the Neonatal Intensive Care for the 21st Century, Pediatric Academic Societies' Annual Meeting, Vancouver, Canada, May 1-4, 2010.

Pamula et al., "Digital Microfluidic Platform for Multiplexing LSD Assays in Newborn Screening", LSD World Meeting, Las Vegas, NV, Feb. 16-18, 2011.

Pamula et al., "Digital Microfluidics Platform for Lab-on-a-chip applications", Duke University Annual Post Doctoral Research Day, 2002.

Pamula et al., "Microfluidic electrowetting-based droplet mixing", IEEE, 2002, 8-10.

Pamula, "Sample Preparation and Processing using Magnetic Beads on a Digital Microfluidic Platform", CHI's Genomic Sample Prep, San Francisco, CA, Jun. 9-10, 2009.

Pamula, "Sample-to-sequence-molecular diagnostics on a digital microfluidic lab on a chip", Pre-conference workshops, 4th International Conference on Birth Defects and Disabilities in the Developing World, New Dehli, India, Oct. 4, 2009.

Pollack et al., "Applications of Electrowetting-Based Digital Microfluidics in Clinical Diagnostics", Expert Rev. Mol. Diagn., vol. 11(4), 2011, 393-407.

Pollack et al., "Continuous sequencing-by-synthesis-based on a digital microfluidic platform", National Human Genome Research Institute, Advanced DNA Sequencing Technology Development Meeting, Chapel Hill, NC, Mar. 10-11, 2010.

Pollack, et al., "Electrowetting-Based Actuation of Droplets for Integrated Microfluidics", Lab on a Chip (LOC), vol. 2, 2002, 96-101.

Pollack et al., "Electrowetting-based actuation of liquid droplets for microfluidic applications", Appl. Phys. Letters, vol. 77, No. 11, Sep. 11, 2000, 1725-1726.

Pollack, "Electrowetting-based Microactuation of Droplets for Digital Microfluidics", PhD Thesis, Department of Electrical and Computer Engineering, Duke University, 2001.

Pollack et al., "Electrowetting-Based Microfluidics for High-Throughput Screening", smallTalk 2001 Conference Program Abstract, San Diego, Aug. 27-31, 2001, 149.

Pollack et al., "Investigation of electrowetting-based microfluidics for real-time PCR applications", Proc. 7th Int'l Conference on Micro Total Analysis Systems (mTAS), Squaw Valley, CA, Oct. 5-9, 2003, 619-622.

Pollack, "Lab-on-a-chip platform based digital microfluidics", The 6th International Electrowetting Meeting, Aug. 20-22, 2008, 16.

(56) References Cited

OTHER PUBLICATIONS

Punnamaraju, "Voltage and Photo Induced Effects in Droplet-Interface-Bilayer Lipid", PhD Thesis, University of Cincinnati, 2011.
Punnamaraju et al., "Voltage Control of Droplet Interface Bilayer Lipid Membrane Dimensions", Langmuir The ACS Journal of Surfaces and Colloids, vol. 27, Issue 2, 2011, Published on Web, Dec. 10, 2010, 618-626.
Ren et al., "Automated electrowetting-based droplet dispensing with good reproducibility", Proc. Micro Total Analysis Systems (mTAS), 7th Int. Conf.on Miniaturized Chem and Biochem Analysis Systems, Squaw Valley, CA, Oct. 5-9, 2003, 993-996.
Ren et al., "Automated on-chip droplet dispensing with volume control by electro-wetting actuation and capacitance metering", Sensors and Actuators B: Chemical, vol. 98, Mar. 2004, 319-327.
Ren et al., "Design and testing of an interpolating mixing architecture for electrowetting-based droplet-on-chip chemical dilution", Transducers, 12th International Conference on Solid- State Sensors, Actuators and Microsystems, 2003, 619-622.
Ren et al., "Dynamics of electro-wetting droplet transport", Sensors and Actuators B (Chemical), vol. B87, No. 1, Nov. 15, 2002, 201-206.
Ren et al., "Micro/Nano Liter Droplet Formation and Dispensing by Capacitance Metering and Electrowetting Actuation", IEEE-NANO, 2002, 369-372.
Rival et al., "EWOD Digital Microfluidic Device for Single Cells Sample Preparation and Gene Expression Analysis", Lab Automation 2010, Palm Springs Convention Center, Palm Springs, CA, USA; Abstract in Proceedings, Poster distributed at conference, Jan. 23-27, 2010.
Rival et al., "Expression de genes de quelques cellules sur puce EWOD/Gene expression of few cells on EWOD chip", iRTSV,http://www-dsv.cea.fr/var/plain/storage/original/media/File/iRTSV/thema_08(2).pdf (english translation), Winter 2009-2010.
Rival et al., "Towards Single Cells Gene Expression on EWOD Lab on Chip", ESONN 2008, Grenoble, France; Poster presented, Aug. 26, 2008.
Rival et al., "Towards single cells gene expression on EWOD lab on chip", ESONN, Grenoble, France, abstract in proceedings, Aug. 2008.
Rival et al., "Towards single cells gene expression preparation and analysis on ewod lab on chip", Nanobio Europe 2009, Poster distributed at conference, Jun. 16-18, 2009.
Rival et al., "Towards single cells gene expression preparation and analysis on ewod lab on chip", Nanobio Europe 2009, Abstract in proceedings, Jun. 16-18, 2009.
Rival et al., "Towards single cells gene expression preparation and analysis on ewod lab on chip", Lab on Chip Europe 2009 poster distributed at Conference, May 19-20, 2009.
Rival et al., "Towards single cells gene expression preparation and analysis on ewod lab on chip", Lab on Chip Europe 2009, Abstract in proceedings, May 19-20, 2009.
Rouse et al., "Digital microfluidics: a novel platform for multiplexing assays used in newborn screening", Poster 47, 41st AACC's Annual Oak Ridge Conference Abstracts, Clinical Chemistry, vol. 55, 2009, 1891.
Sherman et al., "Flow Control by Using High-Aspect-Ratio, In-Plane Microactuators", Sensors and Actuators, vol. 73, 1999, pp. 169-175.
Sherman et al., "In-Plane Microactuator for Fluid Control Application", Proc. IEEE Micro Electro Mechanical Systems Workshop, Heidelberg, Germany, Jan. 1998, pp. 454-459.
Shi et al., "Evaluation of stability of fluorometric reagent kits for screening of Lysosomal Storage Disorders", APHL Newborn Screening and Genetic Testing Symposium, San Diego, 2011.
Sista et al., "96-Immunoassay Digital Microfluidic Multiwell Plate", Proc. µTAS, Oct. 12-16, 2008.
Sista, "Development of a Digital Microfluidic Lab-on-a-Chip for Automated Immunoassays with Magnetically Responsive Beads", PhD Thesis, Department of Chemical Engineering, Florida State University, 2007.
Sista et al., "Development of a digital microfluidic platform for point of care testing", Lab on a chip, vol. 8, Dec. 2008, First published as an Advance Article on the web, Nov. 5, 2008, 2091-2104.
Sista et al., "Digital Microfluidic platform for multiplexing LSD assays in newborn screening", APHL Newborn Screening and Genetic Testing Symposium, Orlando, May 3-6, 2010.
Sista et al., "Heterogeneous immunoassays using magnetic beads on a digital microfluidic platform", Lab on a Chip, vol. 8, Dec. 2008, First published as an Advance Article on the web, Oct. 14, 2008, 2188-2196.
Sista et al., "Performance of a digital microfluidic assay for Gaucher and Hurler disorders", APHL Newborn Screening and Genetic Testing Symposium, San Diego, 2011.
Sista et al., "Rapid, Single-Step Assay for Hunter Syndrome in Dried Blood Spots Using Digital Microfluidics", Clinica Chimica Acta, vol. 412, 2011, 1895-97.
Sista et al., "Spatial multiplexing of immunoassays for small-volume samples", 10th PI Meeting IMAT, Bethesda, 2009.
Srinivasan et al., "3-D imaging of moving droplets for microfluidics using optical coherence tomography", Proc. 7th International Conference on Micro Total Analysis Systems (mTAS), Squaw Valley, CA, Oct. 5-9, 2003, 1303-1306.
Srinivasan et al., "A digital microfluidic biosensor for multianalyte detection", Proc. IEEE 16th Annual Int'l Conf. on Micro Electro Mechanical Systems Conference, 2003, 327-330.
Srinivasan, "A Digital Microfluidic Lab-on-a-Chip for Clinical Diagnostic Applications", Ph.D. thesis, Dept of Electrical and Computer Engineering, Duke University, 2005.
Srinivasan et al., "An integrated digital microfluidic lab-on-a-chip for clinical diagnostics on human physiological fluids", Lab on a Chip, vol. 4, 2004, 310-315.
Srinivasan et al., "Clinical diagnostics on human whole blood, plasma, serum, urine, saliva, sweat and tears on a digital microfluidic platform", Proc. 7th International Conference on Micro Total Analysis Systems (mTAS), Squaw Valley, CA, Oct. 5-9, 2003, 1287-1290.
Srinivasan et al., "Digital Microfluidic Lab-on-a-Chip for Protein Crystallization", The 82nd ACS Colloid and Surface Science Symposium, 2008.
Srinivasan et al., "Digital Microfluidics: a novel platform for multiplexed detection of lysosomal storage diseases for newborn screening", AACC Oak Ridge Conference Abstracts, Clinical Chemistry, vol. 54, 2008, 1934.
Srinivasan et al., "Droplet-based microfluidic lab-on-a-chip for glucose detection", Analytica Chimica Acta, vol. 507, No. 1, 2004, 145-150.
Srinivasan et al., "Electrowetting", Chapter 5, Methods in Bioengineering: Biomicrofabrication and Biomicrofluidics, Ed. J.D. Zahn, ISBN: 9781596934009, Artech House Publishers, 2010.
Srinivasan et al., "Feasibility of a point of care newborn screening platform for hyperbilirubinemia", APHL Newborn Screening and Genetic Testing Symposium, San Diego, 2011.
Srinivasan et al., "Low cost digital microfluidic platform for protein crystallization", Enabling Technologies for Structural Biology, NIGMS Workshop, Bethesda, MD., Mar. 4-6, 2009, J-23.
Srinivasan et al., "Protein Stamping for MALDI Mass Spectrometry Using an Electrowetting-based Microfluidic Platform", Lab-on-a-Chip: Platforms, Devices, and Applications, Conf. 5591, SPIE Optics East, Philadelphia, Oct. 25-28, 2004.
Srinivasan et al., "Scalable Macromodels for Microelectromechanical Systems", Technical Proc. 2001 Int. Conf. on Modeling and Simulation of Microsystems, 2001, 72-75.
Su et al., "Yield Enhancement of Digital Microfluidics-Based Biochips Using Space Redundancy and Local Reconfiguration", Proc. Design, Automation and Test in Europe (Date) Conf., IEEE, 2005, 1196-1201.
Sudarsan et al., "Printed circuit technology for fabrication of plastic based microfluidic devices", Analytical Chemistry vol. 76, No. 11, Jun. 1, 2004, Previously published online, May 2004, 3229-3235.
Thwar et al., "DNA sequencing using digital microfluidics", Poster 42, 41st AACC's Annual Oak Ridge Conference Abstracts, Clinical Chemistry vol. 55, 2009, 1891.
Wang et al., "Comparison of enzyme activities for Pompe, Fabry, and Gaucher diseases on CDC's Quality Control spots between

(56) References Cited

OTHER PUBLICATIONS microplate fluorometry, mass spectrometry, and digital microfluidic fluorometry", APHL Newborn Screening and Genetic Testing Symposium, San Diego, 2011.

Wang et al., "Droplet-based micro oscillating-flow PCR chip", J. Micromechanics and Microengineering, vol. 15, 2005, 1369-1377.

Wang et al., "Efficient in-droplet separation of magnetic particles for digital microfluidics", Journal of Micromechanics and Microengineering, vol. 17, 2007, 2148-2156.

Wulff-Burchfield et al., "Microfluidic platform versus conventional real-time polymerase chain reaction for the detection of Mycoplasma pneumoniae in respiratory specimens", Diagnostic Microbiology and Infectious Disease, vol. 67, 2010, 22-29.

Xu et al., "A Cross-Referencing-Based Droplet Manipulation Method for High-Throughput and Pin-Constrained Digital Microfluidic Arrays", Proceedings of conference on Design, Automation and Test in Europe, Apr. 2007.

Xu et al., "Automated Design of Pin-Constrained Digital Microfluidic Biochips Under Droplet-Interference Constraints", ACM Journal on Emerging Technologies is Computing Systems, vol. 3(3), 2007, 14:1-14:23.

Xu et al., "Automated solution preparation on a digital microfluidic lab-on-chip", PSI Bottlenecks Workshop, 2008.

Xu et al., "Automated, Accurate and Inexpensive Solution-Preparation on a Digital Microfluidic Biochip", Proc. IEEE Biomedical Circuits and Systems Conference (BioCAS), 2008, 301-304.

Xu et al., "Defect-Aware Synthesis of Droplet-Based Microfluidic Biochips", IEEE, 20th International Conference on VLSI Design, 2007.

Xu et al., "Defect-Tolerant Design and Optimization of a Digital Microfluidic Biochip for Protein Crystallization", IEEE Transactions on Computer Aided Design, vol. 29, No. 4, 2010, 552-565.

Xu et al., "Design and Optimization of a Digital Microfluidic Biochip for Protein Crystallization", Proc. IEEE/ACM International Conference on Computer-Aided Design (ICCAD), Nov. 2008, 297-301.

Xu et al., "Digital Microfluidic Biochip Design for Protein Crystallization", IEEE-NIH Life Science Systems and Applications Workshop, LISA, Bethesda, MD, Nov. 89, 2007, 140-143.

Xu et al., "Droplet-Trace-Based Array Partitioning and a Pin Assignment Algorithm for the Automated Design of Digital Microfluidic Biochips", CODES, 2006, 112-117.

Xu et al., "Integrated Droplet Routing in the Synthesis of Microfluidic Biochips", IEEE, 2007, 948-953.

Xu et al., "Parallel Scan-Like Test and Multiple-Defect Diagnosis for Digital Microfluidic Biochips", IEEE Transactions on Biomedical Circuits and Systems, vol. 1(2), Jun. 2007, 148-158.

Xu et al., "Parallel Scan-Like Testing and Fault Diagnosis Technique for Digital Microfluidic Biochips", Proceedings of the 12th IEEE European Test Symposium (ETS), Freiburg, Germany, May 20-24, 2007, 63-68.

Yang et al., "Manipulation of droplets in microfluidic systems", Trends in Analytical Chemistry, vol. 29, Feb. 2010, 141-157.

Yao et al., "Spot Cooling Using Thermoelectric Microcooler", Proc. 18th Int. Thermoelectric Conf, Baltimore, VA, pp. 256-259, Aug. 1999.

Yi et al., "Channel-to-droplet extractions for on-chip sample preparation", Solid-State Sensor, Actuators and Microsystems Workshop (Hilton Head '06), Hilton Head Island, SC, Jun. 2006, 128-131.

Yi et al., "Characterization of electrowetting actuation on addressable single-side coplanar electrodes", Journal of Micromechanics and Microengineering, vol. 16. Oct. 2006, 2053-2059.

Yi et al., "EWOD Actuation with Electrode-Free Cover Plate", Digest of Tech. papers, 13th International Conference on Solid-State Sensors, Actuators and Microsystems (Transducers '05), Seoul, Korea, Jun. 5-9, 2005, 89-92.

Yi et al., "Geometric surface modification of nozzles for complete transfer of liquid drops", Solid-State Sensor, Actuator and Microsystems Workshop, Hilton Head Island, South Carolina, Jun. 6-10, 2004, 164-167.

Yi, "Soft Printing of Biological Liquids for Micro-arrays: Concept, Principle, Fabrication, and Demonstration", Ph.D. dissertation, UCLA, 2004.

Yi et al., "Soft Printing of Droplets Digitized by Electrowetting", Transducers 12th Int'l Conf. on Solid State Sensors, Actuators and Microsystems, Boston, Jun. 8-12, 2003, 1804-1807.

Yi et al., "Soft Printing of Droplets Pre-Metered by Electrowetting", Sensors and Actuators A: Physical, vol. 114, Jan. 2004, 347-354.

Zeng et al., "Actuation and Control of Droplets by Using Electrowetting-on-Dielectric", Chin. Phys. Lett., vol. 21(9), 2004, 1851-1854.

Zhao et al., "Droplet Manipulation and Microparticle Sampling on Perforated Microfilter Membranes", J. Micromech. Microeng., vol. 18, 2008, 1-11.

Zhao et al., "In-droplet particle separation by travelling wave dielectrophoresis (twDEP) and EWOD", Solid-State Sensor, Actuators and Microsystems Workshop (Hilton Head '06), Hilton Head Island, SC, Jun. 2006, 181-184.

Zhao et al., "Micro air bubble manipulation by electrowetting on dielectric (EWOD): transporting, splitting, merging and eliminating of bubbles", Lab on a chip, vol. 7, 2007, First published as an Advance Article on the web, Dec. 4, 2006, 273-280.

Zhao et al., "Microparticle Concentration and Separation byTraveling-Wave Dielectrophoresis (twDEP) for Digital Microfluidics", J. Microelectromechanical Systems, vol. 16, No. 6, Dec. 2007, 1472-1481.

Zhao et al., "Synchronization of Concurrently-Implemented Fluidic Operations in Pin-Constrained Digital Microfluidic Biochips", VLSI Design, (Best Paper Award), 2010.

International Search Report dated Dec. 26, 2011 from PCT International Application No. PCT/US2011/030543.

* cited by examiner

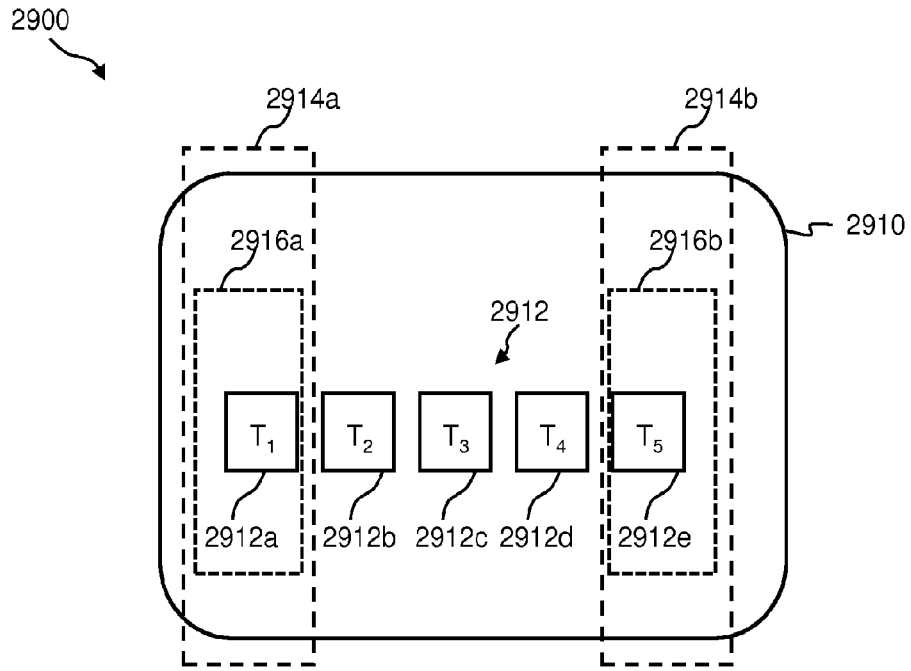
Figure 29A
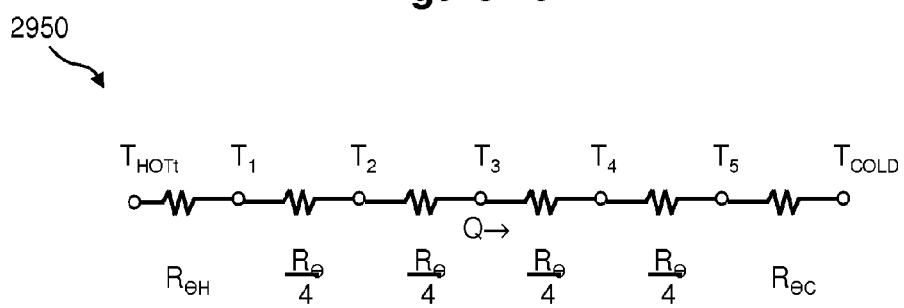
Figure 29B
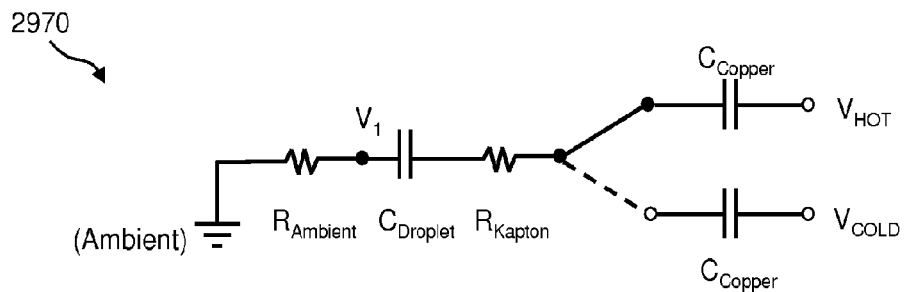
Figure 29C        ($V_{HOT} > V_{COLD} >$ Ambient)

DROPLET OPERATIONS PLATFORM

1 RELATED APPLICATIONS

This patent application is related to and claims priority to U.S. Provisional Patent Application No. 61/318,851, filed on Mar. 30, 2010, entitled "Sample-to-Result Molecular Diagnostic Platform," and 61/361,576, filed on Jul. 6, 2010, entitled "Sample-to-Result Molecular Diagnostic Platform," the entire disclosures of which are incorporated herein by reference.

2 FIELD OF THE INVENTION

The invention generally relates to a droplet actuator device and methods for integrated sample preparation and analysis of a sample, such as a biological sample, for the presence and/or quantity of an analyte.

3 BACKGROUND OF THE INVENTION

A droplet actuator typically includes one or more substrates configured to form a surface or gap for conducting droplet operations. The one or more substrates establish the droplet operations surface or gap and may also include electrodes arrange to conduct the droplet operations. The droplet operations substrate or the gap between the substrates is typically coated or filled with a filler fluid that is immiscible with the liquid that forms the droplets.

Droplet actuators are used in a variety of applications, including molecular diagnostic assays, such as quantitative polymerase chain reaction (qPCR) and immunoassays. Molecular diagnostic assays are used in a wide variety of settings, such as infectious pathogen detection and point-of-care diagnosis. Current microfluidic protocols for sample preparation typically begin with analyte capture beads suspended in a small volume (e.g., 250 microliters (µL)) of lysed sample. Individual droplets are then dispensed and the capture beads are concentrated in a single droplet over a permanent magnet. However, bead dispensing, concentrating, and washing are time-consuming steps and significantly increase the time-to-result of a diagnostic assay. Consequently, new approaches are needed to achieve rapid "sample-to-result" molecular diagnostics for point-of-care use.

4 BRIEF DESCRIPTION OF THE INVENTION

The invention relates to a droplet actuator device and methods for integrated sample preparation and analysis of a biological sample. Using digital microfluidics technology, the droplet actuator device and methods of the invention provide the ability to perform sample preparation and analysis from a single biological sample on the same droplet actuator. The droplet actuator device uses a large input sample volume (e.g., about 1 milliliter (mL)) and provides for rapid capture and concentration of target analytes for subsequent molecular diagnostic assays (e.g., qPCR, immunoassay).

In one embodiment the invention provides droplet actuator device for conducting droplet operations. The droplet actuator device may include a bottom substrate and a top substrate separated from each other to form a gap therebetween; an arrangement of droplet operations electrodes arranged on one or both of the bottom and/or top substrates for conducting droplet operations thereon; a reagent storage layer comprising one or more compartments bound to the top substrate; and one or more openings arranged to provide a fluidic path from the one or more compartments into the gap, upon breach of a breachable seal separating the one or more compartments and openings.

In another embodiment, the droplet actuator device and methods of the invention provide for increased droplet throughput for rapid sample preparation and analysis. In one example, increased droplet throughput is provided by manipulation of larger sized droplets.

In another embodiment, the droplet actuator device and methods of the invention provide for efficient and controllable loading (e.g., reliable loading) of a large sample volume (e.g., about 1 mL) into a droplet actuator. In one example, reliable loading is provided by storage of a sample in an on-actuator reservoir in an energetically favorable state.

In another embodiment, the droplet actuator device and methods of the invention provide for effective mixing of analyte capture beads within a sample volume of about 1 mL. In one example, electrowetting may be used to mix a sample stored in an on-actuator reservoir.

In another embodiment, the droplet actuator device and methods of the invention provide for rapid and efficient concentration and collection of analyte capture beads, e.g., magnetically responsive capture beads. In one example, one or more stationary magnets may be arranged in proximity of a sample stored in an on-actuator reservoir. In another example, a movable magnet may be used for concentration and collection of analyte capture beads.

In yet another embodiment, the invention provides a detection system that uses a single excitation beam and a single detection beam to collect multiple (e.g., four) different fluorescent signals at a single detection spot on a droplet actuator.

In yet another embodiment, the invention provides methods for controlling heat flow and minimizing thermal losses in one or more temperature control zones on a droplet actuator.

In yet another embodiment, the invention provides devices and methods for generating heat off-actuator and transferring the heat to designated temperature control zones on a droplet actuator.

In yet another embodiment, the invention provides methods for controlling the temperature of a droplet by transporting the droplet from one temperature region to another temperature region (position dithering) on a droplet actuator.

Further features and other aspects of the invention are more clearly evident from the following detailed discussion and from the appended claims.

5 DEFINITIONS

As used herein, the following terms have the meanings indicated.

"Activate," with reference to one or more electrodes, means effecting a change in the electrical state of the one or more electrodes which, in the presence of a droplet, results in a droplet operation.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical and other three dimensional shapes. The bead may, for example, be capable of being transported in a droplet on a droplet actuator or otherwise configured with respect to a droplet actuator in a manner which permits a droplet on the droplet actuator to be brought into contact with the bead, on the droplet actuator and/or off the droplet actuator. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead or one component only of a bead. The remainder of the bead may include, among other things, polymeric material, coatings, and moieties which permit attachment of an assay reagent. Examples of suitable magnetically responsive beads include flow cytometry microbeads, polystyrene microparticles and nanoparticles, functionalized polystyrene microparticles and nanoparticles, coated polystyrene microparticles and nanoparticles, silica microbeads, fluorescent microspheres and nanospheres, functionalized fluorescent microspheres and nanospheres, coated fluorescent microspheres and nanospheres, color dyed microparticles and nanoparticles, magnetic microparticles and nanoparticles, superparamagnetic microparticles and nanoparticles (e.g., DYNABEADS® particles, available from Invitrogen Corp., Carlsbad, Calif., fluorescent microparticles and nanoparticles, coated magnetic microparticles and nanoparticles, ferromagnetic microparticles and nanoparticles, coated ferromagnetic microparticles and nanoparticles, and those described in U.S. Patent Publication Nos. 20050260686, entitled "Multiplex flow assays preferably with magnetic particles as solid phase," published on Nov. 24, 2005; 20030132538, entitled "Encapsulation of discrete quanta of fluorescent particles," published on Jul. 17, 2003; 20050118574, entitled "Multiplexed Analysis of Clinical Specimens Apparatus and Method," published on Jun. 2, 2005; 20050277197. Entitled "Microparticles with Multiple Fluorescent Signals and Methods of Using Same," published on Dec. 15, 2005; 20060159962, entitled "Magnetic Microspheres for use in Fluorescence-based Applications," published on Jul. 20, 2006; the entire disclosures of which are incorporated herein by reference for their teaching concerning beads and magnetically responsive materials and beads. Beads may be pre-coupled with a biomolecule (ligand). The ligand may, for example, be an antibody, protein or antigen, DNA/RNA probe or any other molecule with an affinity for the desired target. Examples of droplet actuator techniques for immobilizing magnetically responsive beads and/or non-magnetically responsive beads and/or conducting droplet operations protocols using beads are described in U.S. patent application Ser. No. 11/639,566, entitled "Droplet-Based Particle Sorting," filed on Dec. 15, 2006; U.S. Patent Application No. 61/039,183, entitled "Multiplexing Bead Detection in a Single Droplet," filed on Mar. 25, 2008; U.S. Patent Application No. 61/047,789, entitled "Droplet Actuator Devices and Droplet Operations Using Beads," filed on Apr. 25, 2008; U.S. Patent Application No. 61/086,183, entitled "Droplet Actuator Devices and Methods for Manipulating Beads," filed on Aug. 5, 2008; International Patent Application No. PCT/US2008/053545, entitled "Droplet Actuator Devices and Methods Employing Magnetic Beads," filed on Feb. 11, 2008; International Patent Application No. PCT/US2008/058018, entitled "Bead-based Multiplexed Analytical Methods and Instrumentation," filed on Mar. 24, 2008; International Patent Application No. PCT/US2008/058047, "Bead Sorting on a Droplet Actuator," filed on Mar. 23, 2008; and International Patent Application No. PCT/US2006/047486, entitled "Droplet-based Biochemistry," filed on Dec. 11, 2006; the entire disclosures of which are incorporated herein by reference. Bead characteristics may be employed in the multiplexing aspects of the invention. Examples of beads having characteristics suitable for multiplexing, as well as methods of detecting and analyzing signals emitted from such beads, may be found in U.S. Patent Publication No. 20080305481, entitled "Systems and Methods for Multiplex Analysis of PCR in Real Time," published on Dec. 11, 2008; U.S. Patent Publication No. 20080151240, "Methods and Systems for Dynamic Range Expansion," published on Jun. 26, 2008; U.S. Patent Publication No. 20070207513, entitled "Methods, Products, and Kits for Identifying an Analyte in a Sample," published on Sep. 6, 2007; U.S. Patent Publication No. 20070064990, entitled "Methods and Systems for Image Data Processing," published on Mar. 22, 2007; U.S. Patent Publication No. 20060159962, entitled "Magnetic Microspheres for use in Fluorescence-based Applications," published on Jul. 20, 2006; U.S. Patent Publication No. 20050277197, entitled "Microparticles with Multiple Fluorescent Signals and Methods of Using Same," published on Dec. 15, 2005; and U.S. Patent Publication No. 20050118574, entitled "Multiplexed Analysis of Clinical Specimens Apparatus and Method," published on Jun. 2, 2005.

"Droplet" means a volume of liquid on a droplet actuator. Typically, a droplet is at least partially bounded by filler fluid. For example, a droplet may be completely surrounded by filler fluid or may be bounded by filler fluid and one or more surfaces of the droplet actuator. As another example, a droplet may be bounded by filler fluid, one or more surfaces of the droplet actuator, and the atmosphere. As yet another example, a droplet may be bounded by filler fluid and the atmosphere. Droplets may, for example, be aqueous or non-aqueous or may be mixtures or emulsions including aqueous and non-aqueous components. Droplets may take a wide variety of shapes; nonlimiting examples include generally disc shaped, slug shaped, truncated sphere, ellipsoid, spherical, partially compressed sphere, hemispherical, ovoid, cylindrical, combinations of such shapes, and various shapes formed during droplet operations, such as merging or splitting or formed as a result of contact of such shapes with one or more surfaces of a droplet actuator. For examples of droplet fluids that may be subjected to droplet operations using the approach of the invention, see International Patent Application No. PCT/US 06/47486, entitled, "Droplet-Based Biochemistry," filed on Dec. 11, 2006. In various embodiments, a droplet may include a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. Moreover, a droplet may include a reagent, such as water, deionized water, saline solutions, acidic solutions, basic solutions, detergent solutions and/or buffers. Other examples of droplet contents include reagents, such as a reagent for a biochemical protocol, such as a nucleic acid amplification protocol, an affinity-based assay protocol, an enzymatic assay protocol, a sequencing protocol, and/or a protocol for analyses of biological fluids.

"Droplet Actuator" means a device for manipulating droplets. For examples of droplet actuators, see Pamula et al., U.S. Pat. No. 6,911,132, entitled "Apparatus for Manipulating Droplets by Electrowetting-Based Techniques," issued on Jun. 28, 2005; Pamula et al., U.S. patent application Ser. No. 11/343,284, entitled "Apparatuses and Methods for Manipulating Droplets on a Printed Circuit Board," filed on filed on Jan. 30, 2006; Pollack et al., International Patent Application No. PCT/US2006/1047486, entitled "Droplet-Based Biochemistry," filed on Dec. 11, 2006; Shenderov, U.S. Pat. No. 6,773,566, entitled "Electrostatic Actuators for Microfluidics and Methods for Using Same," issued on Aug. 10, 2004 and U.S. Pat. No. 6,565,727, entitled "Actuators for Microfluidics Without Moving Parts," issued on Jan. 24, 2000; Kim et al., U.S. patent application Ser. No. 10/343,261, entitled "Electrowetting-driven Micropumping," filed on Jan. 27, 2003; Ser. No. 11/275,668, entitled "Method and Apparatus for Promoting the Complete Transfer of Liquid Drops from a Nozzle," filed on Jan. 23, 2006; Ser. No. 11/460,188, entitled "Small Object Moving on Printed Circuit Board," filed on Jan. 23, 2006; Ser. No. 12/465,935, entitled "Method for Using Magnetic Particles in Droplet Microfluidics," filed on May 14, 2009; Ser. No. 12/513,157, entitled "Method and apparatus for real-time feedback control of electrical manipulation of droplets on chip," filed on Apr. 30, 2009; Velev, U.S. Pat. No. 7,547,380, entitled "Droplet Transportation Devices and Methods Having a Fluid Surface," issued on Jun. 16, 2009; Sterling et al., U.S. Pat. No. 7,163,612, entitled "Method, Apparatus and Article for Microfluidic Control via Electrowetting, for Chemical, Biochemical and Biological Assays and the Like," issued on Jan. 16, 2007; Becker and Gascoyne et al., U.S. Pat. No. 7,641,779, entitled "Method and Apparatus for Programmable fluidic Processing," issued on Jan. 5, 2010, and U.S. Pat. No. 6,977,033, entitled "Method and Apparatus for Programmable fluidic Processing," issued on Dec. 20, 2005; Decre et al., U.S. Pat. No. 7,328,979, entitled "System for Manipulation of a Body of Fluid," issued on Feb. 12, 2008; Yamakawa et al., U.S. Patent Pub. No. 20060039823, entitled "Chemical Analysis Apparatus," published on Feb. 23, 2006; Wu, International Patent Pub. No. WO/2009/003184, entitled "Digital Microfluidics Based Apparatus for Heat-exchanging Chemical Processes," published on Dec. 31, 2008; Fouillet et al., U.S. Patent Pub. No. 20090192044, entitled "Electrode Addressing Method," published on Jul. 30, 2009; Fouillet et al., U.S. Pat. No. 7,052,244, entitled "Device for Displacement of Small Liquid Volumes Along a Micro-catenary Line by Electrostatic Forces," issued on May 30, 2006; Marchand et al., U.S. Patent Pub. No. 20080124252, entitled "Droplet Microreactor," published on May 29, 2008; Adachi et al., US. Patent Pub. No. 20090321262, entitled "Liquid Transfer Device," published on Dec. 31, 2009; Roux et al., U.S. Patent Pub. No. 20050179746, entitled "Device for Controlling the Displacement of a Drop Between two or Several Solid Substrates," published on Aug. 18, 2005; Dhindsa et al., "Virtual Electrowetting Channels: Electronic Liquid Transport with Continuous Channel Functionality," *Lab Chip,* 10:832-836 (2010); the disclosures of which are incorporated herein by reference, along with their priority documents. Certain droplet actuators will include a base substrate, droplet operations electrodes associated with the substrate, one or more dielectric and/or hydrophobic layers atop the substrate and/or electrodes forming a droplet operations surface, and optionally, a top substrate separated from the droplet operations surface by a gap. The base and top substrates may in some cases be formed as one integral component. One or more reference electrodes may be provided on the top and/or bottom substrates and/or in the gap. In various embodiments, the manipulation of droplets by a droplet actuator may be electrode mediated, e.g., electrowetting mediated or dielectrophoresis mediated or Coulombic force mediated. Examples of other methods of controlling fluid flow that may be used in the droplet actuators of the invention include devices that induce hydrodynamic fluidic pressure, such as those that operate on the basis of mechanical principles (e.g., external syringe pumps, pneumatic membrane pumps, vibrating membrane pumps, vacuum devices, centrifugal forces, piezoelectric/ultrasonic pumps and acoustic forces); electrical or magnetic principles (e.g., electroosmotic flow, electrokinetic pumps, ferrofluidic plugs, electrohydrodynamic pumps, attraction or repulsion using magnetic forces and magnetohydrodynamic pumps); thermodynamic principles (e.g., gas bubble generation/phase-change-induced volume expansion); other kinds of surface-wetting principles (e.g., electrowetting, and optoelectrowetting, as well as chemically, thermally, structurally and radioactively induced surface-tension gradients); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential. In certain embodiments, combinations of two or more of the foregoing techniques may be employed in droplet actuators of the invention.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to volume of the resulting droplets (e.g., the volume of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be electrode-mediated. In some cases, droplet operations are further facilitated by the use of hydrophilic and/or hydrophobic regions on surfaces and/or by physical obstacles. For examples of droplet operations, see the patents and patent applications cited above under the definition of "droplet actuator."

"Filler fluid" means a fluid associated with a droplet operations substrate of a droplet actuator, which fluid is sufficiently immiscible with a droplet phase to render the droplet phase subject to electrode-mediated droplet operations. The filler fluid may, for example, be a low-viscosity oil, such as silicone oil. Other examples of filler fluids are provided in International Patent Application No. PCT/US2006/047486, entitled "Droplet-Based Biochemistry," filed on Dec. 11, 2006; International Patent Application No. PCT/US2008/072604, entitled "Use of additives for enhancing droplet actuation," filed on Aug. 8, 2008; and U.S. Patent Publication No. 20080283414, entitled "Electrowetting Devices," filed on May 17, 2007; the entire disclosures of which are incorporated herein by reference. The filler fluid may fill the entire gap of the droplet actuator or may coat one or more surfaces of the droplet actuator. Filler fluid may be conductive or non-conductive.

"Immobilize" with respect to magnetically responsive beads, means that the beads are substantially restrained in position in a droplet or in filler fluid on a droplet actuator. For example, in one embodiment, immobilized beads are sufficiently restrained in position to permit execution of a splitting operation on a droplet, yielding one droplet with substantially all of the beads and one droplet substantially lacking in the beads.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, CoONiO, $Mn_2O_3$, $Cr_2O_3$, and CoMnP.

"Transporting into the magnetic field of a magnet," "transporting towards a magnet," and the like, as used herein to refer to droplets and/or magnetically responsive beads within droplets, is intended to refer to transporting into a region of a magnetic field capable of substantially attracting magnetically responsive beads in the droplet. Similarly, "transporting away from a magnet or magnetic field," "transporting out of the magnetic field of a magnet," and the like, as used herein to refer to droplets and/or magnetically responsive beads within droplets, is intended to refer to transporting away from a region of a magnetic field capable of substantially attracting magnetically responsive beads in the droplet, whether or not the droplet or magnetically responsive beads is completely removed from the magnetic field. It will be appreciated that in any of such cases described herein, the droplet may be transported towards or away from the desired region of the magnetic field, and/or the desired region of the magnetic field may be moved towards or away from the droplet. Reference to an electrode, a droplet, or magnetically responsive beads being "within" or "in" a magnetic field, or the like, is intended to describe a situation in which the electrode is situated in a manner which permits the electrode to transport a droplet into and/or away from a desired region of a magnetic field, or the droplet or magnetically responsive beads is/are situated in a desired region of the magnetic field, in each case where the magnetic field in the desired region is capable of substantially attracting any magnetically responsive beads in the droplet. Similarly, reference to an electrode, a droplet, or magnetically responsive beads being "outside of" or "away from" a magnetic field, and the like, is intended to describe a situation in which the electrode is situated in a manner which permits the electrode to transport a droplet away from a certain region of a magnetic field, or the droplet or magnetically responsive beads is/are situated in away from a certain region of the magnetic field, in each case where the magnetic field in such region is not capable of substantially attracting any magnetically responsive beads in the droplet.

"Washing" with respect to washing a bead means reducing the amount and/or concentration of one or more substances in contact with the bead or exposed to the bead from a droplet in contact with the bead. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a starting droplet in contact with a magnetically responsive bead, where the droplet includes an initial amount and initial concentration of a substance. The washing operation may proceed using a variety of droplet operations. The washing operation may yield a droplet including the magnetically responsive bead, where the droplet has a total amount and/or concentration of the substance which is less than the initial amount and/or concentration of the substance. Examples of suitable washing techniques are described in Pamula et al., U.S. Pat. No. 7,439,014, entitled "Droplet-Based Surface Modification and Washing," granted on Oct. 21, 2008, the entire disclosure of which is incorporated herein by reference.

The terms "top," "bottom," "over," "under," and "on" are used throughout the description with reference to the relative positions of components of the droplet actuator, such as relative positions of top and bottom substrates of the droplet actuator. It will be appreciated that the droplet actuator is functional regardless of its orientation in space.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

6 BRIEF DESCRIPTION OF THE DRAWINGS

Figure 4A:
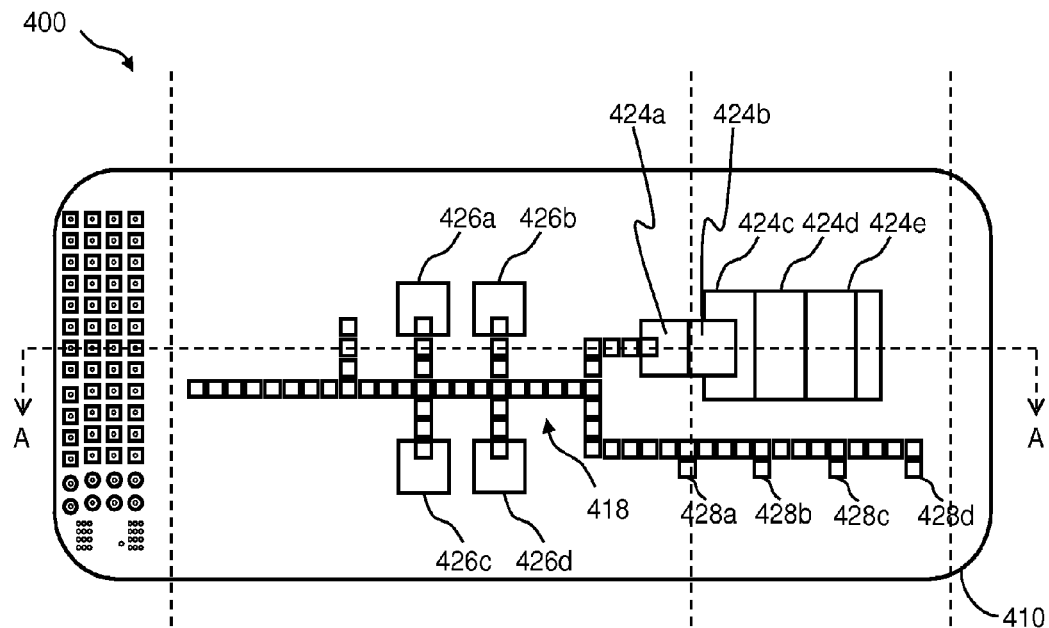
FIGS. 4A and 4B illustrate a top view and a cross-sectional view, respectively, of a droplet actuator and illustrate variations in gap height associated with certain droplet operation regions.
Figure 4B:
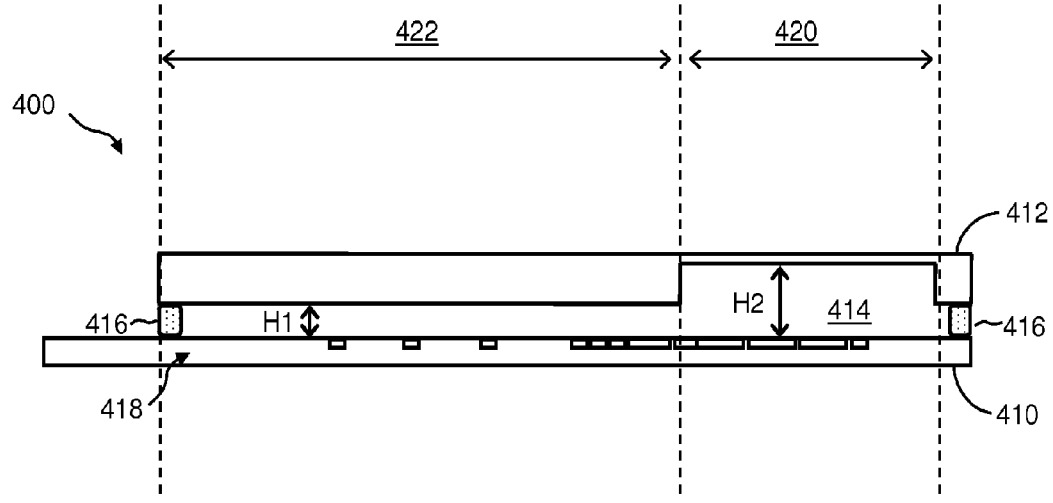
Figure 5A:
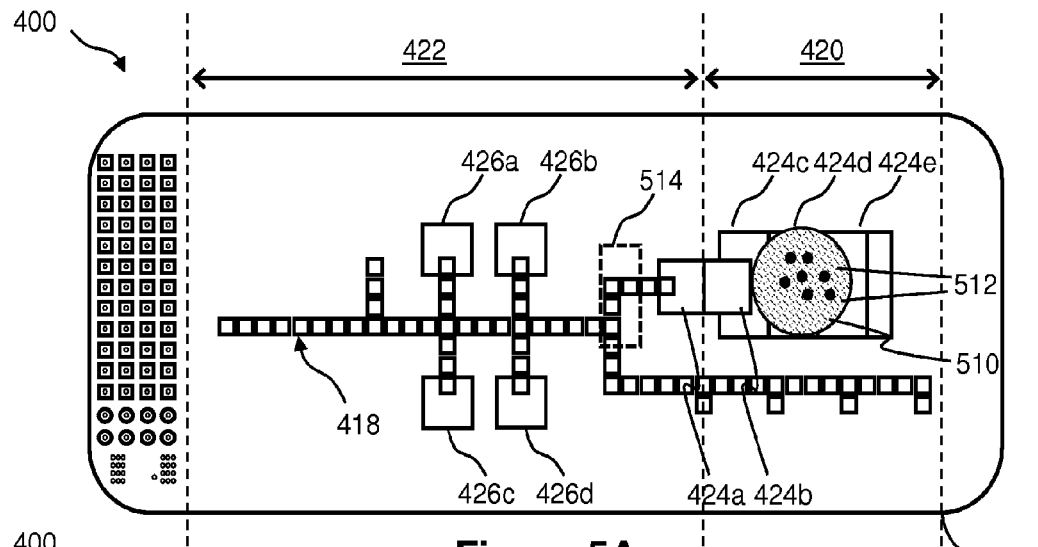
Figure 5B:
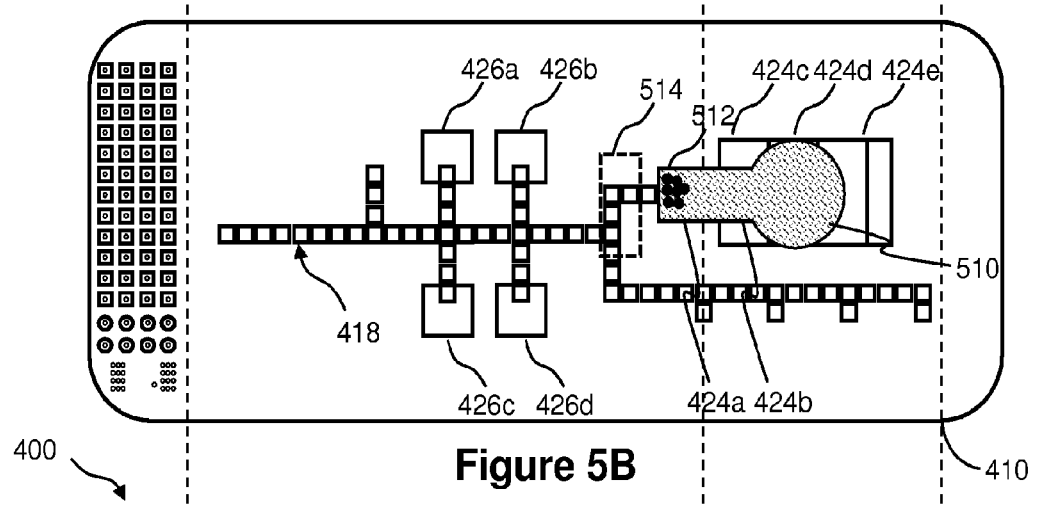
Figure 5C:
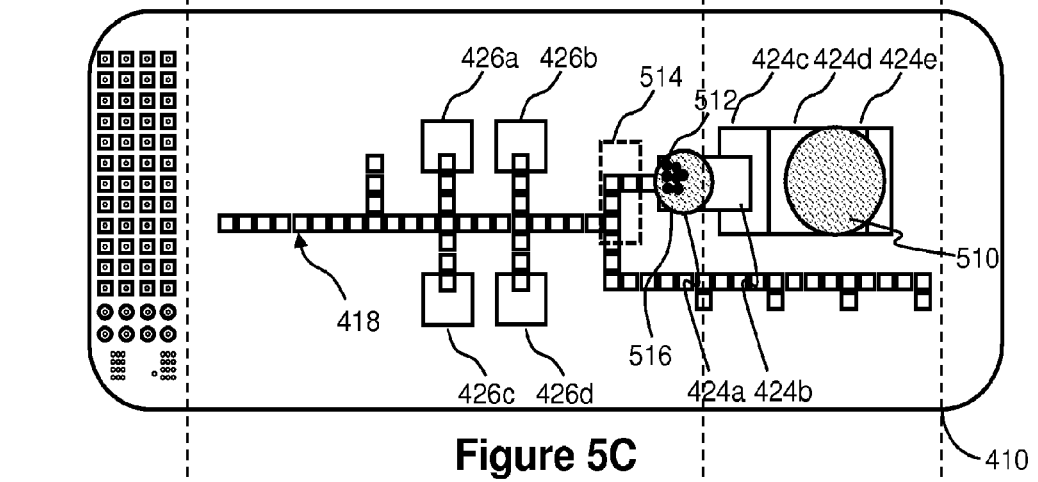
Figure 6A:
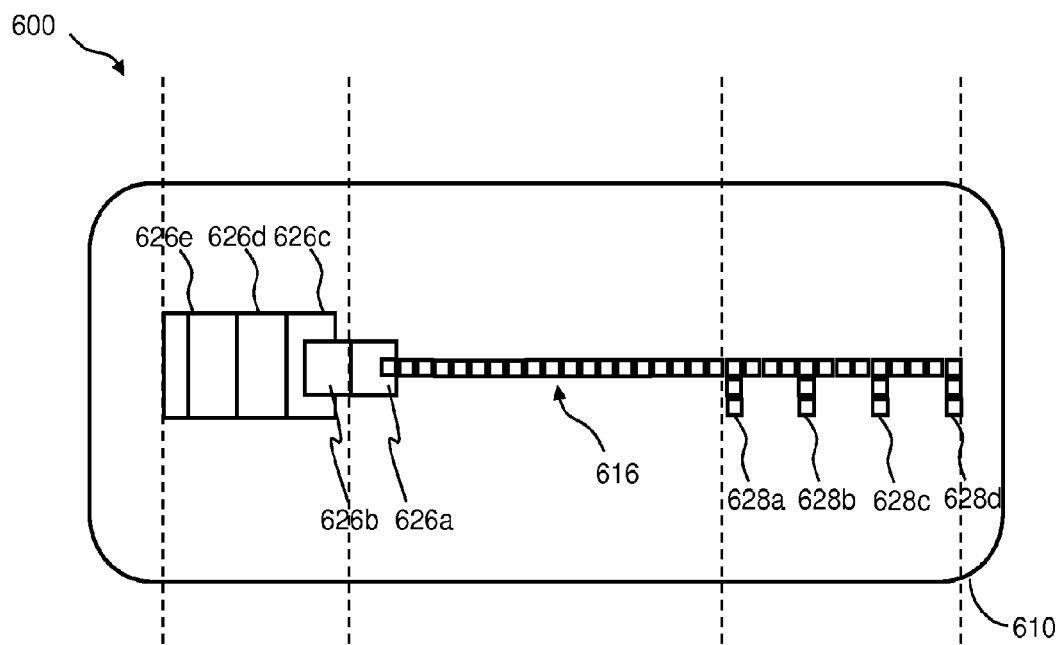
Figure 6B:
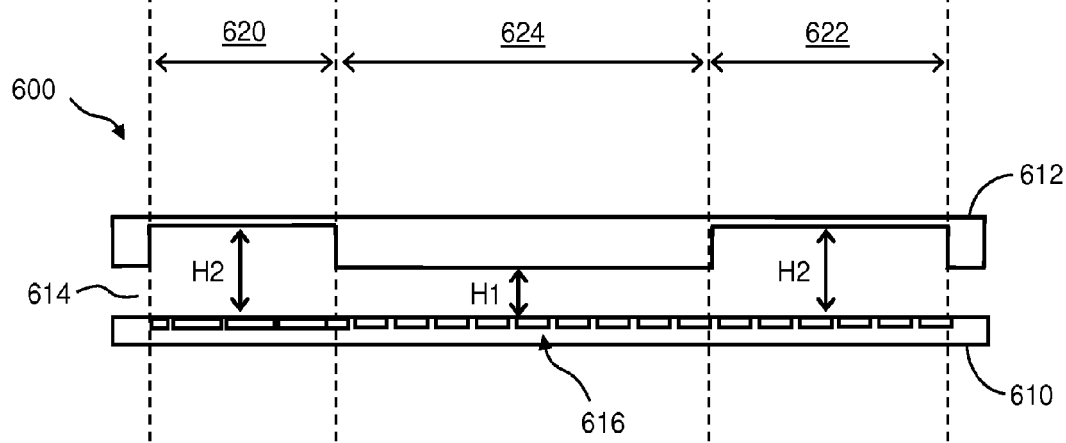
Figure 7A:
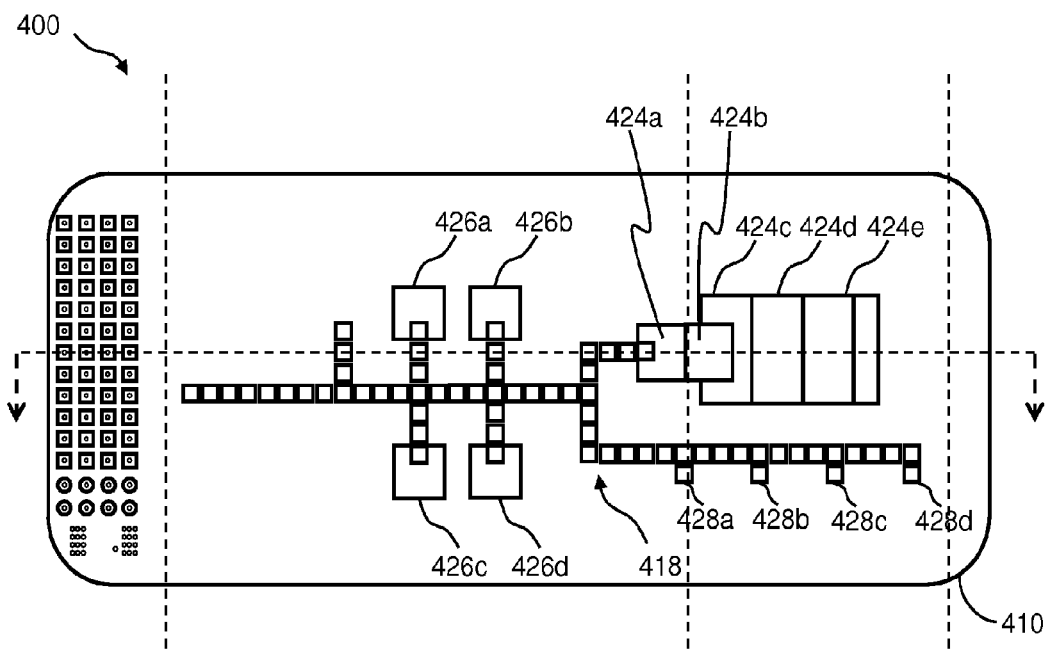
Figure 7B:
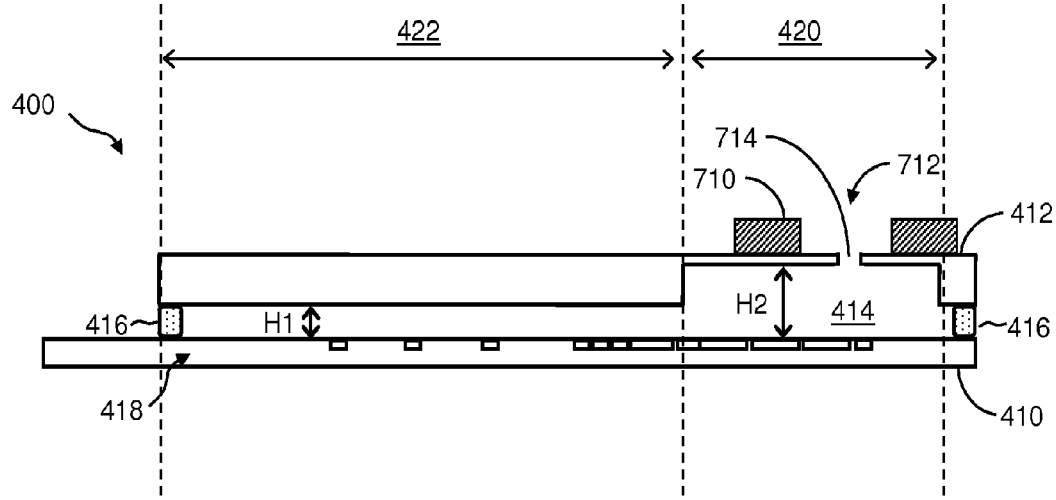
Figure 8:
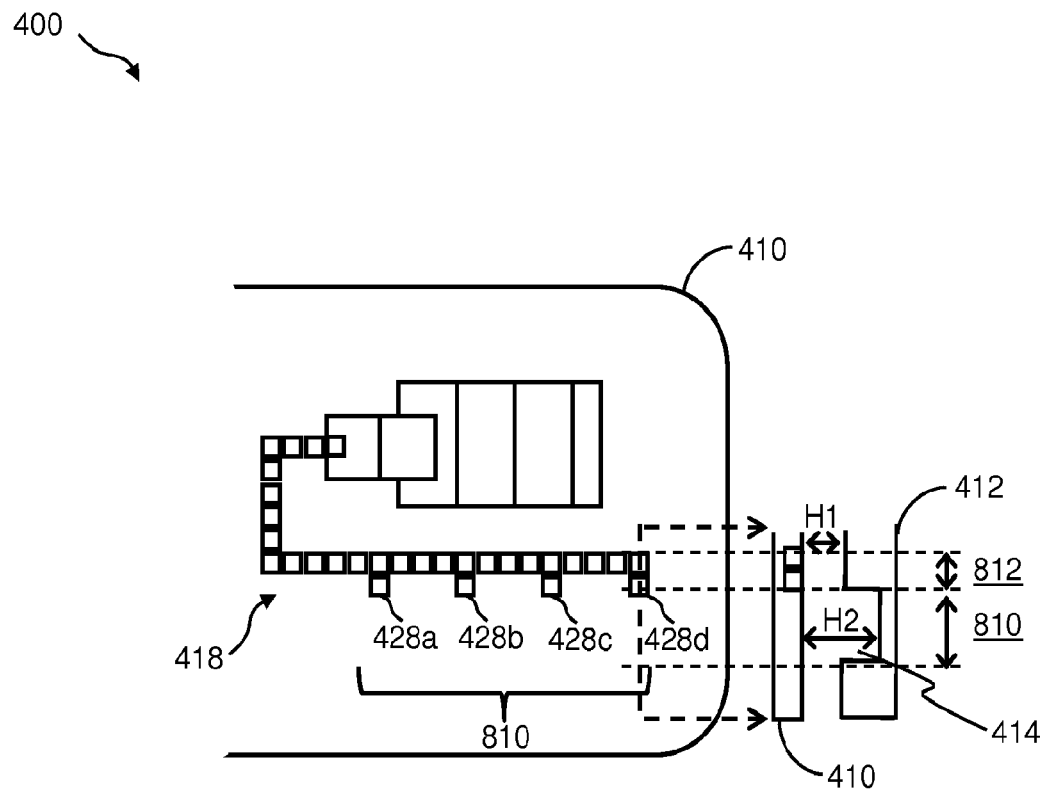
Figure 9A:
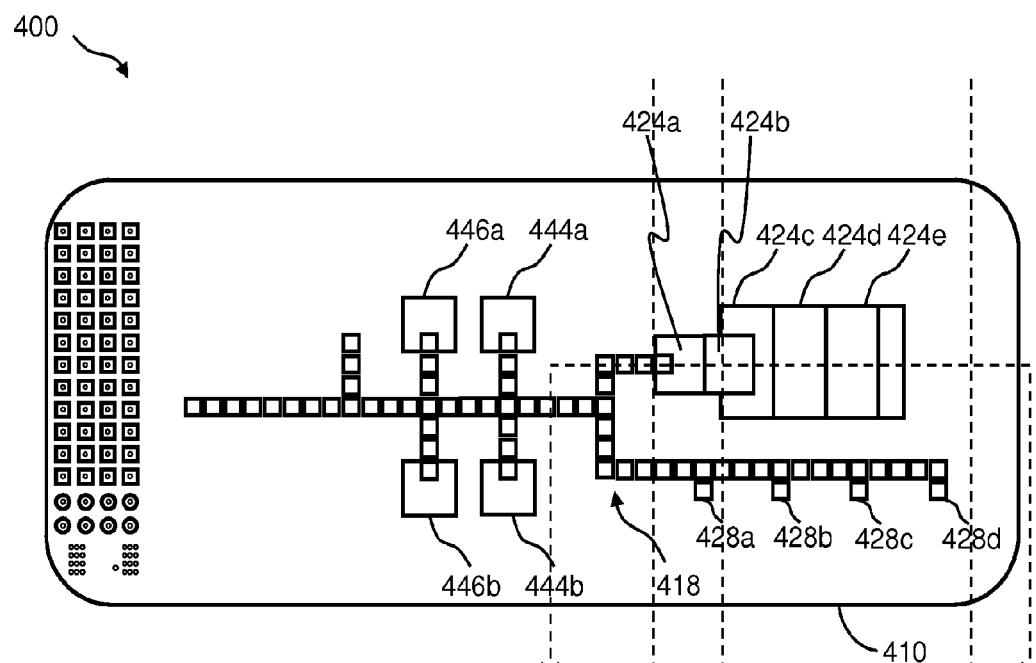
Figure 9B:
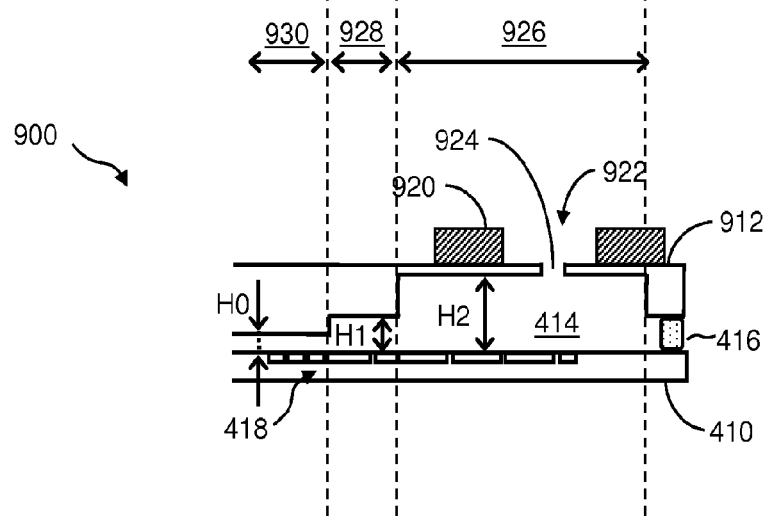
Figure 10:
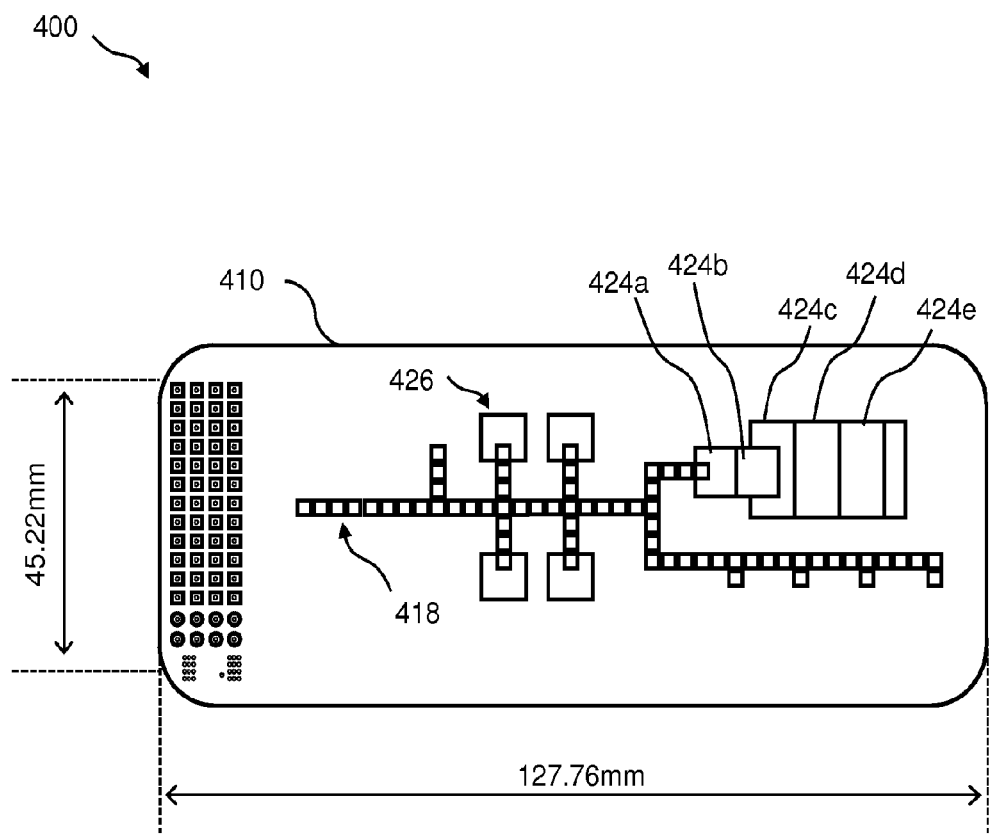
Figure 11A:
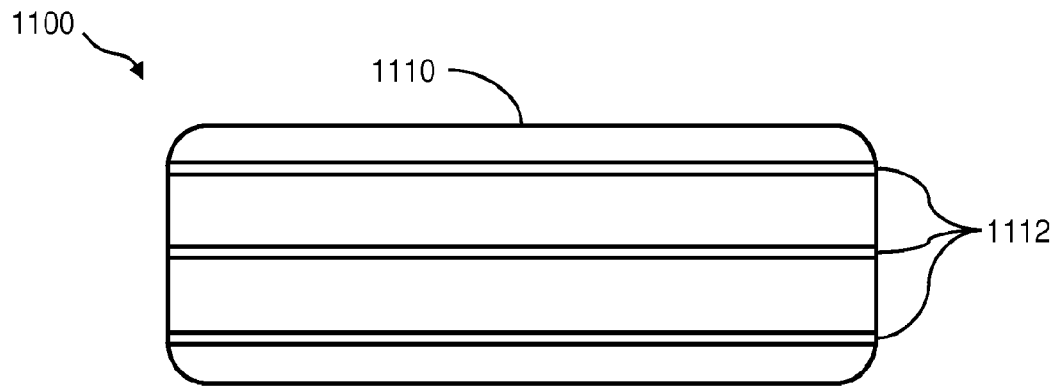
Figure 11B:
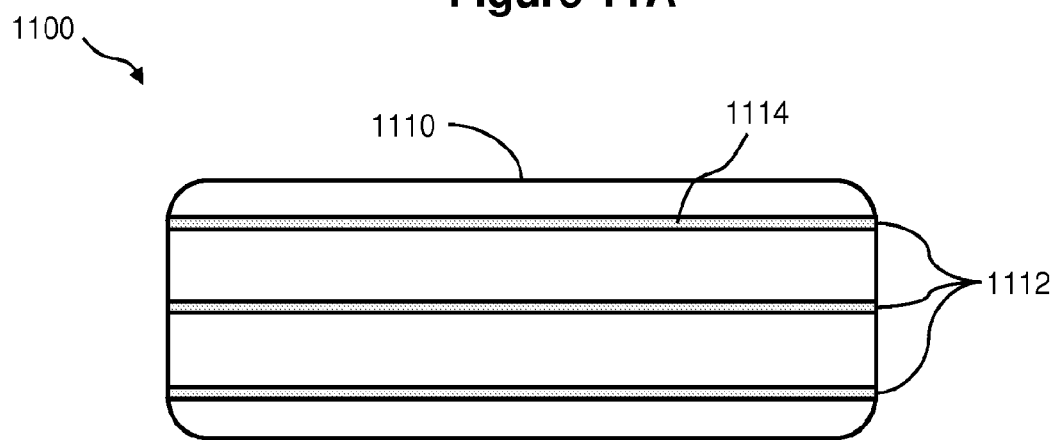
Figure 11C:
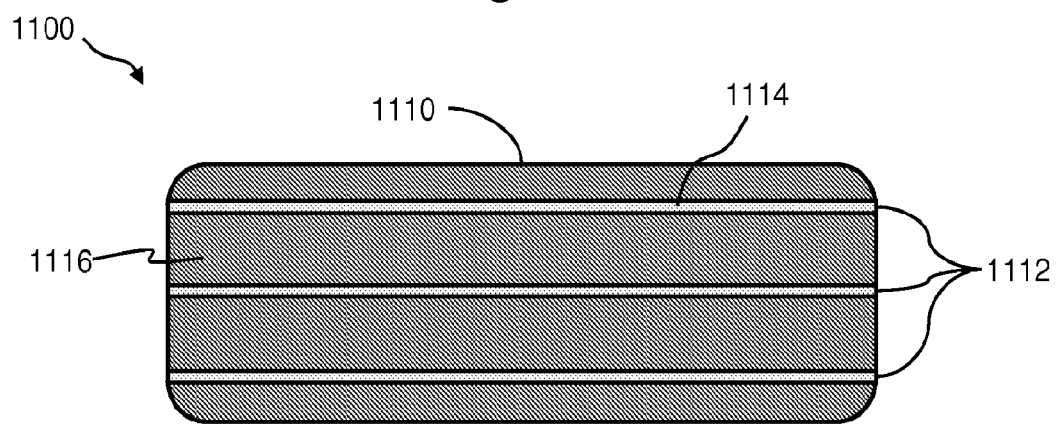
Figure 12A:
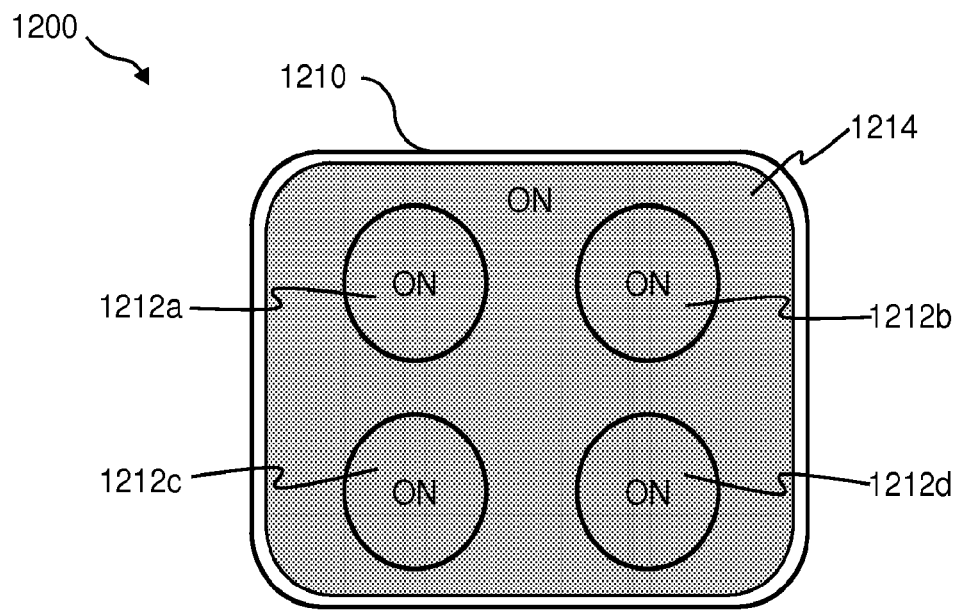
Figure 12B:
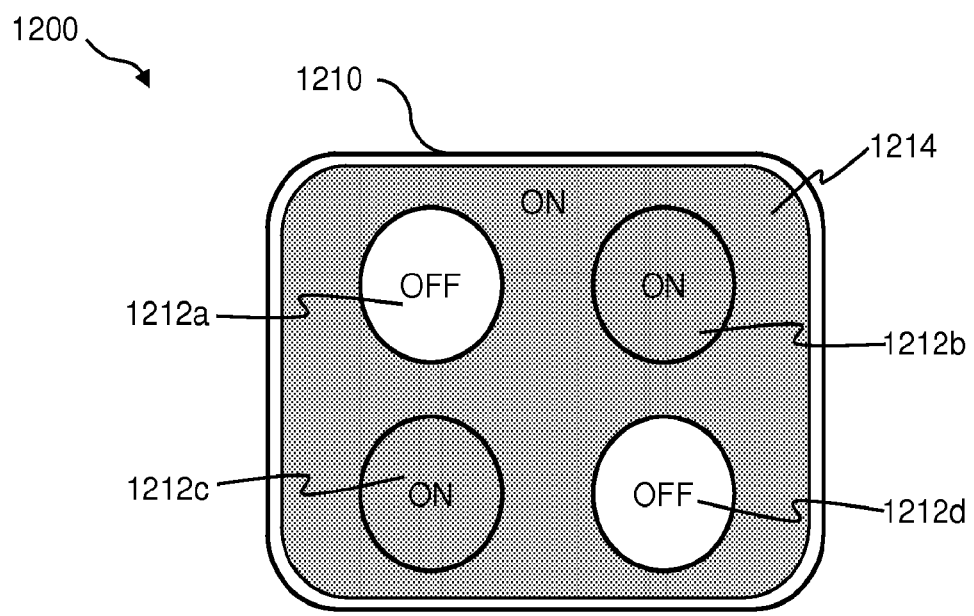
Figure 13:
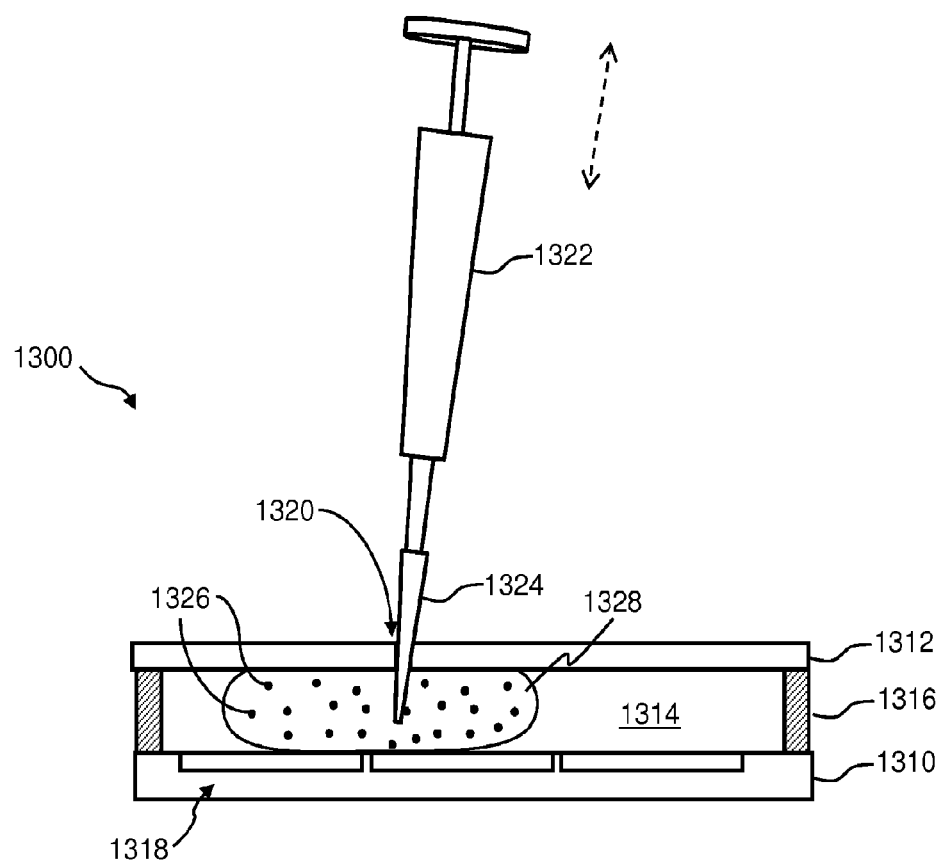
Figure 14:
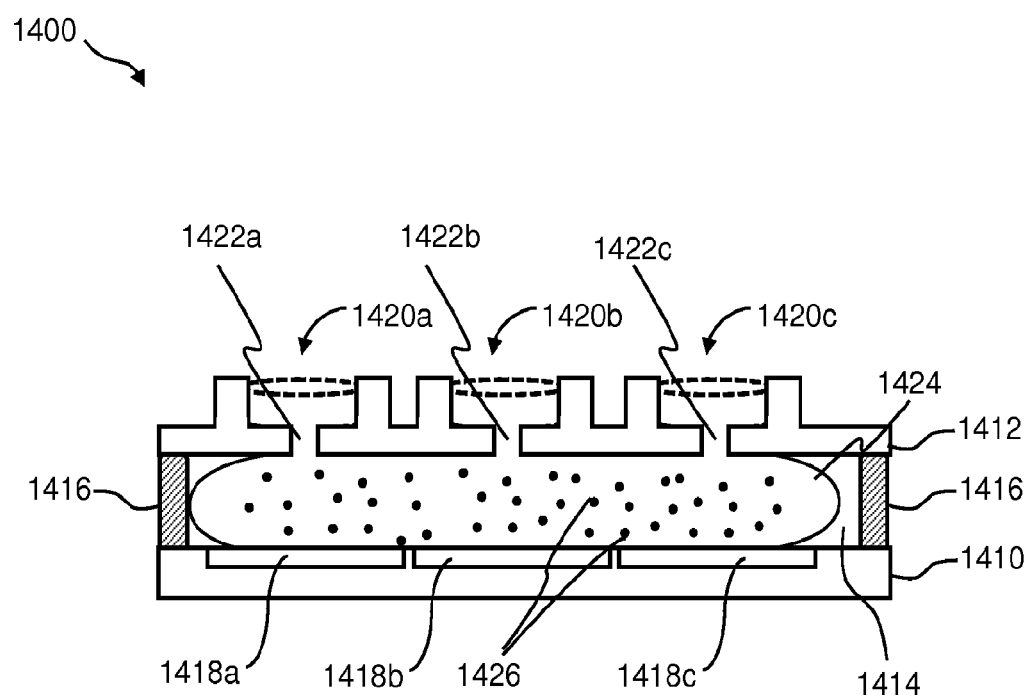
Figure 16A:
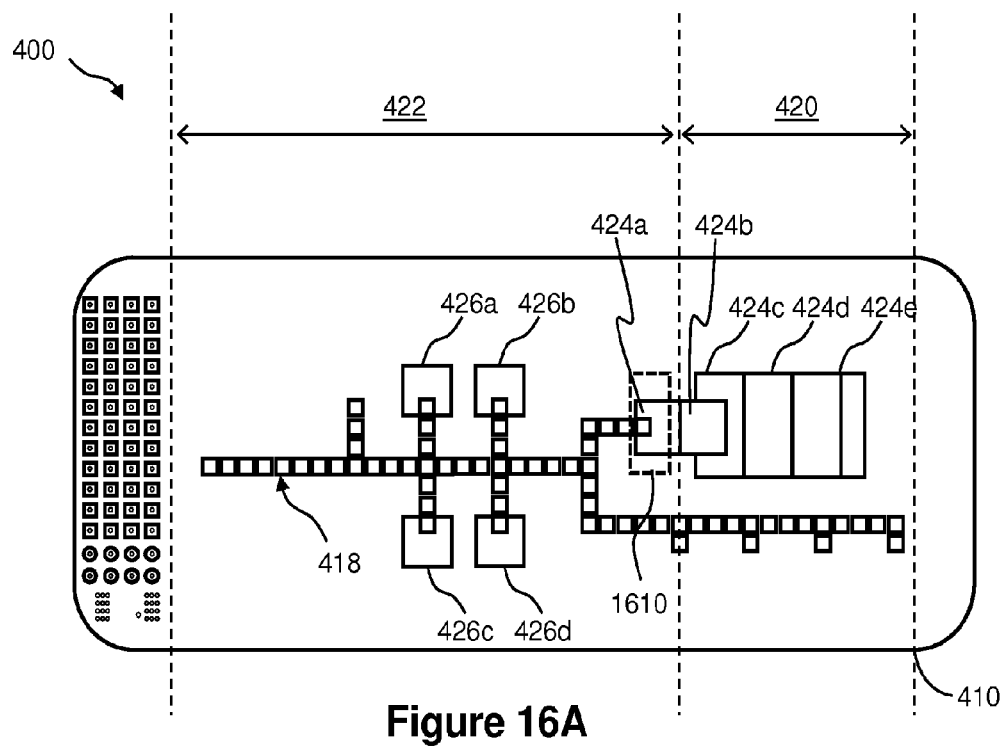
Figure 16B:
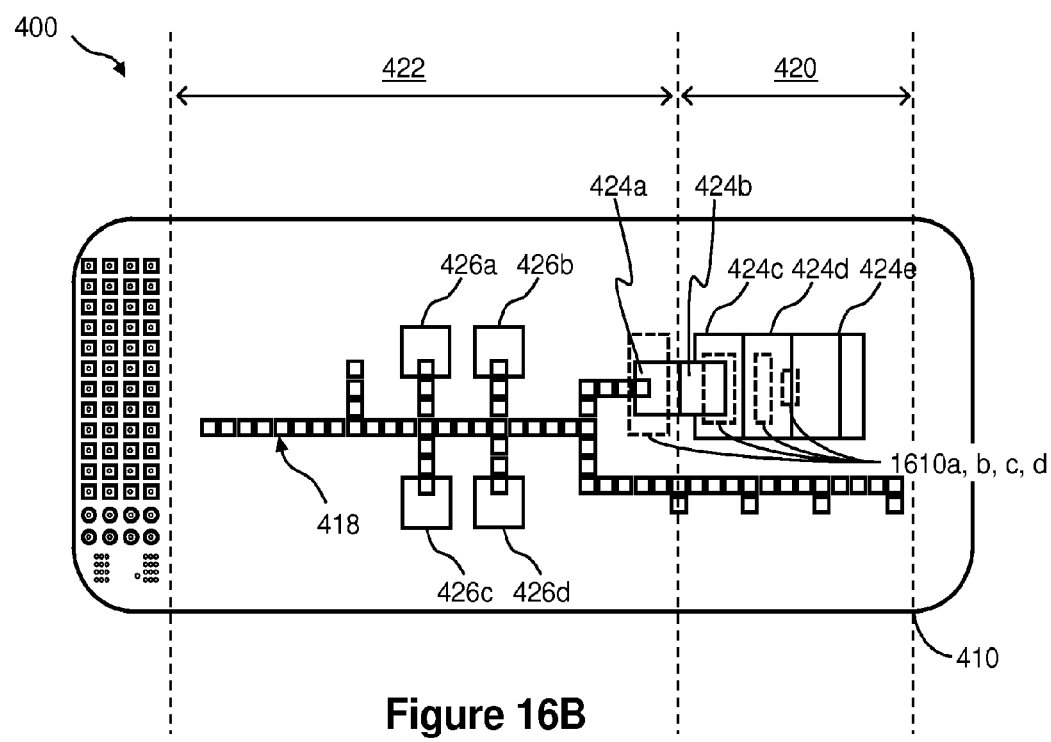
Figure 17:
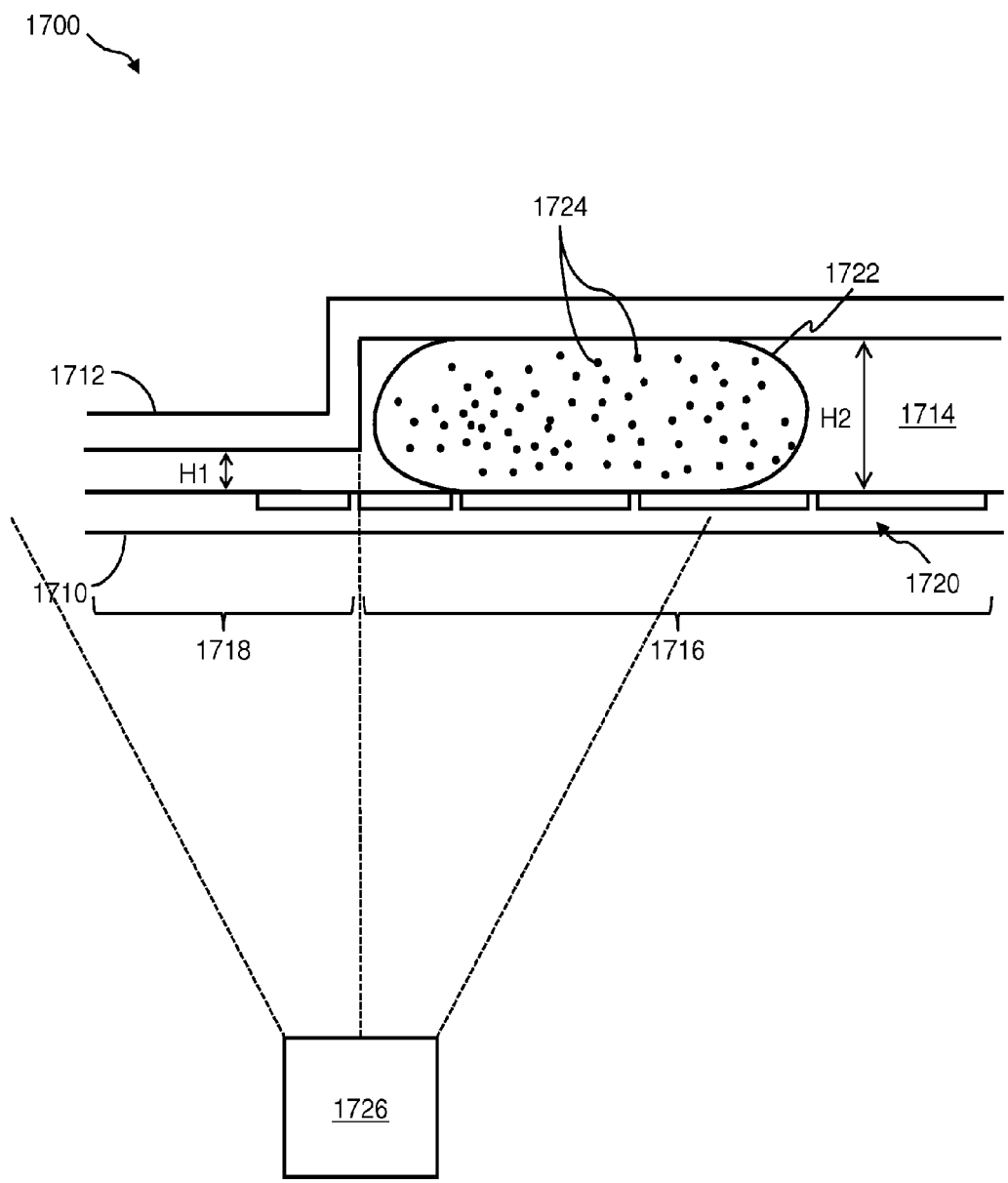
Figure 18A:
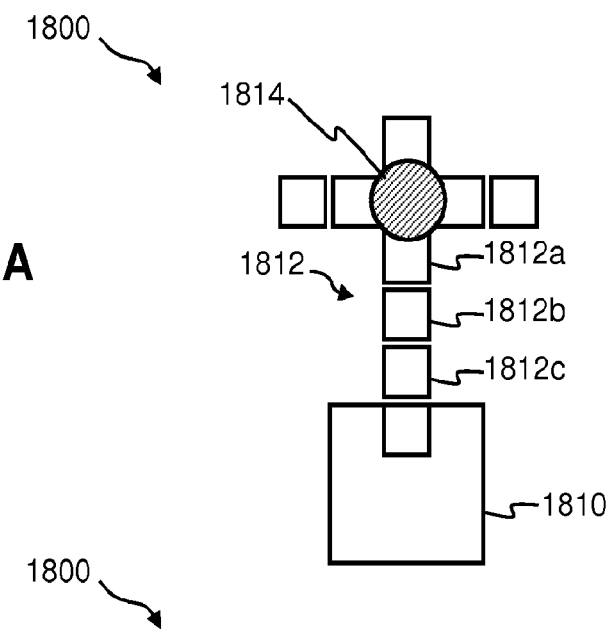
Figure 18B:
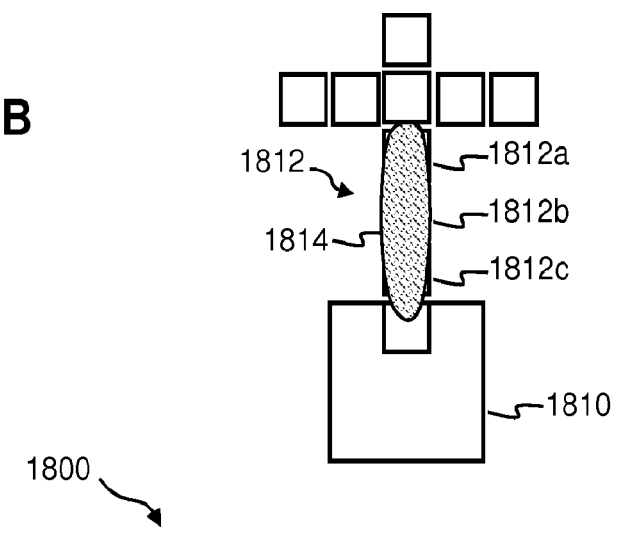
Figure 18C:
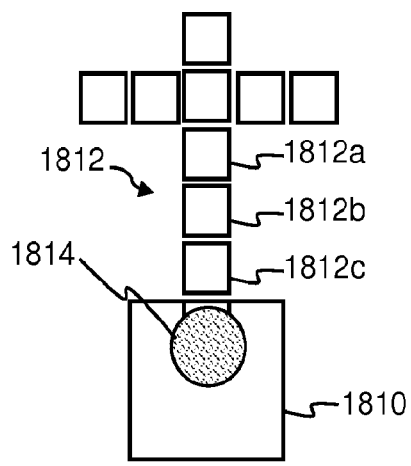
Figure 20A:
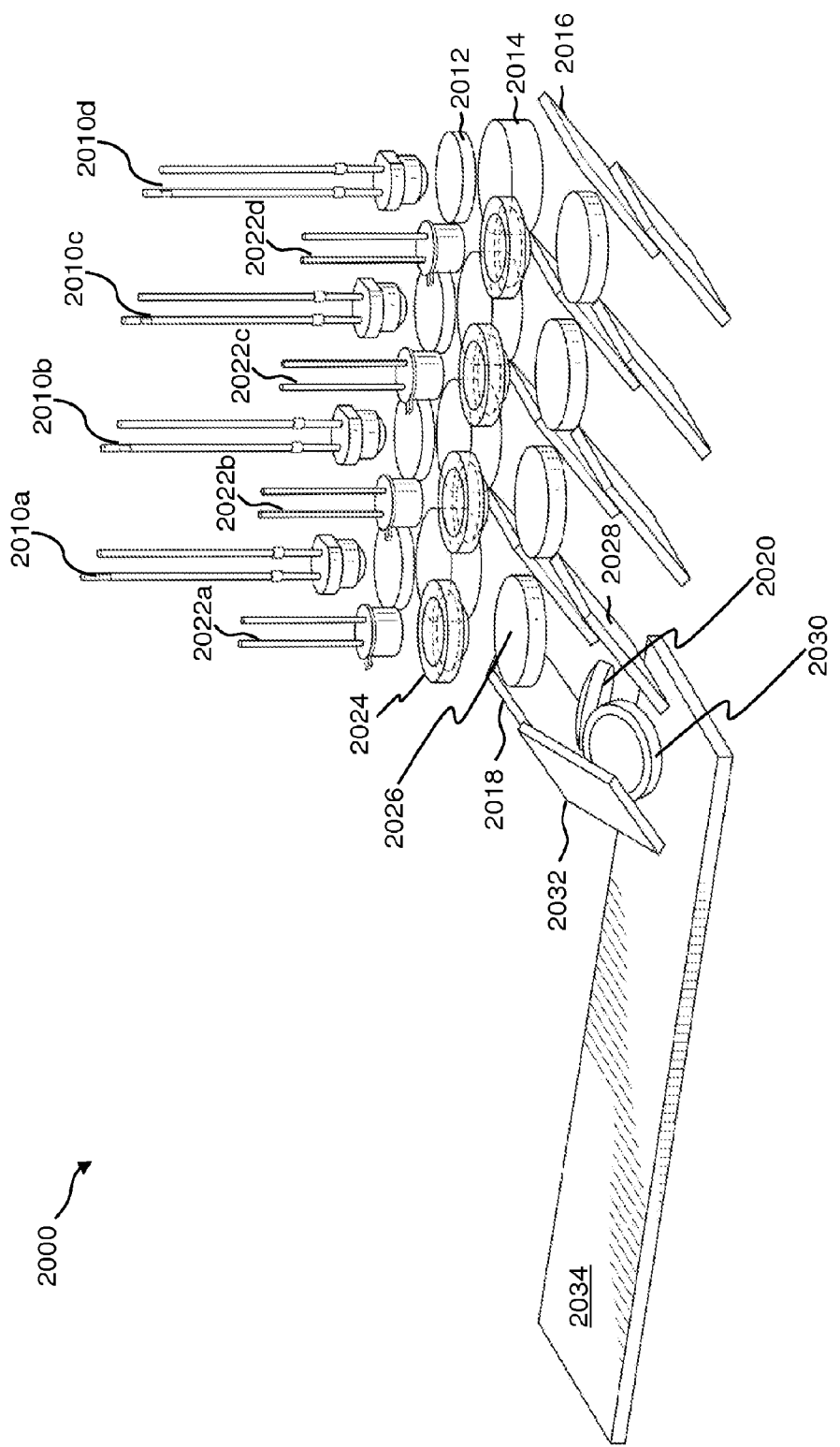
Figure 20B:
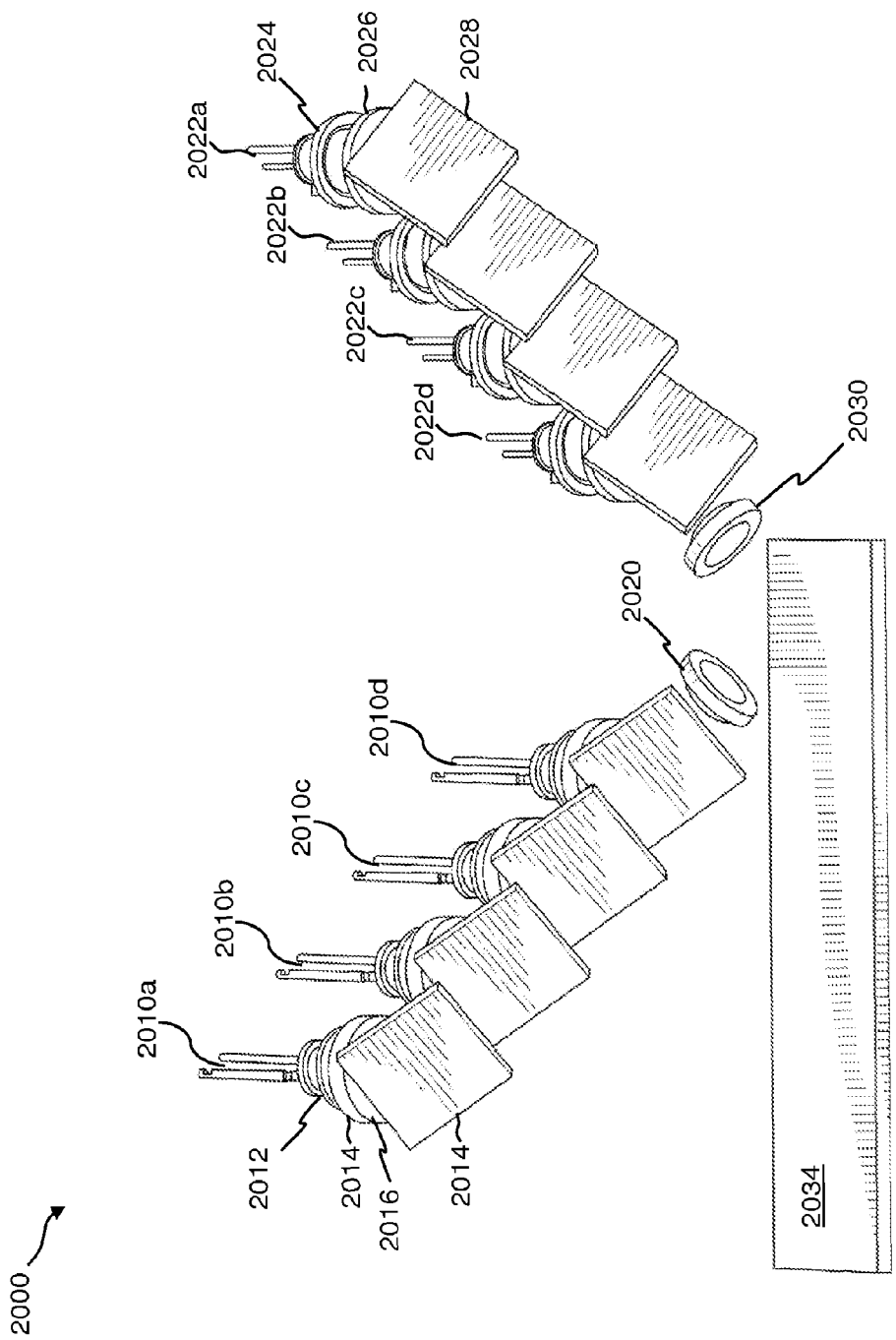
Figure 21:
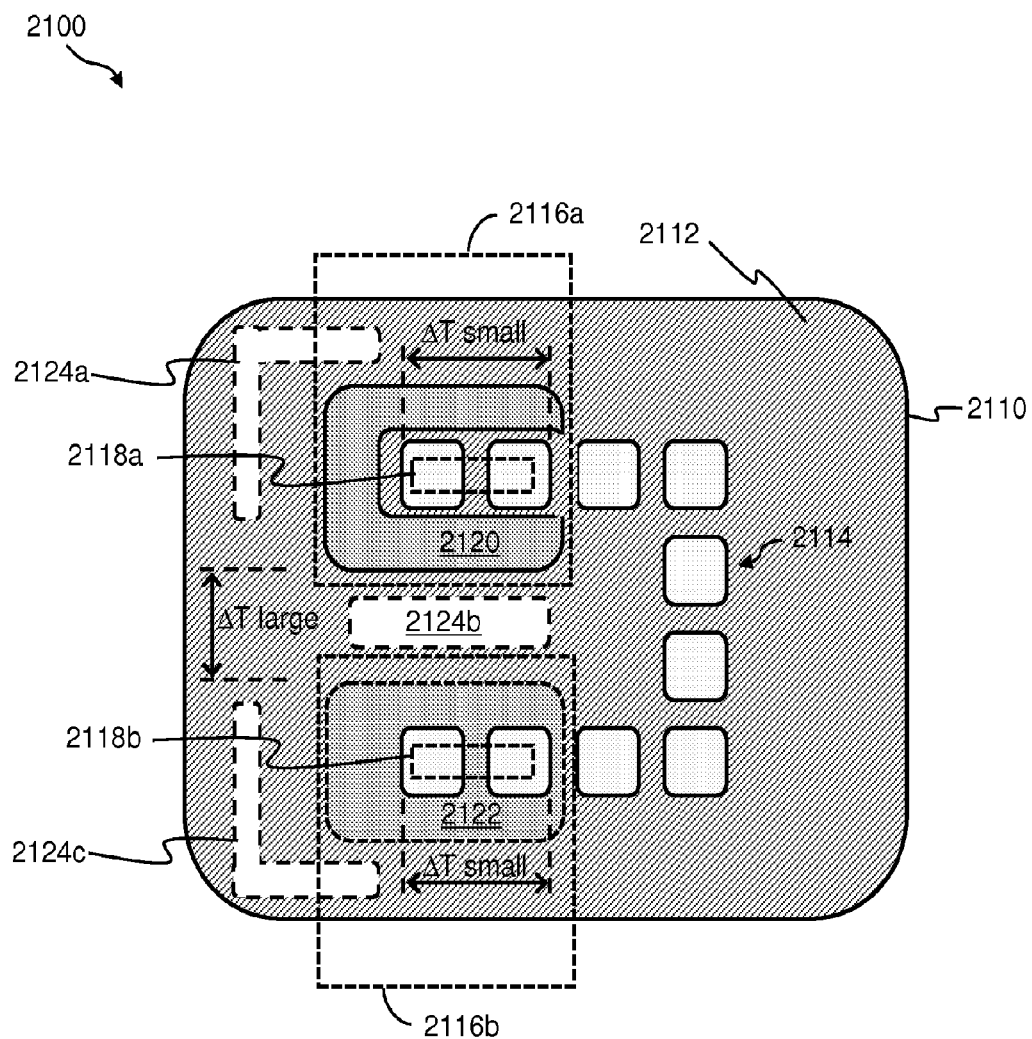
Figure 22A:
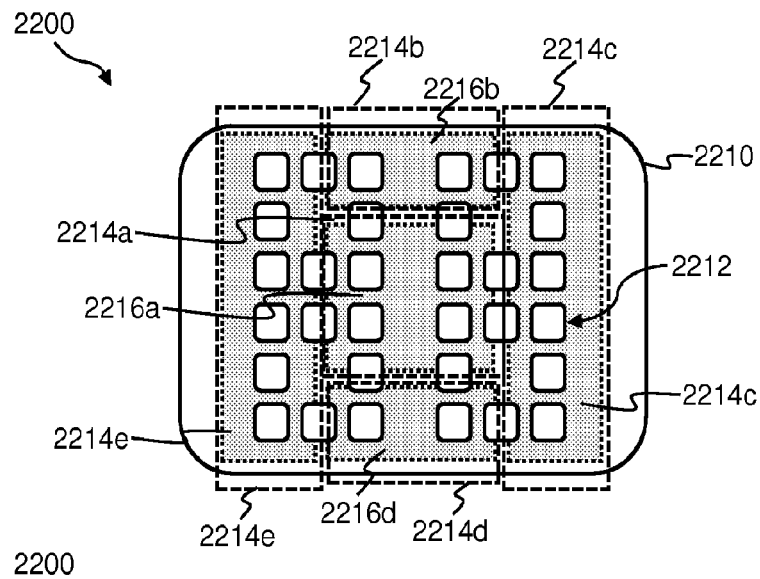
Figure 22B:
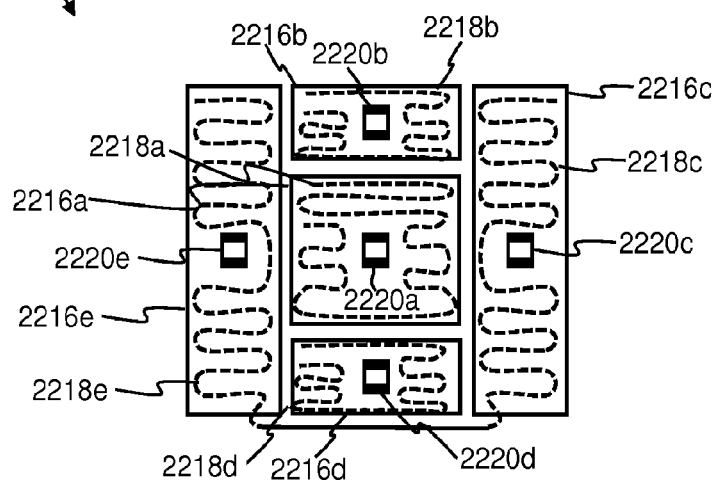
Figure 22C:
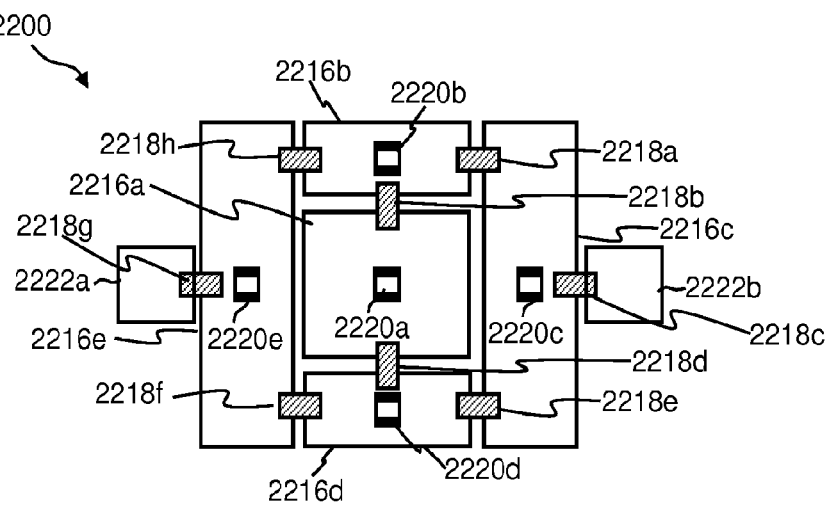
Figure 23A:
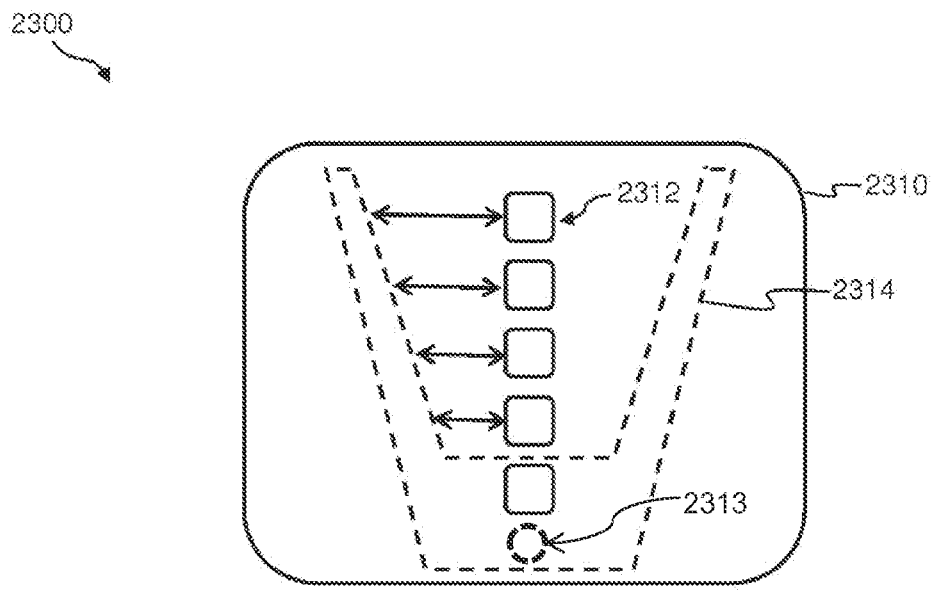
Figure 23B:
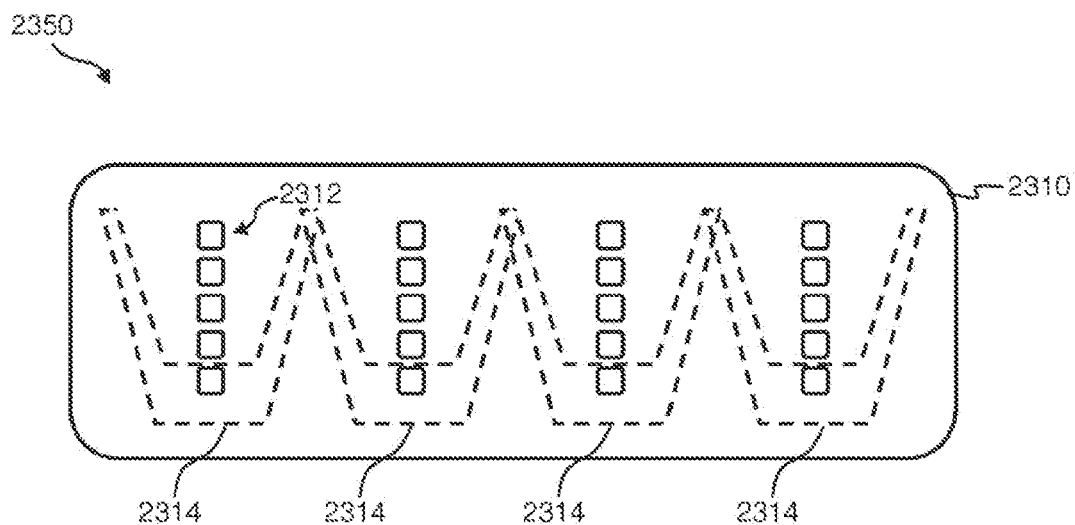
Figure 24:
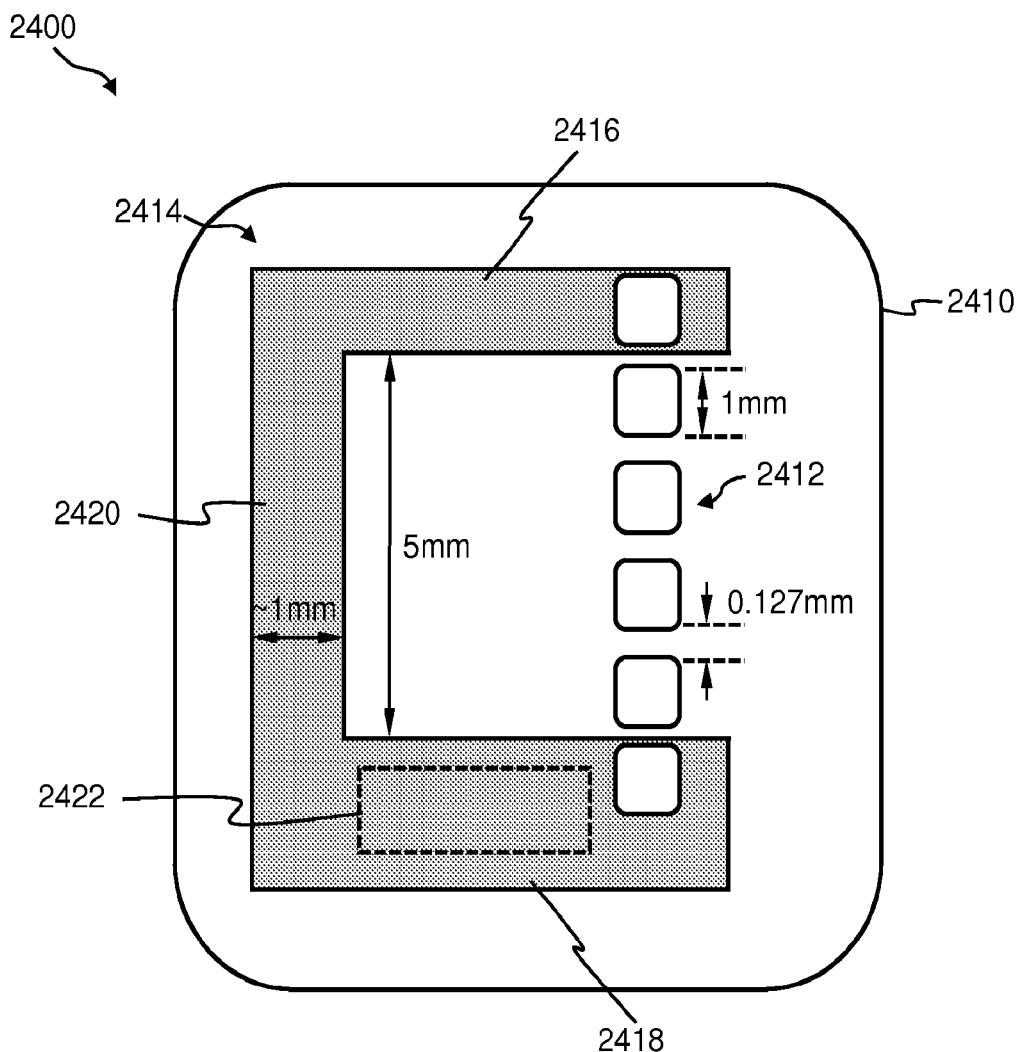
Figure 25:
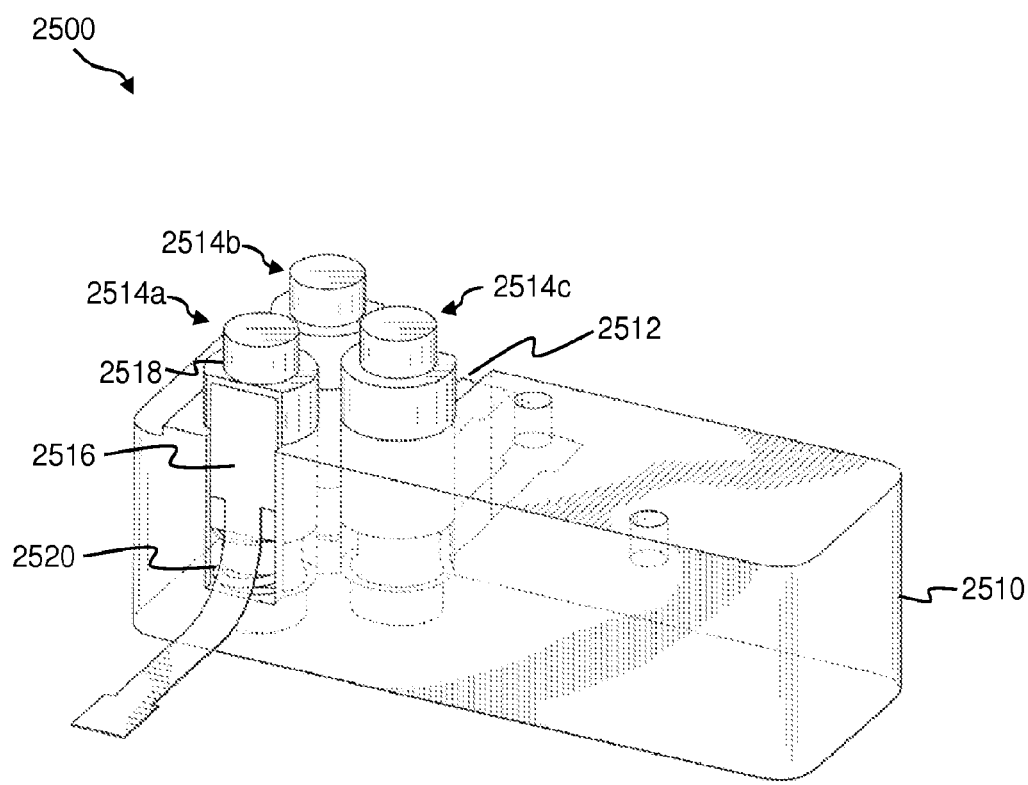
Figure 26:
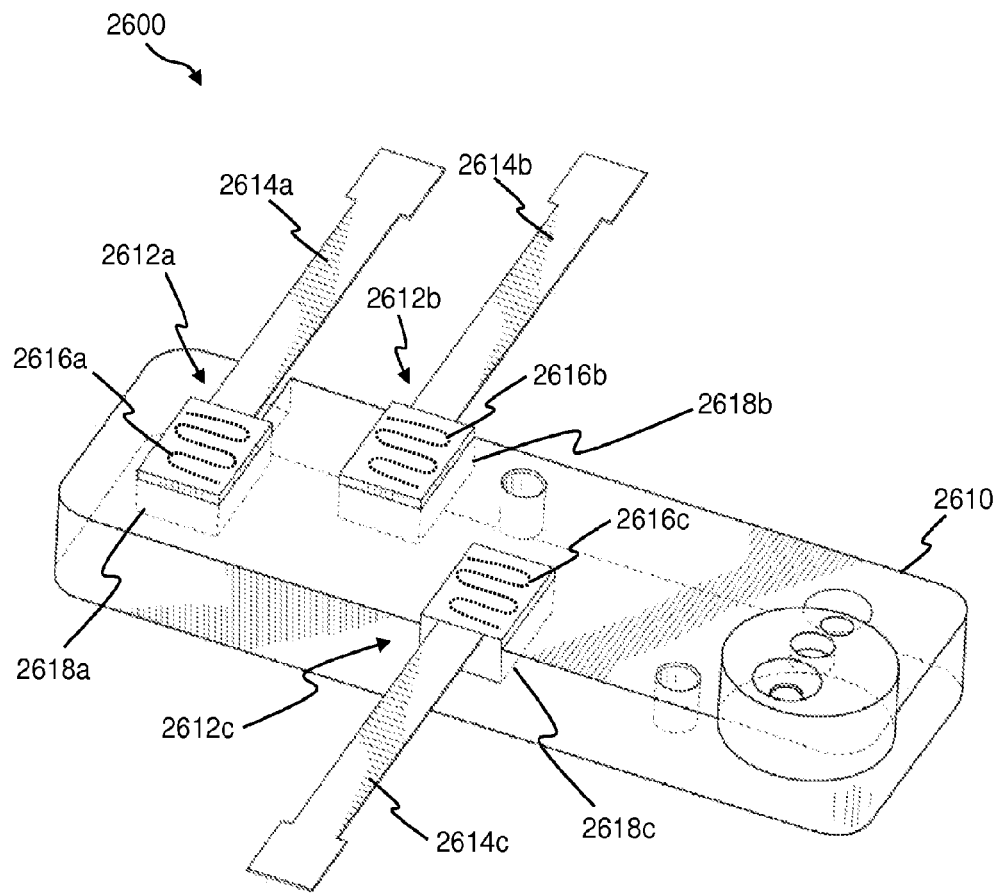
Figure 27A:
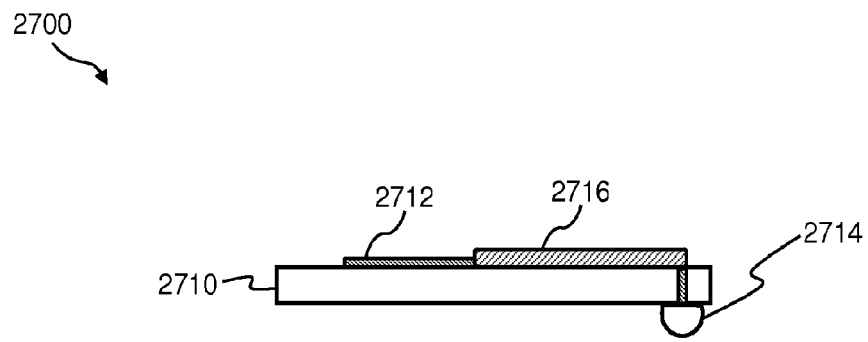
Figure 27B:
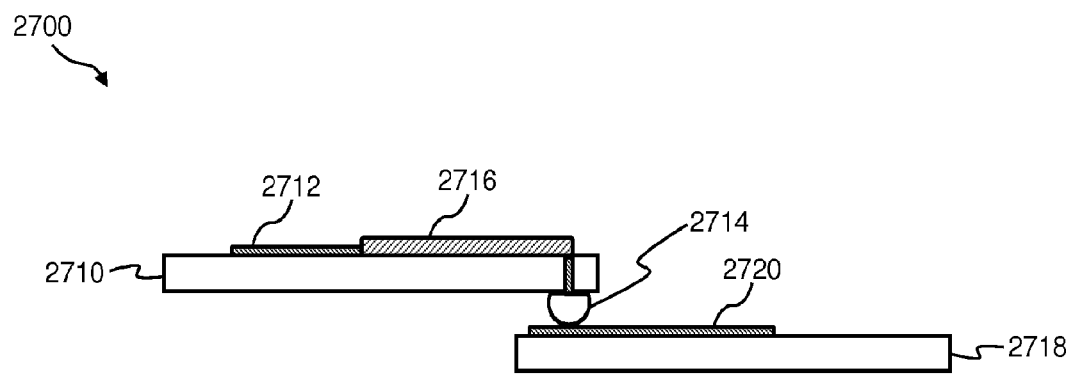
Figure 28:
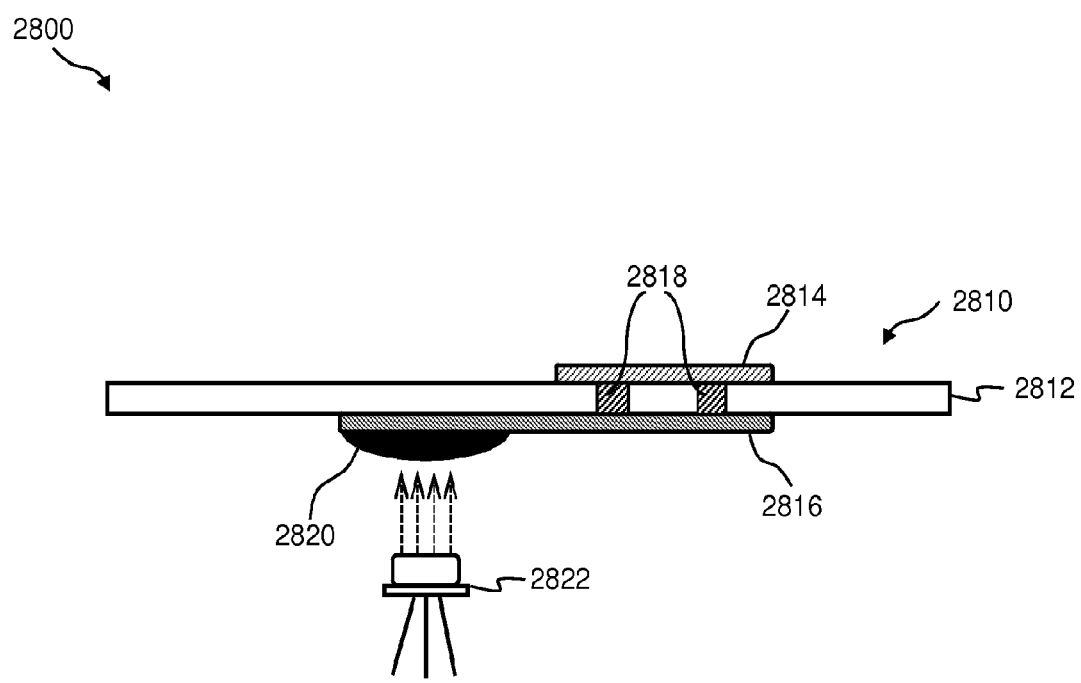

FIGS. 5A, 5B, and 5C illustrate other top views of the droplet actuator of FIGS. 4A and 4B and show a process of concentrating and dispensing magnetically responsive beads from a large sample volume;

FIGS. 6A and 6B illustrate a top view and a side view, respectively, of a droplet actuator and illustrate variations in gap height associated with sample storage and waste disposal regions;

FIGS. 7A and 7B illustrate another top view and side view, respectively, of the droplet actuator of FIGS. 4A and 4B and illustrate another example of a two-step droplet actuator configured for integrated sample-to-result analysis of a single biological sample;

FIG. 8 illustrates yet another side view of a portion of the droplet actuator of FIGS. 4A and 4B and illustrates the interface between droplet operations and waste disposal regions where the gap height transitions from H1 to H2;

FIGS. 9A and 9B illustrate yet another top view and side view, respectively, of the droplet actuator of FIGS. 4A and 4B and illustrate an example of a three-step droplet actuator configured for integrated sample-to-result analysis of a single biological sample;

FIG. 10 illustrates yet another top view of the droplet actuator of FIGS. 4A and 4B and illustrates an example of suitable dimensions of certain droplet operations regions on a droplet actuator;

FIGS. 11A through 11C illustrate top views of an electrode arrangement and show a process for mixing a small volume of fluid with a larger volume of fluid;

FIGS. 12A and 12B illustrate top views of an electrode arrangement and show another process for mixing a larger volume of fluid;

FIG. 13 illustrates a side view of an example of an on-actuator sample reservoir of a droplet actuator and illustrates a method of mixing large volumes of liquid with smaller volumes of reagents;

FIG. 14 illustrates a side view of an example of a portion of a droplet actuator and illustrates another method of mixing a larger volume of fluid with a smaller volume of fluid;

FIG. 15 illustrates a side view of a portion of a droplet actuator and illustrates another method of mixing a large volume of fluid in a droplet actuator;

FIGS. 16A and 16B illustrate yet other top views of the droplet actuator of FIGS. 4A and 4B and illustrate the arrangement of one or more magnets that may be used to concentrate and collect a quantity of magnetically responsive beads from a large sample volume;

FIG. 17 illustrates a side view of a portion of a droplet actuator that includes a strong magnet positioned a certain distance away from the bottom surface of the droplet actuator;

FIGS. 18A through 18C illustrate top views of an electrode arrangement of a portion of a droplet actuator and illustrate a process of transporting a small droplet onto a reservoir electrode;

FIGS. 19A through 19D illustrate side views of a portion of a droplet actuator and illustrate methods for containing the sample space of an on-actuator reservoir;

FIGS. 20A and 20B illustrate perspective views of two example embodiments of a detection system for detection of multiple (e.g., four) different fluorophores at a single detection spot;

FIG. 21 illustrates a top view of an example of a portion of a droplet actuator and illustrates methods for controlling the flow of heat in certain regions (temperature control zones) of a droplet actuator;

FIGS. 22A, 22B, and 22C illustrate top views of an example of a portion of a droplet actuator and illustrate methods for co-locating temperature control zones and associated heat spreaders on a droplet actuator;

FIG. 23A illustrates a top view of an example of a portion of a droplet actuator and illustrate a method for forming a temperature gradient along a path of droplet operations electrodes;

FIG. 23B illustrates a top view of an example of a portion of a droplet actuator that includes an arrangement of multiple heat spreaders of FIG. 23A;

FIG. 24 illustrates a top view of an example of a portion of a droplet actuator and illustrates another method for forming a temperature gradient along a path of droplet operations electrodes;

FIG. 25 illustrates a perspective view of a resistive heating device that includes resistive heaters mounted to spring-loaded metallic conductors;

FIG. 26 illustrate a perspective view of another example of a heating device, wherein the heating device includes one or more flex heater assemblies;

FIGS. 27A and 27B illustrate side views of an example of a portion of an electrowetting effector board configured for generation of resistive heat and illustrate the alignment of the effector board with a microfluidic chip for resistive heat transfer;

FIG. 28 illustrates a side view of an example of a portion of a droplet actuator that is configured for radiative heat transfer to a temperature control zone on a droplet actuator;

FIG. 29A illustrates an example of a portion of a droplet actuator for controlling the temperature of a droplet by position dithering;

FIG. 29B illustrates a schematic diagram of an example of a thermal circuit for the droplet actuator of FIG. 29A that is configured for position dithering; and FIG. 29C illustrates a schematic view of an example of an electrical equivalent circuit for position dithering used for droplet temperature control on the droplet actuator of FIG. 29A.

7 DETAILED DESCRIPTION OF THE INVENTION

The invention relates to a droplet actuator device and methods for integrated sample preparation and analysis of a liquid sample, such as a biological sample. The droplet actuator device and methods of the invention perform sample preparation and analysis from a single sample on the same droplet actuator. The droplet actuator device uses a large input sample volume (e.g., about 1 milliliter (mL)) and provides for rapid capture and concentration of target analytes for subsequent molecular diagnostic assays (e.g., qPCR, immunoassay).

In one embodiment, the droplet actuator device and methods of the invention provide for increased droplet throughput for rapid sample preparation and analysis. In one example, increased droplet throughput is provided by manipulation of larger sized droplets.

In another embodiment, the droplet actuator device and methods of the invention provide for efficient and controllable loading (e.g., reliable loading) of a large sample volume (e.g., about 1 mL) into a droplet actuator. In one example, reliable loading is provided by loading the sample in an on-actuator reservoir (on-actuator meaning in the droplet operations gap or on the droplet operations surface). In one embodiment, the reservoir into which the sample is loaded is in the droplet operations gap, and is specifically not a reservoir outside the droplet operations gap, such as a reservoir situated in the top substrate.

In another embodiment, the droplet actuator device and methods of the invention provide for effective mixing of analyte capture beads within a sample. In one example, electrowetting may be used to mix a sample stored in an on-actuator reservoir, e.g., by shuttling the droplet back and forth within the on-actuator reservoir.

In another embodiment, the droplet actuator device and methods of the invention provide for rapid and efficient concentration and collection of analyte capture beads, e.g., magnetically responsive capture beads. One or more magnets may be arranged in proximity of a sample stored in an on-actuator reservoir. The magnet may, for example, be stationary or moveable, permanent or electrically controllable, or any combination of the foregoing.

In yet another embodiment, the invention provides a detection system that uses a single excitation beam and a single detection beam to collect multiple (e.g., four) different fluorescent signals at a single detection spot on a droplet actuator.

In yet another embodiment, the invention provides methods for controlling heat distribution within a droplet operations gap. Similarly, the invention provides methods for controlling heat distribution within a filler fluid in a droplet operations gap. Similarly, the invention provides methods for controlling heat distribution within an oil filler fluid, such as low viscosity oil, such as silicone oil, in a droplet operations gap. The methods may minimize thermal losses in one or more temperature control zones on a droplet actuator. The thermal control aspect of the invention permits heat to be generated off-actuator (exterior to the droplet operations gap and off of the droplet operations surface), and transferred to a designated temperature control zones on a droplet actuator. In yet another embodiment, the invention provides methods for controlling the temperature of a droplet by transporting the droplet from one temperature region to another temperature region (position dithering) on a droplet actuator.

7.1 Droplet Actuator Devices

Figure 1A:
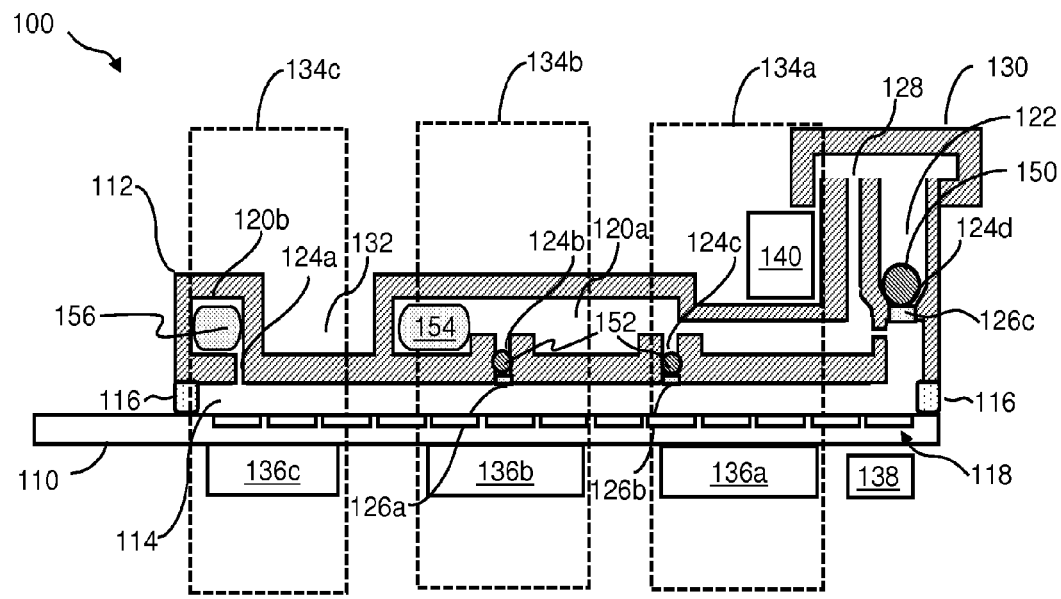
FIGS. 1A and 1B illustrate a side view and a top view, respectively, of a droplet actuator configured for sample-to-result analysis of a single biological sample.
Figure 1B:
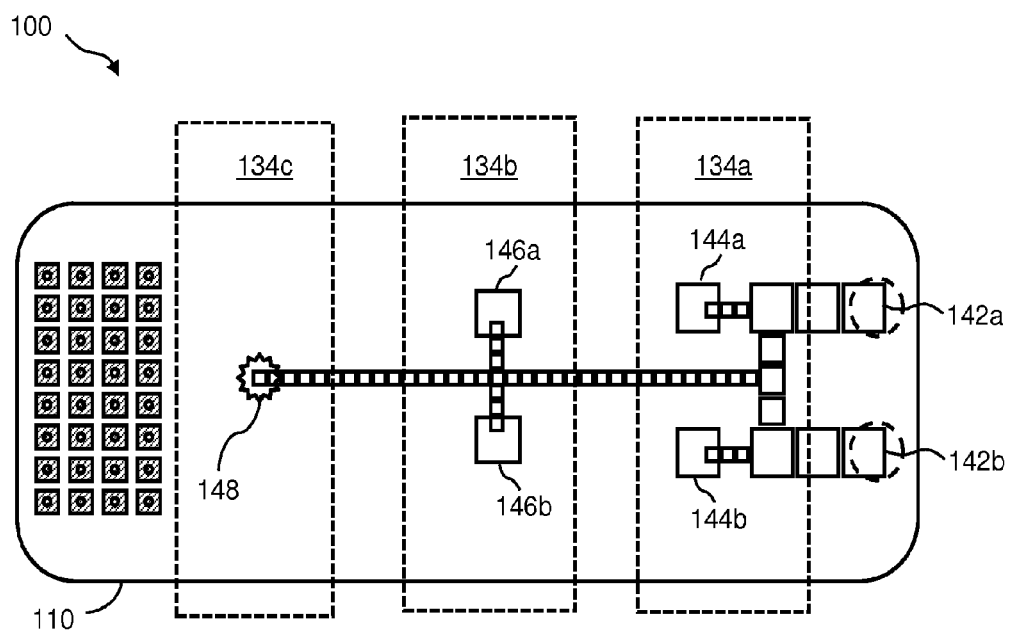

FIGS. 1A and 1B illustrate a side view and a top view, respectively, of a droplet actuator 100 configured for sample-to-result analysis of a single biological sample. In one embodiment, droplet actuator 100 is configured for integrated sample preparation and PCR analysis of a single sample for the presence and/or quantity of a nucleic acid analyte. In another embodiment, droplet actuator 100 is configured for integrated sample preparation and immunoassay analysis of a single sample.

Droplet actuator 100 may include a bottom substrate 110 and a top substrate 112 that are separated by a gap 114. A gasket 116 may be used to provide a seal around the outer edge of droplet actuator 100. Gasket 116 (as well as other gaskets described herein) may, for example, be formed of a polymeric substance, such as a polymeric gasket material, and/or an adhesive. Examples of suitable adhesives include UV curable adhesives such as PERMABOND® UV648 and UV648, MASTERBOND® 15x-5, and 3M® transfer tapes, such as 3M VHB 3905 and 3M 300 LSE. Bottom substrate 110 may include an arrangement of droplet operations electrodes 118 (e.g., electrowetting electrodes). Droplet operations are conducted atop droplet operations electrodes 118 on a droplet operations surface.

Top substrate 112 may, for example, be formed of a molded material, such injection-molded plastic, or from multiple materials, such as glass combined with injection molded plastic. One or more reservoirs 120, e.g., reservoirs 120a and 120b and a sample input reservoir 122, may be provided. Reservoirs 120 may be integrated into top substrate 112 and may be coupled to a path arranged for flowing fluid into the droplet operations gap. One or more openings 124, e.g., openings 124a through 124d, are provided within top substrate 112. Openings 124 establish a fluid path from reservoirs 120 and sample input reservoir 122 into sufficient proximity of certain droplet operations electrodes 118 on bottom substrate 110. Openings 124 may be closed with a breachable seal 126, e.g., breachable seals 126a through 126c. Breachable seals 126 may, for example, be formed of a wax material that may be breached by the application of a sufficient amount of heat to melt the wax. Breachable seals may alternatively be physically removed or breached, such as by puncturing. For example, an awl (not shown) may be provided for puncturing or removing breachable seals 126. Sample input reservoir 122 includes a vent opening 128 for venting air as liquid is introduced into gap 114. A hinged cap 130 may be used to close sample input reservoir 122 and vent opening 128. Top substrate 112 may also include a recessed area 132. In operation, recessed area 132 may be used to facilitate arrangement of a detector in proximity to the droplet operations gap for detection of reaction products.

Droplet actuator 100 may include one or more temperature control zones 134, e.g., temperature control zones 134a through 134c, for performing certain process steps at predetermined temperatures. One or more heater bars 136, e.g., heater bars 136a through 136c, may be used to melt the wax seals (e.g., breachable seals 126) and/or to control the temperature of filler fluid that is in gap 114 to establish temperature control zones 134. In one example, temperature control zone 134a may be used for sample preparation and denaturation of DNA for PCR analysis. In this example, heater bar 136a may be used to heat temperature control zone 134a to a temperature suitable for denaturation of sample DNA. Heater bars 136b and 136c may be used to heat temperature control zones 134b and 134c to temperatures affective to conduct other reaction steps, such as annealing of primer to single-stranded DNA template and primer extension by DNA polymerase. By cycling a droplet including amplification reagents and a sample including a target nucleic acid through the thermal zones, the target nucleic acid may be amplified. Real-time detection may be used to detect amplified product during amplification and/or an end-point measurement may be taken.

A magnet 138 may be associated with droplet actuator 100. Magnet 138 may be arranged such that sample input reservoir 122 is within the magnetic field of magnet 138. Magnet 138 may, for example, be a permanent magnet or an electromagnet. Magnet 138 may be used, for example, to attract and/or immobilize a quantity of magnetically responsive capture beads (not shown). In operation, magnet 138 may be used to assist in a process of a concentrating and collecting target nucleic acid captured on magnetic beads from a sample fluid for PCR analysis. Magnet 138 may be used to assist in a process of removing unwanted materials from a sample prior to analysis. Heater 140 may be associated with droplet actuator 100. Heater 140 may, for example, be an ultrasonic heater, which for supplying sound and thermal energy (e.g., ultrasound) to a sample fluid to agitate and/or disrupt particles (e.g., to perform cell lysis) in the fluid.

Referring to FIG. 1B, the arrangement of droplet operations electrodes 118 may include multiple dispensing electrodes, such as, but not limited to, sample dispensing electrodes 142a and 142b for dispensing sample fluids (e.g., DNA immobilized on magnetically responsive beads); reagent dispensing electrodes 144a and 144b for dispensing sample preparation reagent fluids, such as wash buffer and DNA elution buffer: and reagent dispensing electrodes 146a and 146b for dispensing PCR reagent fluids, such as dNTPs and enzyme. Sample dispensing electrodes 142, reagent dispensing electrodes 144 and 146 are interconnected through an arrangement, such as a path or array, of droplet operations electrodes 118. A detection spot 148 is positioned in proximity of recessed area 132, for example for detecting target components from or of a sample.

Sample preparation reagents and assay reagents (e.g., PCR reagents) may be pre-loaded and stored on droplet actuator 100. Pre-loading of droplet actuator 100 with assay components provides a ready-to-use device that minimizes hands-on time during operation. In one example, a quantity of dried sample preparation reagents 150 (e.g., magnetically responsive beads) may be deposited and stored in sample input reservoir 122. A quantity of dried PCR reagents 152 may be deposited and stored in reservoir 120a within openings 126a and 126b. A quantity of reconstitution buffer 154 may be deposited and stored in reservoir 120a. A quantity of filler fluid 156 (e.g., silicone oil) may be deposited and stored in reservoir 120b. Filler fluid 156 is of sufficient quantity to fill gap 114 during operation of droplet actuator 100.

Figure 2A:
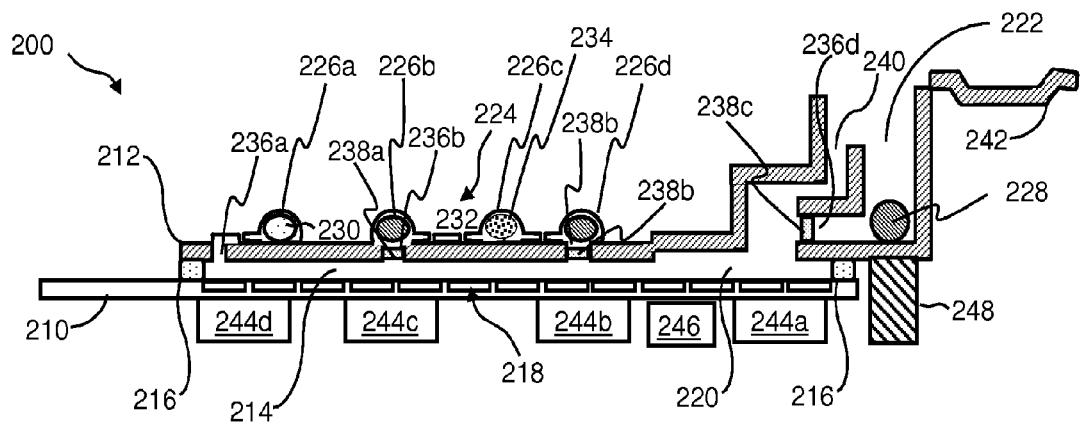
FIGS. 2A through 2C illustrate side views and a top view of another example of a droplet actuator configured for sample-to-result analysis of a single biological sample.
Figure 2B:
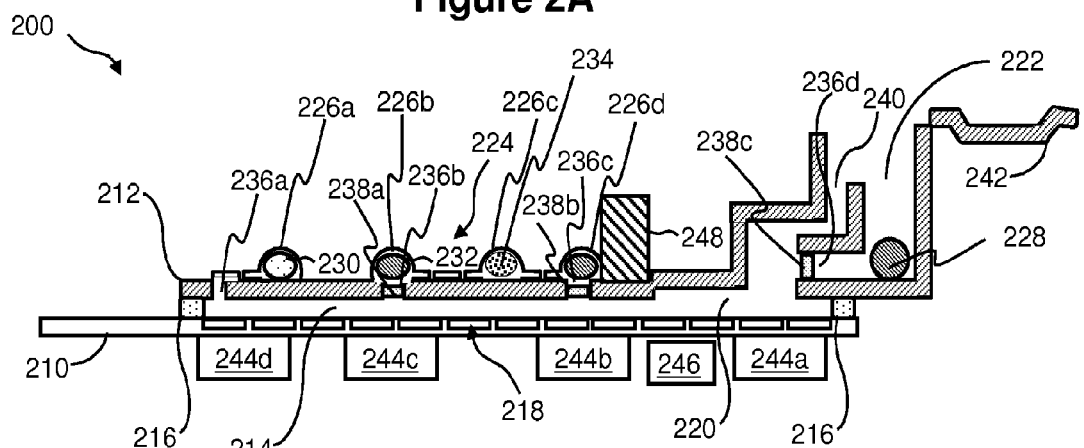
Figure 2C:
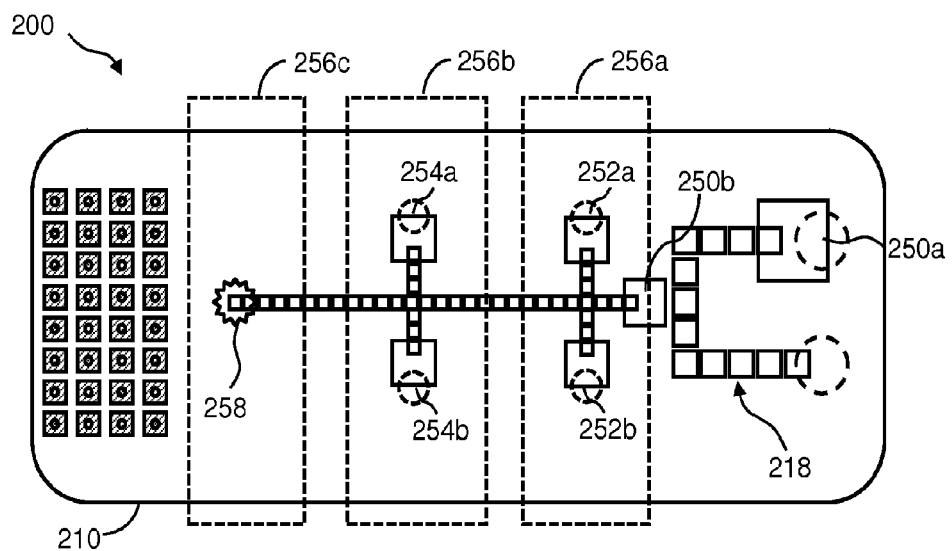

FIGS. 2A through 2C illustrate side views and a top view of another example of a droplet actuator 200 that is configured for sample-to-result analysis of a single biological sample. Droplet actuator 200 is an example of a droplet actuator in which filler fluid, sample preparation reagents, and assay reagents (e.g. PCR reagents) are pre-loaded. One or more of the filler fluid, buffers and reagents may be provided in a reagent storage substrate, which may take the form of a "blister pack." The reagent storage substrate is made of a deformable material and includes cavities or pockets suitable for storing liquid or dried reagents. Preferably a material is selected which does not interact with the buffers or reagents to an extent that renders them unsuited for their intended use. Examples of suitable materials for the reagent storage layer include polyvinyl chloride (PVC), polychlorotrifluoroethylene (PCTFE), and cyclic olefin copolymers (COC).

Droplet actuator 200 may include a bottom substrate 210 and a top substrate 212 that are separated by a gap 214. A gasket 216 may be used to provide a seal around the outer edge of gap 214. Bottom substrate 210 and/or top substrate 212 may include an arrangement of droplet operations electrodes 218 (e.g., electrowetting electrodes). Droplet operations are controlled by droplet operations electrodes 218 on a droplet operations surface.

Top substrate 212 may, for example, be formed of injection-molded plastic. An area of increased gap height may be provided in the droplet operations gap to establish an on-actuator sample reservoir 220 (on-actuator meaning in the droplet operations gap or on the droplet operations surface). An off-actuator sample input reservoir 222 (off actuator meaning exterior to the droplet operations gap and off of the droplet operations surface), may be positioned relative to in-gap sample reservoir 220 and arranged with one or more fluid paths to flow liquid from off actuator reservoir 222 into on actuator reservoir 220. A reagent storage layer 224 may be provided atop top substrate 212. Reagent storage layer 224 may, for example, be formed of plastic, or another suitable material. Reagent storage layer 224 may include one or more compartments 226, e.g., compartments 226a through 226d, in a blister pack array. Sample input reservoir 222 and compartments 226 may contain (e.g., pre-loaded) a quantity of fluids or dried reagents. In one example, sample input reservoir 222 may contain a quantity of dried reagents 228. Compartment 226a may include a quantity of filler fluid 230 such as silicone oil. Compartments 226b and 226d may include a quantity of dried reagents 232, such as PCR or immunoassay reagents. Compartment 226c may contain a quantity of reagent reconstitution buffer 234. Filler fluid 230 and reconstitution buffer 234 contained within compartments 226 are physically separated from dried reagents 232 and/or gap 214 by one or more frangible seals within the blister pack array as described in more detail with reference to FIG. 3.

One or more openings 236, e.g., openings 236a through 236d, are provided within top substrate 212. Openings 236 establish a fluid path from reagent storage layer 224 and sample input reservoir 222 into proximity with droplet operations electrodes 218 on bottom substrate 210 (that is, proximity which is sufficient to permit the droplets to be controlled by the electrodes). Openings 236 may be closed with a breachable seal 238, e.g., breachable seals 238a through 238c. Breachable seals 238 may, for example be formed of a wax material that may be removed by the application of a sufficient amount of heat to melt the wax. Sample input reservoir 222 includes a vent opening 240 for venting air as liquid is introduced into gap 214. A cap 242, such as a hinged cap, may be used to close sample input reservoir 222 and vent opening 240. In another embodiment, sample input reservoir 222 may function as a venting port and vent opening 240 may be eliminated.

One or more heater bars 244, e.g., heater bars 244a through 244d, may be associated with droplet actuator 200. Heater bars 244 may be used to melt the wax seals (e.g., breachable seals 238) and/or control the temperature of filler fluid in vicinity of heater bars 244, e.g., as described above with respect to FIGS. 1A and 1B.

A magnet 246 may be associated with droplet actuator 200. Magnet 246 may, for example, be a permanent magnet or an electromagnet. Magnet 246 may, for example, be used to attract and/or immobilize a quantity of magnetically responsive capture beads (not shown). In operation, magnet 246 may be used with magnetic beads to assist in a process of a concentrating and collecting target nucleic acid from a sample fluid for PCR analysis, collecting other analytes, or removing unwanted components, e.g., as described above with respect to FIGS. 1A and 1B.

A sonicator 248 may be associated with droplet actuator 200. The sonicator may be any source of sonic energy and may be provided as a component of the droplet actuator cartridge or as a component of an instrument or cartridge docking station, modular drive or bay to which the droplet actuator cartridge is coupled during operation (e.g., as described in Pollack et al., U.S. Patent Pub. No. 20100143963, entitled "Modular Droplet Actuator Drive," published on Jun. 10, 2010, the entire disclosure of which is incorporated herein by reference). Referring to FIG. 2A, in one embodiment, sonicator 248 may be in contact with off-actuator (meaning outside the droplet operations gap) sample input reservoir 222. Referring to FIG. 2B, in another embodiment, sonicator 248 may be in contact with top substrate 212 near on-actuator sample input reservoir 222. Sonicator 248 may be used to apply sound energy (e.g., ultrasound) to a sample fluid to agitate and/or disrupt particles (e.g., to perform cell lysis) in the fluid. Referring to FIG. 2C, the arrangement of droplet operations electrodes 218 may include multiple dispensing electrodes, such as, but not limited to, sample dispensing electrodes 250a and 250b for dispensing sample fluids (e.g., DNA immobilized on magnetically responsive beads); reagent dispensing electrodes 252a and 252b for dispensing sample preparation reagent fluids, such as wash buffer and DNA elution buffer; and reagent dispensing electrodes 254a and 254b for dispensing PCR reagent fluids, such as dNTPs and enzyme. Sample dispensing electrodes 250, reagent dispensing electrodes 252 and 254 are interconnected through an arrangement, such as a path or array, of droplet operations electrodes 218. The arrangement of droplet operations electrodes 218 and position of heater bars 244 provide certain droplet operations regions 256, e.g., droplet operations regions 256a through 256c, for performing different processing steps. A detection spot 258 is positioned within droplet operations regions 256c.

Droplet actuator 200 may be manufactured by loading reagents and/or reconstitution solutions into compartments 226. An adhesive may be patterned onto a top surface of top substrate 212 and/or on reagent storage layer 226. Reagent storage layer 226 may be affixed to a top surface of top substrate 212, thereby sealing reagents and reconstitution solutions. Like other droplet actuator embodiments of the invention, droplet actuator 200 may be labeled and packaged. Droplet actuator 200 may be packaged together with other components, such as instructions for use of droplet actuator 200. In some cases, openings 236 may be sealed by the reagent storage layer, e.g., as shown with respect to opening 236a (see also FIG. 3).

Figure 3:
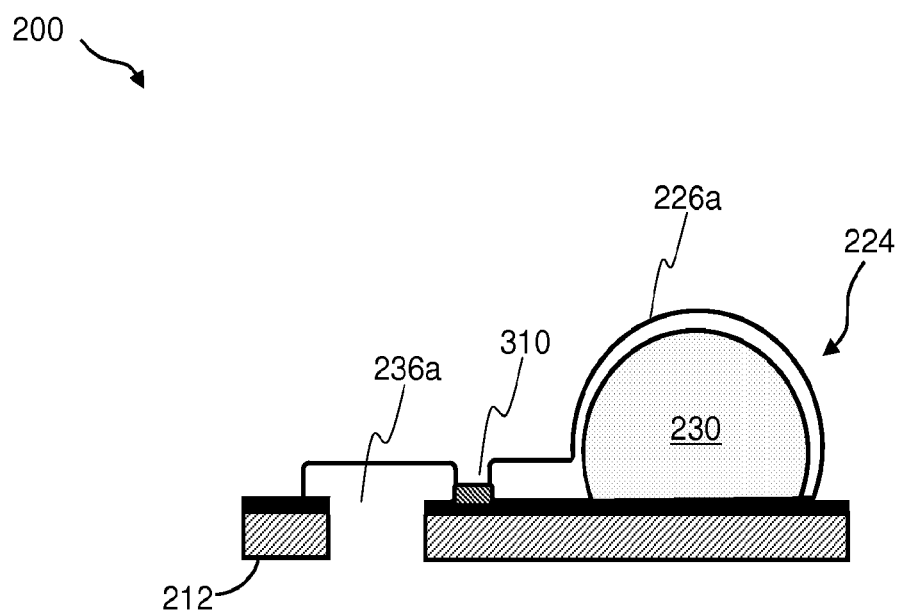
FIG. 3 illustrates a portion of the droplet actuator of FIG. 2 and illustrates the arrangement of a physical barrier for separating a blister pack compartment from an opening in the top substrate.

In operation, a volume of sample fluid is loaded into sample input reservoir 222 and hinged cap 232 is closed. The sample fluid may, for example, be a blood sample or a nasal pharyngeal wash sample of about 1 ml or more in volume that contains a quantity of target analytes (e.g., bacterial, viral, and/or fungal targets), or other biological sample. As the sample fluid is loaded into sample input reservoir 222, sample preparation reagents 228 are reconstituted. The frangible seals enclosing compartments 226a and 226c are disrupted by the application of pressure (e.g., closing the lid of the instrument) such that filler fluid 230, e.g., silicone oil, is released into gap 214 and reconstitution buffer 234 is released into adjacent compartments 226b and 226d or manually pressing the compartments to force flow of the reconstitution buffer into contact with the dried reagents and into the droplet operations gap. As reconstitution buffer is released into the adjacent compartments, dried reagents 232 are reconstituted. When present, sonicator 240 may be activated and used to agitate particles and/or lyse cells (disrupt cell membranes) in the sample fluid. A sonicator may also or alternatively be provided to accelerate reconstitution of dried reagents. Where wax seals are present, heater bar 244a is heated to a temperature that is sufficient to melt wax seal 238c. As wax seal 238c is melted, the lysed sample fluid is released into on-actuator sample reservoir 220 for further processing. In another example, referring to FIG. 2B, the sample fluid is first released into on-actuator sample reservoir 220 and subsequently lysed by activation of sonicator 240. In another embodiment, FIG. 3 illustrates a portion of droplet actuator 200 of FIG. 2 and illustrates the arrangement of a physical barrier for separating a blister pack compartment from an opening in the top substrate. For example, compartment 226, a component of reagent storage layer 224, with filler fluid 230 therein is physically separated from opening 236a by a physical barrier 310. Physical barrier 310 may, for example, be a frangible barrier, such as a pressure sensitive seal, such as an adhesive selected to permit the seal to be broken upon application of pressure to compartment. Because physical barrier 310 is frangible, e.g., a pressure sensitive seal, a certain amount of pressure may be applied on physical barrier 310 in order to break the seal and release filler fluid 230 from compartment 226a into opening 236a and into the gap of the droplet actuator. A single frangible seal separating a blister pack compartment from an opening in the top substrate is illustrated in FIG. 3, but any number of frangible seals may be used to separate any liquid contained in a blister pack compartment from the gap in a droplet actuator and/or other liquids or dried reagents in adjacent blister pack compartments. The arrangement of physical barriers 310 and removable wax seals (referring to FIGS. 2A and 2B) provide for compartmentalization of reagents until the droplet actuator is loaded into an instrument deck and ready for use. Adhesives may be patterned on the reagent storage layer 224 or top substrate 212 in a manner which permits barrier 310 to be breached upon application of pressure to compartment 226a, but without breaching other sealed portions of reagent storage layer 224 which are not intended to be broken.

FIGS. 4A and 4B illustrate a droplet actuator 400 and illustrate variations in gap height associated with certain droplet operation regions. FIG. 4A illustrates a top view of droplet actuator 400. FIG. 4B illustrates a cross-sectional view of droplet actuator 400 taken along line A-A of FIG. 4A. Droplet actuator 400 is an example of a two-step droplet actuator that is configured for manipulation of different size droplets, e.g., from about 1000 μL to about 2.5 in a sample-to-result protocol.

Droplet actuator 400 may include a bottom substrate 410 and a top substrate 412 that are separated by a gap 414. The region of gap 414 essentially serves as an on actuator reservoir with capabilities for accepting and mixing reagents via an opening in top substrate 412. A gasket 416 may be used to provide a seal around the outer edge of droplet actuator 400. Bottom substrate 410 may include an arrangement of droplet operations electrodes 418 (e.g., electrowetting electrodes). Droplet operations are conducted atop droplet operations electrodes 418 on a droplet operations surface. Droplet actuator 400 may include certain regions for performing certain process steps. For example, droplet actuator 400 may include, but is not limited to, a sample dispensing region 420 (e.g., storage and dispensing) and a droplet operations region 422 (e.g., mixing, incubation, washing, detection). Additionally, the height of gap 414 at each region may vary. Droplet actuator 400 of the invention is not limited to the number, types, and physical arrangement of regions that are shown in FIGS. 4A and 4B. The configuration of droplet actuator 400 that is shown in FIGS. 4A and 4B is exemplary only. Any number, types, and physical arrangement of regions having the same and/or different gap heights in a droplet actuator is possible. Other examples are described in reference to FIGS. 6 through 9B.

One or more sample dispensing electrodes 424, e.g., sample dispensing electrodes 424a through 424e, and reagent dispensing electrodes 426, e.g., reagent dispensing electrodes 426a through 426d, may be arranged in relation to droplet operations electrodes 418. Sample dispensing electrodes 424 may, for example, be used to manipulate a large volume of sample fluid (e.g., about 1 mL) that contains a quantity of magnetically responsive beads for processing within droplet actuator 400. To provide for manipulating a large volume of sample fluid, sample dispensing electrodes 424c, 424d, and 424e may, for example, be installed on a pitch of about 2.25 mm. In one embodiment, the region of increased gap height is associated with path of adjacent electrodes, such as sample dispensing electrodes 424c, 424d, and 424e, which are, relative to the direction of dispensing, wider than they are long, as shown in FIG. 4A. Reagent dispensing electrodes 426 may, for example be used to dispense one or more reagent droplets, such as wash buffer droplets, elution buffer droplets, and PCR reagent droplets, for combining with a sample droplet for PCR analysis of target nucleic acid sequences, or for shuttling a droplet back and forth for mixing. One or more waste disposal electrodes 428, e.g., waste disposal electrodes 428a through 428d, may be may be positioned within a waste disposal region (not shown in FIG. 4B cross-section). Sample dispensing electrodes 626 and waste disposal electrodes 428 are interconnected by a path or array of droplet operations electrodes 418. The interface between droplet operations region 422 and a waste disposal region, where the gap height transitions from H1 to H2, is described in more detail with reference to FIG. 6 and FIG. 8. In one embodiment, the height transition region from H1 to H2 is aligned with an edge of an electrode, e.g., as shown in FIGS. 4A and 4B. In an alternative embodiment (not shown), an electrode, such as electrode 424b, spans the height transition region from H1 to H2.

The configuration of droplet actuator 400 is such that a single droplet (not shown) may be dispensed, using a typical electrowetting dispensing electrode activation scheme, from sample dispensing electrodes 424 onto droplet operations electrodes 418 for transport and processing within droplet actuator 400. The variability in gap height that may be associated with different processing regions (e.g., sample dispensing region 420 and droplet operations region 422) in droplet actuator 400 is illustrated in FIG. 4B. In this example, two different gap heights along gap 414 may be associated with the different processing regions. Sample dispensing region 420 of droplet actuator 400 may have a certain gap height (H2) that is sufficiently large (e.g., >3 mm) to facilitate storage of larger liquid volumes (e.g., about 1 mL) and ready dispensing of droplets. Droplet operations region 422 may have a gap height (H1) which is smaller (e.g., 250-500 μm) than H2 that facilitates, for example, rapid transport, mixing, washing, and/or incubation of one or more droplets. The reduction in gap height from H2 to H1 is such that a certain height ratio H2:H1 is maintained to provide for efficient dispensing of droplets. Gap height requirements for sample storage/dispensing (H2) and other droplet operations (H1) on droplet actuator 400 may be described as H2≥H1.

Examples of different gap heights for a two-step droplet actuator are shown in Table 1. All gap heights shown in Table 1 (e.g., droplet actuators 1 through 5) provided for transport (e.g., electrowetting) of droplets from H2 to H1. However, as H2:H1 increases, dispensing of fluids from H2 to H1 may be less efficient. For a given voltage, the factors that affect the ability to dispense from H2 to H1 depend on the ratio of H2:H1 and the interfacial tension of the droplet with the solid substrates.

TABLE 1

Variation of H1 and H2 gap heights

| Droplet Actuator | H1 | H2 | Quantity |
| --- | --- | --- | --- |
| 1 | 550-600 μm | ~1.5 mm | 2 |
| 2 | 550-600 μm | ~3 mm | 2 |
| 3 | 550-600 μm | ~5 mm | 2 |
| 4 | 275-300 μm | ~1 mm | 2 |
| 5 | 275-300 μm | ~2 mm | 2 |

In another embodiment, variation in gap height from a sample storage and dispensing region to a droplet operations region may transition from H2 to H1 to H0, e.g., a three-step transition. For example, H2 may be about 5 mm, H1 may be about 1 mm, and H0 may be about 300-600 μm. In some embodiments, H2:H1 is about equal to H1:H0. H1 may, for example, range from about 1 μm to about 2000 μm, or from about 10 μm to about 1000 μm, or from about 50 μm to about 750 μm. H2 may range from about 0.1 mm to about 10 mm, or from about 1 mm to about 7.5 mm, or from about 15 mm to about 5 mm.

FIGS. 5A, 5B, and 5C illustrate other top views of droplet actuator 400 of FIGS. 4A and 4B and show a process of concentrating and dispensing magnetically responsive beads from a large sample volume. The process shown in FIGS. 5A, 5B, and 5C is an example of a method wherein a large sample volume is manipulated as a single droplet in a process of concentrating and dispensing magnetically responsive beads.

Droplet actuator 400 may contain a quantity (e.g., about 1 mL) of sample fluid 510. In one embodiment, sample fluid may contain DNA to be evaluated by PCR analysis. Sample fluid 510 may contain a quantity of magnetically responsive beads 512, such as nucleic acid capture beads (e.g., ChargeSwitch beads). A magnet 514 is provided in proximity to certain sample dispensing electrodes 424 within sample dispensing region 420 for retaining a quantity of magnetically responsive beads. In particular, magnet 514 is arranged such that sample dispensing electrode 424a is within the magnetic field thereof. Magnet 514 may, for example be a permanent magnet or an electromagnet. Alternative magnet arrangements and positioning for attraction and collection of magnetically responsive beads are described in reference to FIG. 15 and FIG. 16.

An example of a process of concentrating and dispensing a quantity of magnetically responsive beads from a large sample volume on a droplet actuator may include, but is not limited to, the following steps.

In one step, FIG. 5A shows sample fluid 510, with magnetically responsive beads 512 therein, that is positioned at sample dispensing electrodes 424c and 424d, which is within sample dispensing region 420 (gap height H2) and away from magnet 514. Because sample fluid 510 is positioned away from and out of the magnetic field of magnet 514, magnetically responsive beads 512 are dispersed somewhat evenly throughout the volume of sample fluid 510. Sample dispensing electrodes 424c and 424d are activated (turned ON).

In another step, FIG. 5B shows a finger of sample fluid 510 that is formed by extending the liquid atop adjacent sample dispensing electrodes 424. In this step, sample dispensing electrodes 424a and 424b, and optionally 424c, are activated (turned ON). Finger of sample fluid 510 is drawn along sample dispensing electrodes 424b and 424a, which is away from sample dispensing electrodes 424c and 424d and toward magnet 514. At sample dispensing electrode 424b, the height of gap 414 transitions from H2 to H1, e.g., the height of gap 414 gets smaller from H2 to H1. The magnetic force of magnet 514 concentrates magnetically responsive beads 512 in a region of the finger that is closest to magnet 514.

In another step, FIG. 5C shows a bead droplet 516 that is formed atop sample dispensing electrode 424a. In this step, sample dispensing electrodes 424b and 424c are deactivated (turned OFF) and sample dispensing electrode 424e is activated (turned ON). Sample dispensing electrodes 424a and 424d remain activated. As a result, the finger of sample fluid 510 snaps off and bead droplet 516 is formed atop sample dispensing electrode 424a within gap height H1.

The method of the invention may be used to create a high concentration of magnetically responsive beads 512 in a single bead containing droplet from a relatively large sample volume (e.g., about 1 mL). Once the highly concentrated magnetically responsive bead droplet 516 is formed, it may be subjected to other droplet operations within droplet actuator 400.

In another embodiment, the process shown in FIG. 5 may be used to form a single bead containing droplet in a droplet actuator where the gap height transitions from H2 to H1 to H0 (H0≤H1≤H2).

FIGS. 6A and 6B illustrate a top view and a side view, respectively, of a droplet actuator 600 and illustrate variations in gap height associated with sample storage and waste disposal regions. Droplet actuator 600 is an example of a droplet actuator that is configured for storage of large volumes of sample fluid and waste fluid.

Droplet actuator 600 may include a bottom substrate 610 and a top substrate 612 that are separated by a gap 614. Bottom substrate 610 may include an arrangement of droplet operations electrodes 618 (e.g., electrowetting electrodes). Droplet operations are conducted atop droplet operations electrodes 618 on a droplet operations surface. Droplet actuator 600 may include certain regions for storing sample fluids and waste fluids. For example, droplet actuator 600 may include, but is not limited to, a sample dispensing region 620 (e.g., storage and dispensing) and a waste disposal region 622 that are interconnected by a droplet operations region 624. The height of gap 614 at each region may vary.

One or more sample dispensing electrodes 626, e.g., sample dispensing electrodes 626a through 626e may be positioned within sample dispensing region 620 on bottom substrate 610. Sample dispensing electrodes 626 may, for example, be used to manipulate a large volume of sample fluid (e.g., about 1 mL) that contains a quantity of magnetically responsive beads for processing within droplet actuator 600. One or more waste disposal electrodes 628, e.g., waste disposal electrodes 628a through 628d, may be positioned within waste disposal region 622 on bottom substrate 610. Sample dispensing electrodes 626 and waste disposal electrodes 628 are interconnected by a path or array of droplet operations electrodes 618 within droplet operations region 624.

The configuration of electrodes in droplet actuator 600 is such that one or more droplets (not shown) may be dispensed from sample dispensing electrodes 626 onto droplet operations electrodes 618 for transport and processing within droplet actuator 600. The variability in gap height that may be associated with different processing regions, e.g., sample dispensing region 620, waste disposal region 622, and droplet operations region 624, in droplet actuator 600 is illustrated in FIG. 6B. In this example, two different gap heights along gap 614 may be associated with the different processing regions. Sample dispensing region 620 and waste disposal region 622 of droplet actuator 600 may have a certain gap height (H2) that is sufficiently large to facilitate storage of larger liquid volumes and ready dispensing and disposal of droplets. Droplet operations region 624 may have a gap height (H1) which is smaller than H2 that facilitates, for example, rapid transport, mixing, washing, and/or incubation of one or more droplets. The reduction in gap height from H2 to H1 is such that a certain height ratio H2:H1 is maintained to provide for efficient dispensing of droplets. The increase in gap height from H1 to H2 is such that waste fluid disposed within disposal region 622 is effectively retained.

FIGS. 7A and 7B illustrate another top view and side view, respectively, of droplet actuator 400 of FIGS. 4A and 4B and illustrate another example of a two-step droplet actuator configured for integrated sample-to-result analysis of a single biological sample. The configuration of droplet actuator 400 shown in FIGS. 7A and 7B is substantially the same as shown in FIGS. 4A and 4B except that an off-actuator sample reservoir is associated with droplet actuator 400. For example, a substrate 710 may be provided atop top substrate 414. Substrate 710 may include a sample reservoir 712 for containing a quantity of sample fluid. Substrate 710 may, for example, be formed of plastic, glass or another suitable substrate. An opening 714 is provided within top substrate 412, establishing a fluid path from sample reservoir 712 into gap 414 into sufficient proximity with certain droplet operations electrodes 418 to permit the electrode to interact with a liquid flowed through the fluid path.

FIG. 8 illustrates yet another side view of a portion of droplet actuator 400 of FIGS. 4A and 4B and illustrates the interface between droplet operations and waste disposal regions where the gap height transitions from H1 to H2. In this example, two different gap heights along gap 414 may be associated with the different processing regions. A waste disposal region 810 of droplet actuator 400 may have a certain gap height (H2) that is sufficiently large to facilitate storage of larger liquid volumes (e.g., about 1 mL). A droplet operations region 812 may have a gap height (H1) which is smaller than H2 that facilitates, for example, rapid transport of one or more droplets. Pressure differences between H1 (higher pressure area) and H2 (lower pressure area) facilitate transport of waste droplets into waste disposal region 810. For example, one or more waste droplets (not shown) may be transported using droplet operations (e.g., electrowetting) along droplet operations electrodes 418 in gap region H1 to waste disposal electrodes 428 at the interface of gap H2. Because the surfaces of a droplet actuator are typically hydrophobic and the differences in pressure from H1 to H2, waste droplets are effectively pulled into waste disposal region 810. The variability in gap height is such that a large volume waste fluid disposed within disposal region 810 is effectively retained.

In another embodiment, the waste disposal region described in reference to FIGS. 6A and 6B and FIG. 8 may be eliminated. In this example, the sample dispensing region may function as a waste disposal region after the sample has been dispensed. The transition in gap height from a droplet operations region (H1) to the sample dispensing region (H2) is of sufficient height to effectively retain a large volume of waste fluid.

FIGS. 9A and 9B illustrate yet another top view and side view, respectively, of droplet actuator 400 of FIGS. 4A and 4B and illustrate an example of a three-step droplet actuator configured for integrated sample-to-result analysis of a single biological sample. In this example, top substrate 412 of FIG. 4 is replaced with a top substrate 912, where the gap height of a sample storage and dispensing region is increased such that the overall footprint of the droplet actuator is decreased. An intermediate gap height region is provided such that large pressure differences associated with dispensing from a larger gap height to a smaller gap height are significantly reduced. In this example, variations in gap height associated with certain droplet operations regions transition from H2 to H1 to H0 (H2≥H1≥H0).

A substrate 920 may be provided atop top substrate 912. Substrate 920 may include a well 922 for containing a quantity of sample fluid. Substrate 920 may, for example, be formed of plastic, glass or another suitable substrate. An opening 944 is provided within top substrate 912, establishing a fluid path from well 922 into gap 414 into sufficient proximity with certain droplet operations electrodes 918 to permit the electrode to interact with a liquid flowed through the fluid path.

Droplet actuator 400 may include certain regions for performing certain process steps. For example, droplet actuator 400 may include, but is not limited to, a sample dispensing region 926 (e.g., storage and dispensing), an intermediate dispensing region 928, and a droplet operations region 930 (e.g., mixing, incubation, washing, detection). The height of gap 414 at each region may vary. Sample dispensing region 926 of droplet actuator 900 may have a certain gap height (H2) that is sufficiently large to facilitate storage of larger liquid volumes (e.g., about 1 mL) in a smaller amount of x-y space. Intermediate sample dispensing region 928 may have a certain gap height (H1) which is smaller than H2 that facilitates dispensing of sample fluid from a large gap height to a smaller gap height. Droplet operations region 930 may have a gap height (H0) which is even smaller than H1 that facilitates droplet operations such as rapid transport, mixing, washing, and/or incubation of one or more droplets. The reduction in gap height from H2 to H1 to H0 (H0≤H1≤H2) is such that a certain height ratio H2:H1 is approximately equivalent to the ratio of H1:H0. Large pressure differences between H2 and H0 are minimized by the transition through gap height H1.

FIG. 10 illustrates yet another top view of droplet actuator 400 of FIGS. 4A and 4B and illustrates an example of suitable dimensions of the droplet actuator. Each droplet operations electrode 418 may, for example have a dimension of about 2.125 mm×2.12 mm. Bottom substrate 410 may include an arrangement of larger sample dispensing electrodes 424 (e.g., sample dispensing electrodes 424c, 424d, and 424e) and smaller sample dispensing electrodes 424 (e.g., sample dispensing electrodes 424a and 424b). Each larger sample dispensing electrode may, for example, be about 6.75 mm×13.5 mm in size. Each smaller sample dispensing electrode may, for example, be about 6.75 mm×6.75 mm in size. Bottom substrate 410 may include an arrangement of reagent dispensing electrodes 426 (e.g., 4 reagent dispensing electrodes 426). Each reagent dispensing electrode may, for example, be about 6.75×6.75 mm in size.

7.2 Mixing

FIGS. 11/A through 11C illustrate top views of an electrode arrangement 1100 and show a process for mixing a small volume of fluid with a larger volume of fluid. The process shown in FIGS. 11A through 11C is an example of a mixing process in which a small volume of fluid such as a reagent fluid (e.g., magnetically responsive beads suspended in an assay buffer) is combined using the process of diffusion with a larger volume of fluid such as a sample fluid (e.g., about 1 mL of a biological sample).

Electrode arrangement 1100 may include a large sample dispensing electrode 1110. Sample dispensing electrode 1110 may, for example, be positioned within a sample dispensing region with a gap height of H2 as described in reference to FIGS. 7A and 7B. One or more smaller, narrow mixing electrodes 1112 may be positioned within sample dispensing electrode 1110. In this example, three narrow mixing electrodes 1112 are arranged in parallel within sample reservoir electrode 1110; however, any number or arrangement (e.g., arranged in a grid pattern) of narrow mixing electrodes 1112 may be used. The number and spacing between successive narrow mixing electrodes 1112 may, for example, be determined by the diffusion rate of the two fluids to be mixed. The arrangement of narrow mixing electrodes 1112 within sample dispensing electrode 1110 is such that a sufficiently large interface area for diffusion is created between a reagent fluid in narrow mixing electrodes 1112 and a sample fluid in sample dispensing electrode 1110.

An example of a mixing method that uses diffusion to mix a smaller volume of reagent fluid with a larger volume of sample fluid may include, but is not limited to, the following steps.

In one step, FIG. 11B shows a volume of reagent fluid 1114 loaded (e.g., by electrowetting) in narrow mixing electrodes 1112. Reagent fluid 1114 may, for example, be about 10 or about 15 or about 25 µL in volume. Reagent fluid 1114 may, for example, include a quantity of magnetically responsive beads for distribution in a sample fluid. In another example, reagent fluid 1114 may be another reagent fluid without a quantity of magnetically responsive beads.

In another step, FIG. 11C shows a larger volume of sample fluid 1116 loaded on sample dispensing electrode 1110. As sample fluid 1116 is loaded on sample dispensing electrode 1110, mixing of sample fluid 1116 and reagent fluid 1114 occurs by diffusion.

FIGS. 12A and 12B illustrate top views of an electrode arrangement 1200 and show another process for mixing a larger volume of fluid. The process shown in FIGS. 12A and 12B is an example of a mixing process in which the inherent circulation at one or more electrode edges is used to promote mixing of a larger volume of fluid (e.g., about 1 mL).

Electrode arrangement 1200 may include a large dispensing electrode 1210. Dispensing electrode 1210 may, for example, be positioned within a sample dispensing region with a gap height of H2 as described in reference to FIGS. 7A and 7B. One or more smaller, mixing electrodes 1212 may be situated within dispensing electrode 1210. In one example, four round mixing electrodes 1212a through 1212d are arranged within dispensing electrode 1210. The number and spacing between round mixing electrodes 1212 may, for example, be determined by interfacial tension of the fluids to be mixed.

An example of a mixing process in which the inherent circulation at one or more electrode edges is used to promote mixing of a larger volume of fluid may include, but is not limited to, the following steps.

In one step, FIG. 12A shows a volume of fluid 1214 loaded on dispensing electrode 1210 and mixing electrodes 1212. Fluid 1214 may, for example, be a volume of sample fluid that contains a quantity of reagent fluid, e.g., magnetically responsive beads, for dispersion within the sample fluid. Dispensing electrode 1210 and mixing electrodes 1212 are activated (turned ON).

In another step, FIG. 12B shows certain mixing electrodes 1212, e.g., mixing electrodes 1212a and 1212d, turned OFF (deactivated). As mixing electrodes 1212a and 1212d are turned OFF, fluid 1214 is cleared from mixing electrodes 1212a and 1212d. Circulation of fluid 1214 occurs at the edges of the OFF electrodes. By activating and deactivating mixing electrodes 1212 in, for example, a random pattern, mixing occurs across the volume of fluid 1214.

FIG. 13 illustrates a side view of an example of an on-actuator sample reservoir 1300 of a droplet actuator and illustrates a method of mixing large volumes of liquid with smaller volumes of reagents. The process shown in FIG. 13 is an example of a mixing method that uses manual pipetting of a sample fluid into and out of an on-actuator sample reservoir to mix larger volumes of sample fluid with a smaller volume of reagent fluid.

Sample reservoir 1300 may include a bottom substrate 1310 and a top substrate 1312 that are separated by a gap 1314. A gasket 1316 may be used to provide a seal around the sample reservoir 1300. Bottom substrate 1310 may include an arrangement of sample dispensing electrodes 1318 (e.g., electrowetting electrodes). An opening 1320 is provided within top substrate 1312. Opening 1320 establishes a fluid path into gap 1314 and onto sample dispensing electrodes 1318 on bottom substrate 1310. Opening 1320 may be of sufficient size to accommodate the tip of a fluid delivery device 1322. In one example, fluid delivery device 1322 may be a pipette that includes a pipette tip 1324. In this example, opening 1320 is of sufficient size to accommodate pipette tip 1324.

In operation, a small volume of reagent fluid (e.g., about 3-6 µL) is preloaded in sample reservoir 1300. In one example, the reagent fluid may include a quantity of beads 1326. Fluid delivery device 1322 is used to introduce a larger volume of fluid 1328 (e.g., sample fluid of about 1 mL) into sample reservoir 1300 through opening 1320. Fluid 1328 is repeatedly pipetted into and out of sample reservoir 1300 through opening 1320 and pipette tip 1324 using fluid delivery device 1322. As fluid 1328 is repeatedly pipetted into and out of sample reservoir 1300 and pipette tip 1324, beads 1326 are substantially dispersed within fluid 1328.

FIG. 14 illustrates a side view of an example of a portion of a droplet actuator 1400 and illustrates another method of mixing a larger volume of fluid with a smaller volume of fluid. The process shown in FIG. 14 is an example of a mixing method that uses one or more off-actuator reservoirs and electrowetting to mix a larger volume of sample fluid with a smaller volume of reagent fluid in an on-actuator sample reservoir.

Sample reservoir 1400 may include a bottom substrate 1410 and a top substrate 1412 that are separated by a gap. A gasket 1416 may be used to provide a seal around the sample reservoir 1400. A certain area between bottom substrate 1410 and top substrate 1412 forms an on-actuator sample reservoir 1414. Bottom substrate 1410 may include an arrangement of sample dispensing electrodes 1418 within on-actuator sample reservoir 1414, e.g., sample dispensing electrodes 1418*a* through 1418*c* (e.g., electrowetting electrodes). Top substrate 1412 may, for example, be formed of a molded material such that one or more off-actuator reservoirs 1420, e.g., reservoirs 1420*a*, 1420*b*, and 1420*c*, are formed. Gating electrodes (not shown) may be positioned in proximity of each off-actuator reservoir 1420. The gating electrodes are used to control the flow of fluid into and out of one or more selected off-actuator reservoir 1420. Off-actuator reservoirs 1420 may be of sufficient size to contain a large volume of fluid, e.g., about 1 mL. Corresponding to off-actuator reservoirs 1420*a*, 1420*b*, and 1420*c* are openings 1422*a*, 1422*b*, and 1422*c*, respectively. Openings 1422*a*, 1422*b*, and 1422*c* establish a fluid path from off-actuator reservoirs 1420*a*, 1420*b*, and 1420*c* into on-actuator sample reservoir 1414.

In operation, a volume of fluid 1424 (e.g., about 1 mL) is drawn from one or more off-actuator reservoirs 1420 through the fluid path into on-actuator sample reservoir 1414 of droplet actuator 1400. Fluid 1424 may, for example, be a sample fluid that includes a quantity of magnetically responsive beads 1426. In one embodiment, a single off-actuator reservoir 1420, e.g., off-actuator reservoir 1420*a*, is used to load fluid 1424 into on-actuator sample reservoir 1414. In this example, reservoir electrode 1418*a* is activated and fluid 1424 is drawn from off-actuator reservoir 1420*a* through opening 1422*a* of top substrate 1412 and onto reservoir electrode 1418*a*. To mix fluid 1424 and beads 1426 therein, the entire volume (or the majority of the volume) of fluid 1424 is repeatedly transferred from on-actuator sample reservoir 1414 through opening 1422*a* into off-actuator reservoirs 1420*a*. In this step, reservoir electrode 1418*a* is deactivated (turned OFF) and fluid 1424 is drawn back into off-actuator reservoir 1420*a* by capillary forces. As fluid 1424 is repeatedly transferred into and out of on-actuator sample reservoir 1414, beads 1426 are substantially dispersed within fluid 1424.

In another embodiment, fluid 1424 is repeatedly transferred into and out of on-actuator sample reservoir 1414 using two or more off-actuator reservoirs 1420, e.g., three reservoirs 1420, e.g., reservoirs 1420*a*, 1420*b*, and 1420*c*. By randomly selecting one or more off-actuator reservoirs 1420 (e.g., activation/deactivation of gating electrodes), more effective mixing is achieved.

In yet another embodiment, an electrode may be provided in each off-actuator reservoir 1420 to facilitate the flow of fluid 1424 from on-actuator sample reservoir 1414 into the off-actuator reservoirs 1420.

FIG. 15 illustrates a side view of a portion of a droplet actuator 1500 and illustrates another method of mixing a large volume of fluid in a droplet actuator. The process shown in FIG. 15 is an example of a mixing method that uses static electrowetting to mix a large volume of fluid in an on-actuator sample reservoir.

Droplet actuator 1500 may include a bottom substrate 1510 and a top substrate 1512 that are separated by a gap 1514. Droplet actuator 1500 may include a sample dispensing region 1516 (e.g., storage and dispensing) and a droplet operations region 1518 (e.g., transporting, incubation, washing). The height of gap 1514 at each region may vary. Sample dispensing region 1516 of droplet actuator 1500 may have a certain gap height (H2) that is sufficiently large to facilitate storage of large volume of fluid (e.g., about 1 mL). Droplet operations region 1518 may have a gap height (H1), which is smaller than H2, that facilitates droplet operations such as rapid transport, mixing, washing, and/or incubation of one or more droplets.

One or more sample dispensing electrodes 1520, e.g., two sample dispensing electrodes 1520*a* and 1520*b*, may be provided within sample dispensing region 1516 on bottom substrate 1510. In a preferred embodiment, a coplanar reference electrode 1522 may be positioned between sample dispensing electrodes 1520. In this example, because reference electrode 1522 is arranged with sample dispensing electrodes 1520, a conductive coating typically applied to the top substrate of a droplet actuator is not required.

An example of a mixing method that uses static electrowetting to mix a large volume of fluid in an on-actuator sample reservoir may include, but is not limited, to the following steps.

Figure 15A:
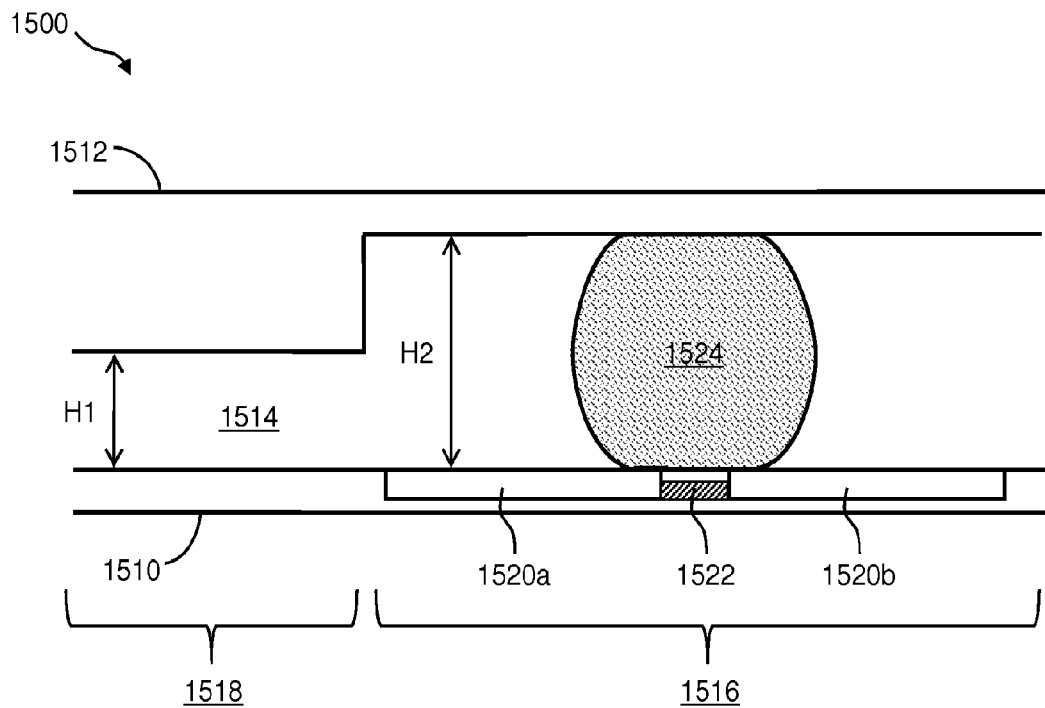

In one step, FIG. 15A shows a volume of fluid 1524 loaded in sample dispensing region 1516 on sample dispensing electrodes 1520. Fluid 1524 may, for example, be a volume of sample fluid that contains a quantity of reagent fluid, e.g., magnetically responsive beads, for dispersion within the sample fluid. Sample dispensing electrodes 1520 are turned OFF (inactive). Because sample dispensing electrodes 1520 are inactive, sample fluid 1524 has a rounded shape and is sandwiched between top substrate 1512 and bottom substrate 1510.

Figure 15B:
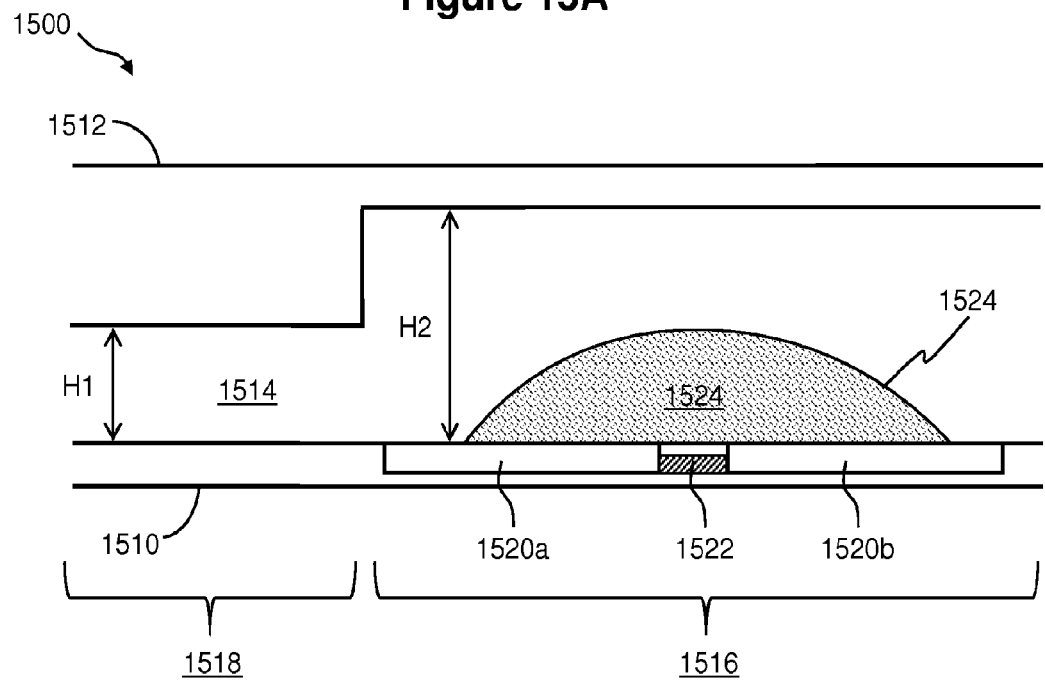

In another step, FIG. 15B shows sample dispensing electrodes 1520 turned ON (activated). As sample dispensing electrodes 1520 are activated, sample fluid 1524 is spread out over sample dispensing electrodes 1520 into a flattened shape and mixing occurs within sample fluid 1524. By repeatedly activating and deactivating sample dispensing electrodes 1520, e.g., pulsing the sample fluid, efficient mixing of sample fluid 1524 occurs.

In various other embodiments, the arrangement of sample dispensing electrodes and interspersed coplanar reference electrodes may be used within the larger gap height regions (H2) of a droplet actuator that includes variations in gap heights. Because a coplanar reference electrode arrangement is used, the conductive coating typically applied to the top substrate of a droplet actuator is not required.

In another embodiment, a piezoelectric strip (not shown) may be used to provide a sufficient amount of voltage to agitate and mix a sample fluid. In this example, the piezoelectric strip may be positioned atop the top substrate of the droplet actuator or below the droplet actuator or within the droplet actuator.

7.3 Bead Collection

FIGS. 16A and 16B illustrate yet other top views of droplet actuator 400 of FIGS. 4A and 4B and illustrate the arrangement of one or more magnets that may be used to concentrate and collect a quantity of magnetically responsive beads from a large sample volume. In one embodiment, referring to FIG. 16A, a magnet 1610 may be positioned in proximity to sample dispensing electrode 424*a* within droplet operations region 422 (gap height H1). In particular, magnet 1610 is arranged such that sample dispensing electrodes 424*a* through 424*e* are within the magnetic field thereof. Magnet 1610 may, for example, be a permanent magnet or an electromagnet. The magnetic force of magnet 1610 may be used to concentrate a quantity of magnetically responsive beads (not shown) in a region of sample fluid (not shown) that is closest to magnet 1610. An example of a magnet-based bead concentration and collection protocol is described in reference to FIGS. 5A, 5B, and 5C.

In another embodiment and referring to FIG. 16B, a series of magnets 1610 with increasing magnetic field strength may be positioned in proximity to certain sample dispensing electrodes 424. It should be noted that the magnets may be of the same strength but may be positioned at differing distances from the droplet operation gap such that a gradient of increasing magnetic field strength is established in the gap. In one example, four magnets 1610 of different magnetic field strengths may be used to achieve a progressively increasing magnetic field strength across sample dispensing electrodes 424. For example, a magnet 1610d with a low magnetic field strength (S1) may be positioned in proximity of sample dispensing electrodes 424d and 424e. A magnet 1610c with a greater magnetic field strength (S2) may be positioned in proximity of sample dispensing electrode 424d. A magnet 1610b with a yet greater magnetic field strength (S3) may be positioned in proximity of sample dispensing electrodes 424c and 424b. A magnet 1610a with a still greater magnetic field strength (S4) may be positioned in proximity of sample dispensing electrode 424a. In this example, the increase in the magnetic field strength of magnets 1610 may be described as a gradient wherein S1≥S2≥S3≥S4. The magnetic field gradient is such that magnetically responsive beads are pulled from sample dispensing electrode 424e towards sample dispensing electrode 424a.

In yet another embodiment, a magnet 1610 may be a movable magnet (not shown). In this example, magnet 1610 may be positioned over or under droplet actuator 400 such that magnet 1610 is aligned with and movable along the path of sample dispensing electrodes 424. In one example, a volume of sample fluid, with magnetically responsive beads therein, may be positioned at sample dispensing electrodes 424c and 424e and aligned with magnet 1610. Because of the magnetic force of magnet 1610, the magnetically responsive beads are held at the surface of sample dispensing electrodes 424c and 424d. As magnet 1610 is moved toward sample dispensing electrode 424a, the magnetically responsive beads are pulled toward sample dispensing electrode 424a.

FIG. 17 illustrates a side view of a portion of a droplet actuator 1700 that includes a strong magnet positioned a certain distance away from the bottom surface of the droplet actuator. Typically, a magnet is positioned in close proximity to the bottom substrate of a droplet actuator for attracting a quantity of magnetically responsive beads in a sample. Consequently, for a large sample volume, magnetically responsive beads that are closest to the magnet are strongly attracted to magnet, while beads within the sample that are further away from the magnet exhibit substantially little or no attraction to the magnet. Droplet actuator 1700 of the invention is positioned near a magnet that provides a magnetic field strength that is suitably large such that substantially all magnetically responsive beads in a large sample volume are within the magnetic field of the magnet, albeit the beads may be experiencing different magnetic field strengths because of some amount of magnetic field gradient.

Droplet actuator 1700 may include a bottom substrate 1710 and a top substrate 1712 that are separated by a gap 1714. Droplet actuator 1700 may include a sample dispensing region 1716 (e.g., storage and dispensing) and a droplet operations region 1718 (e.g., transporting, incubation, washing). In one example, sample dispensing region may span about 3 cm in length. The height of gap 1714 at each region may vary. Sample dispensing region 1716 of droplet actuator 1700 may have a certain gap height (H2) that is sufficiently large to facilitate storage of large volume of fluid. Droplet operations region 1718 may have a gap height (H1) which is smaller than H2 that facilitates droplet operations such as rapid transport, mixing, washing, and/or incubation of one or more droplets. One or more sample dispensing electrodes 1720 may be provided within sample dispensing region 1716 on bottom substrate 1710. A volume of sample fluid 1722 may be positioned atop sample dispensing electrodes 1720 within sample dispensing region 1716. Sample fluid 1722 may span the length of sample dispensing region 1716, e.g., about 3 cm. Sample fluid 1722 may, for example, be about a 1 mL sample droplet that includes a quantity of magnetically responsive beads 1724.

A magnet 1726 may be positioned at a certain distance away from and below bottom substrate 1710. Magnet 1726 may, for example, be a strong permanent magnet or a strong electromagnet. The distance between magnet 1726 and sample dispensing electrodes 1720 provides a gradient of magnetic field strength from magnet 1726 across sample dispensing region 1716. Further, magnet 1726 is suitably strong such that substantially all of the volume of sample fluid 1722 is within the magnetic field of magnet 1726. That is, substantially all magnetically responsive beads 1724 in sample fluid 1722 are within the magnetic field of the magnet, albeit the magnetically responsive beads 1724 may be experiencing different magnetic field strengths because of some amount of magnetic field gradient. Magnet 1726 may be positioned such that its magnetic field strength is greater at H1 than at H2. Consequently, a magnetic field gradient is formed such that magnetically responsive beads are attracted from H2 toward H1, which is toward the stronger magnetic field strength of magnet 1726).

7.4 Droplet Transport

FIGS. 18A through 18C illustrate top views of an electrode arrangement 1800 of a portion of a droplet actuator and illustrate a process of transporting a small droplet onto a reservoir electrode. The process shown in FIGS. 18A through 18C is an example of a transporting method that uses droplet "stretching" to prevent fracturing of the droplet into several smaller droplets when entering a reservoir. Fracturing of a droplet during transport into a reservoir may interfere with subsequent processing steps such as mixing and dispensing.

Electrode arrangement 1800 may include a reservoir electrode 1810. An arrangement of droplet operations electrodes 1812 feeds into reservoir electrode 1810. A droplet 1814 may be positioned on a certain droplet operations electrode 1812 for transporting onto reservoir electrode 1810.

An example of a transport process in which a droplet is "stretched" to prevent fracturing of the droplet into several smaller droplets when entering a reservoir may include, but is not limited to, the following steps.

In one step, FIG. 18A shows droplet 1814 positioned on a certain droplet operations electrode 1812 several electrodes (e.g., 3 droplet operations electrodes 1812a, 1812b, and 1812c) away from reservoir electrode 1810.

In another step, FIG. 18B shows droplet 1814 stretched across 3 droplet operations electrodes 1812. Droplet 1814 is slowly stretched across adjacent droplet operations electrodes 1812 by sequentially activating (turning ON) adjacent electrodes. Droplet operations electrodes 1812 may be activated in a sequential manner or in a substantially simultaneous manner, causing droplet 1814 to stretch and extend along all three electrodes.

In another step, FIG. 18C shows droplet 1814 positioned on reservoir electrode 1810. Once droplet 1814 is stretched, droplet operations electrodes 1812 are deactivated (turned OFF) and reservoir electrode 1810 is activated (turning ON), causing droplet 1814 to move into reservoir electrode 1810. Droplet operations electrodes 1812 may be turned OFF in a sequential manner or in a substantially simultaneous manner.

7.5 Sample Containment

Variation in gap height from a sample dispensing region to a droplet operations region may, for example, transition from a large gap height (H2) to a smaller gap height (H1). In one example, a sample dispensing region may have a gap height (H2) of about 5 mm and a droplet operations region may have a gap height (H1) of about 550-600 µm. At larger gap heights of about 5 mm, the height of a sample fluid (e.g., about 1 mL) within the sample dispensing region may be less than the available gap height, e.g., the sample fluid does not exit to the top substrate due to the effect of gravity. Because the sample fluid is not in contact with the top substrate, the sample fluid may flow uncontrolled out of the H2 gap and into the H1 gap (droplet operations region) when the sample dispensing electrodes are activated (turned ON).

FIGS. 19A through 19D illustrate side views of a portion of a droplet actuator 1900 and illustrate methods for containing the sample space of an on-actuator reservoir. The processes shown in FIGS. 19A through 19D are examples of fluid containment methods that prevent uncontrolled flow of a sample fluid from a large gap height (H2) into a smaller gap height (H1) when sample dispensing electrodes within the on-actuator reservoir are activated. In one embodiment, the droplet actuator may include hydrophilic patches for sample fluid retention. In another embodiment, the droplet actuator may include physical structures for sample fluid retention. In yet another embodiment, the ratio of H2:H1 may be increased such that a greater pressure difference between H1 (higher pressure area) and H2 (lower pressure area) is formed.

Droplet actuator 1900 may include a bottom substrate 1910 and a top substrate 1912 that are separated by a gap 1914. Droplet actuator 1900 may include a sample dispensing region 1916 (e.g., storage and dispensing) and a droplet operations region 1918 (e.g., transporting, incubation, washing). The height of gap 1914 at each region may vary. Sample dispensing region 1916 of droplet actuator 1900 may have a certain gap height (H2) that is sufficiently large to facilitate storage of large volume of fluid (e.g., about 1 mL). Droplet operations region 1918 may have a gap height (H1) which is smaller than H2 that facilitates droplet operations such as rapid transport, mixing, washing, and/or incubation of one or more droplets. One or more sample dispensing electrodes 1920 may be provided within sample dispensing region 1916 on bottom substrate 1910. A sample fluid droplet 1922 may be positioned atop sample dispensing electrode 1920 within sample dispensing region 1916. Sample fluid droplet 1922 may, for example, be about a 1 mL, sample droplet.

Figure 19A:
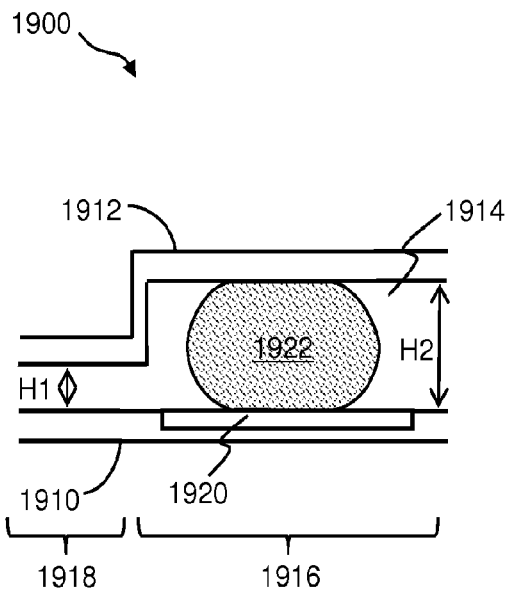

FIG. 19A illustrates a preferred state of sample fluid droplet 1922 within sample dispensing region 1916. In this example, when sample dispensing electrode 1920 is activated (turned ON), sample fluid droplet 1922 is in a rounded shape and extends to and contacts top substrate 1912 within sample dispensing region 1916. Sample fluid droplet 1922 is contained within sample dispensing region 1916.

Figure 19B:
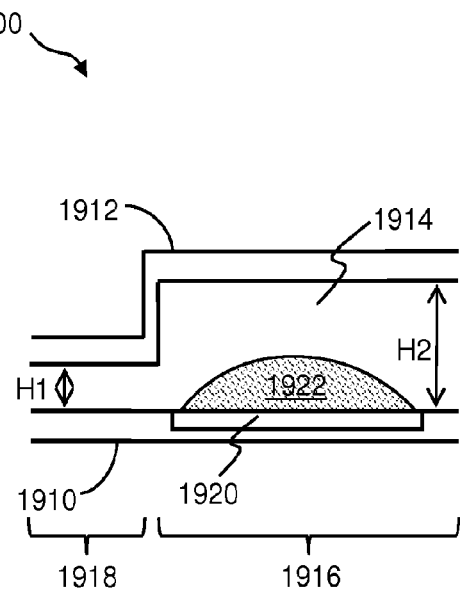

Referring to FIG. 19B, at larger gap heights, e.g., about 5 mm, the height of sample fluid droplet 1922 within the sample dispensing region 1916 is less than the available gap height, e.g., the sample fluid does not extent to top substrate 1912 due to the effect of gravity. Because the sample fluid droplet 1922 is not in contact with top substrate 1912, the sample fluid may flow uncontrolled out of the H2 gap and into the H1 gap (e.g., droplet operations region 1918) when sample dispensing electrode 1920 is activated (turned ON).

Figure 19C:
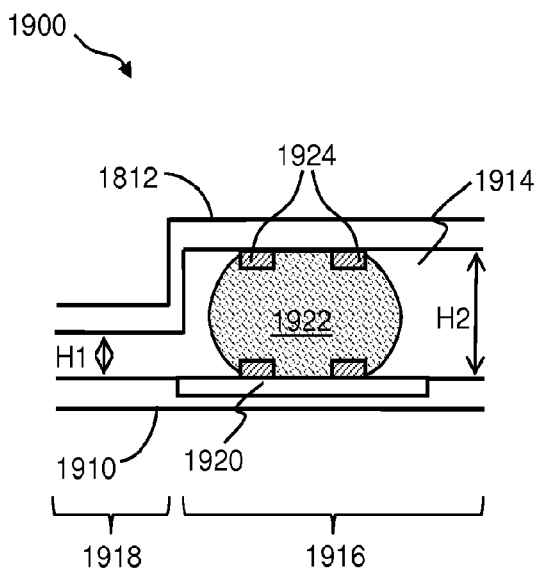

Sample fluid droplet 1924 may be contained within sample dispensing region 1916 by incorporation of chemical and/or physical structures within sample dispensing region 1916. In one embodiment, droplet actuator 1900 may include hydrophilic patches for assisting in sample fluid retention. Referring to FIG. 19C, one or more hydrophilic patches 1924 may be disposed within sample dispensing region 1916 on the surface of top substrate 1912 that is facing gap 1914. Similarly, one or more hydrophilic patches may be disposed on bottom substrate 1910 that is facing gap 1914. Hydrophilic patches 1924 have affinity to aqueous sample fluid droplet 1924 such that sample fluid droplet 1924 is retained in sample dispensing region 1916 when sample dispensing electrode 1920 is activated (turned ON).

Figure 19D:
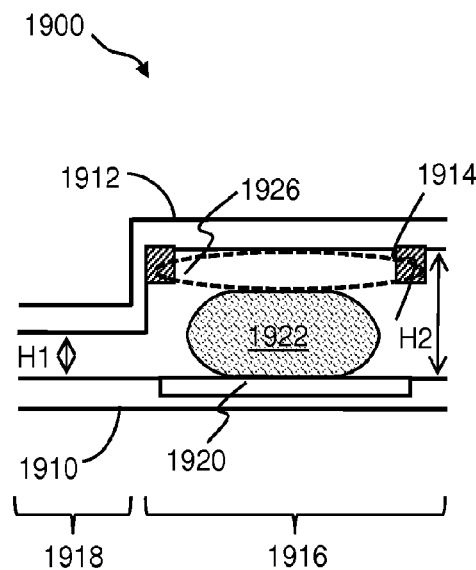

In another embodiment, droplet actuator 1900 may include physical structures for sample fluid retention. Referring to FIG. 19D, a physical structure 1926 may be provided on, for example, the surface of top substrate 1912 that is facing gap 1914. Physical structure 1926 may, for example, be a ring structure that extends from top substrate 1912 to the top surface of sample droplet 1924. Physical structure 1926 is designed to permit sample dispensing, while at the same time hinder uncontrolled flow of sample fluid 1924 from sample dispensing region 1916 (H2) into droplet operations region 1918 (H1). In another example, physical structure 1926 may be provided on the surface of bottom substrate 1910 that is facing gap 1914.

In yet another embodiment, the ratio of H2:H1 may be increased such that a greater pressure difference is between H1 (higher pressure area) and H2 (lower pressure area) is formed. The increase in pressure difference between H1 and H2 provides resistance to fluids flowing from H2 into H1 and facilitates retention of sample fluid 1924 in sample dispensing region 1916 (H2).

7.6 Detection System

The detection system of the invention uses a single excitation beam and a single detection beam to collect multiple (e.g. four) different fluorescent signals at a single detection spot on a droplet actuator. By using an arrangement of light-emitting diodes (LEDs) that includes excitation lenses, filters, and mirrors, multiple (e.g. four) different excitation wavelengths are multiplexed in a single excitation beam. Similarly, by using an arrangement of detectors (e.g. photo diodes) that includes mirrors, filters and detection lenses, a single optical beam is used for detection of the corresponding emission signals.

FIGS. 20A and 20B illustrate perspective views of two example embodiments of a detection system 2000 for detection of multiple (e.g. four) different fluorophores at a single detection spot. In one example, FIG. 20A shows an embodiment of detection system 2000 in which four LEDs and four detectors are arranged in a parallel configuration near the droplet actuator. In another example, FIG. 20B shows an embodiment of detection system 2000 in which the four LEDs and four detectors are arranged in a "V" configuration near the droplet actuator.

Detection system 2000 may include multiple excitation LEDs 2010 that are aligned with multiple excitation lenses 2012, multiple excitation filters 2014, and multiple mirrors 2016, respectively. By way of example, detection system 2000 may include four LEDs 2010a through 2010d that are aligned with four excitation lenses 2012a through 2012d, four excitation filters 2014a through 2014d, and four mirrors 2016a through 2016d, respectively. Each excitation lens 2012 is used to focus light emitted from its corresponding LED 2010 onto the corresponding excitation filter 2014. Each excitation filter 2014 is used to select a certain wavelength of light emitted from its corresponding LED 2010 that may be used for excitation of a certain fluorophore. Each mirror 2016 is used to direct the filtered light (e.g., light of a certain wavelength) to a corresponding second directing mirror 2018 that is positioned in proximity of a corresponding excitation focusing lens 2020. Each directing mirror 2018 and corresponding focusing lens 2020 is used to multiplex the different wavelengths of light (e.g., four different wavelengths of light) into a single excitation beam.

Detection system 2000 may also include multiple detectors 2022 that are aligned with multiple detection lenses 2024, multiple detection filters 2026, and multiple selective dichroic filters 2028, respectively. By way of example, detection system 2000 may include four detectors 2022a through 2022d that are aligned with four detection lenses 2024a through 2024d, four detection filters 2026a through 2026d, and four dichroic filters 2028a through 2028d, respectively. Each dichroic filter 2028 is used to select a certain wavelength of light corresponding to the emission wavelength of a certain fluorophore. A focusing lens 2030 and a directing mirror 2032 are used to multiplex different wavelengths of light emitted from one or more fluorophores (e.g., four different fluorophores) into a single detection beam.

In operation, detection system 2000 (in either the parallel configuration of FIG. 20A or the "V" configuration of FIG. 20B) is positioned in an instrument (not shown) that is a holding a droplet actuator, such as a droplet actuator 2034. Detection system 2000 is positioned such that a single excitation beam of light and a single detection beam are directed to a detection spot (not shown) on droplet actuator 2034.

In one embodiment and referring to FIG. 20A, the parallel configuration of LEDs and detectors of detection system 2000 is offset from droplet actuator 2034. In this example, the excitation (incident) beam and the detection (emission) beam are aligned in parallel. In this configuration, the fluorimeter may, for example, be positioned off the back of the droplet actuator.

In another embodiment and referring to FIG. 20B, the "V" configuration of LEDs and detectors of detection system 2000 is positioned above droplet actuator 2034. In this configuration, the fluorimeter may, for example, be positioned above droplet actuator 2034.

7.7 Thermal Control

The invention provides methods for controlling heat flow and minimizing thermal losses in one or more temperature control zones on a droplet actuator. In particular, the methods of the invention use alternative configurations of the bottom substrate materials, e.g., printed circuit board (PCB), to control the flow of heat around the PCB. Because the flow of heat around the PCB is controlled, different temperature control zones may be defined and used to support multiple droplets undergoing different reactions at the same time. Careful configuration of substrate materials allows minimal use of input heat to maintain temperature zones, and droplets in those zones, at desired temperatures.

FIG. 21 illustrates a top view of an example of a portion of a droplet actuator 2100 and illustrates methods for controlling the flow of heat in certain regions (temperature control zones) of a droplet actuator. Droplet actuator 2100 may include a bottom substrate 2110. Bottom substrate 2110 may, for example, be a PCB or other polymeric substrate that includes a dielectric layer 2112. For a PCB substrate, dielectric layer 2112 may, for example, be an FR4 layer. Bottom substrate 2110 may include an arrangement of droplet operations electrodes 2114 (e.g., electrowetting electrodes). Droplet operations are conducted atop droplet operations electrodes 2114 on a droplet operations surface. Droplet actuator 2100 may include one or more temperature control zones 2116, e.g., temperature control zones 2116a and 2116b, for performing certain process steps. One or more heater elements 2118, e.g., two heater elements 2118a and 2118b, may be provided in proximity to bottom substrate 2110 and aligned with certain droplet operations electrodes 2114. Heater elements 2118 may be used to heat the temperature of filler fluid that is in the gap (not shown) of droplet actuator 2100 and that is flowing through temperature control zones 2116.

In one embodiment, the geometry of conductive materials, such as copper, on bottom substrate 2110 (e.g. the PCB) may be used to control the flow of heat in temperature control zones 2116, e.g., to maintain temperature uniformity or to increase time to desired temperature in bottom substrate 2110 at temperature control zones 2116. In one example, a copper heat spreader 2120 (copper heat spreading pad) may be provided on the same PCB layer as droplet operations electrodes 2114. In this example, heat spreader 2120 may be positioned adjacent to certain droplet operations electrodes 2114. In another example, a copper heat spreader 2122 may be provided on a different PCB layer as droplet operations electrodes 2114 (e.g., backside layer or layer adjacent to electrode layer). Heat spreaders 2120 and 2122 may be used to maintain different isothermal regions on droplet actuator 2100 such that the temperature gradient ($\Delta T$) across that region of the PCB is small. Because copper heat spreaders are used, smaller heater elements 2118 may be used and thereby minimize the amount of input heat required to maintain a droplet at a certain reaction temperature.

In another example, the amount of copper on bottom substrate 2110 that surrounds temperature control zones 2116 may be minimized (not shown) to reduce conductive loss of heat from the thermal control zone. Because excess copper (or other conductive material) is reduced and conductive heat loss is minimized, additional power input is not required to compensate for potential heat loss.

In yet another example, the area covered by bottom-side traces (not shown) on bottom substrate 2110 and within temperature control zones 2116 may be maximized. For example the area of the trace used to conduct an electrowetting voltage to certain droplet operations electrodes 2114 within temperature control zone 2116 may be increased. Because the area of the trace is increased, more heat may be absorbed from heater element 2118.

In yet another example, certain droplet operations electrodes 2114 that are heated to the same temperature may be co-localized in the same temperature control zone 2116. The distance between co-localized droplet operations electrodes 2114 may be minimized such that thermal loss is substantially reduced and heating accuracy is maintained. Droplet operations electrodes 2114 may be tied using metal filled or plated vias to the same bottom-side copper heat spreading pad. The copper heat spreading pad may, for example, be sized to cover about the same area as the co-localized droplet operations electrodes. Alternatively, equal area may be provided for all bottom-side traces for each droplet operations electrode in the same temperature control zone, with traces generally sized to substantially cover the area of the copper heat spreading pad. Alternatively, equal area may be provided for all bottom-side traces for each droplet operations electrode in the same temperature control zone, with traces generally sized to serve the function of a heat spreading pad.

In yet another example, the amount of copper in vias that are used to couple droplet operations electrodes 2114 within temperature control 2116 to bottom-side heat spreading pads (e.g., heat spreader 2122) may be maximized. For example, the amount of copper used may be maximized by using the larger sized vias and/or by increasing the number of vias used. Via plating thickness may also be specified to maximize the amount of copper connecting droplet operations electrodes 2114 to bottom-side heat spreading pads.

another embodiment, the geometry of the dielectric material (e.g., FR4) on bottom substrate 2110 may be used to control (reduce) the flow of heat around temperature control zones 2116. In one example, the thickness of dielectric layer 2112 may be minimized, e.g., from less than about 31 mils to about 1 mil. Mechanical means may be used to provide physical support to areas on the PCB with substantially reduced dielectric material. Because heat is applied through dielectric layer 2112, minimizing the thickness of dielectric layer 2112 minimizes the thermal resistance between heater 2118 and temperature control zone 2116, minimizes the heat capacity of the PCB, and maximizes the in-plane thermal resistance to other parts of the PCB. Reduction in the thickness of dielectric layer 2112 maximizes the impact of heat spreaders 2120 and 2122 which have the dominant thermal conductivity.

In another example, one or more cutouts in dielectric layer 2112, e.g., cutouts 2124a through 2124c, may be used to further reduce thermal conduction around temperature control zone 2116. Materials with low thermal conductivity (e.g., air, plastic) may be used to fill or reinforce cutouts 2124.

FIGS. 22A, 22B, and 22C illustrate top views of an example of a portion of a droplet actuator 2200 and illustrate methods for co-locating temperature control zones and associated heat spreaders on a droplet actuator. Droplet actuator 2200 may include a bottom substrate 2210. Bottom substrate 2210 may, for example, be a PCB. Bottom substrate 2210 may include an arrangement of droplet operations electrodes 2212 (e.g., electrowetting electrodes). Droplet operations are conducted atop droplet operations electrodes 2212 on a droplet operations surface. Droplet actuator 2200 may include one or more temperature control zones 2214, e.g., temperature control zones 2214a through 2214e, to be used during certain process steps. Bottom substrate 2210 may include one or more heat spreaders (copper heat spreading pads) 2216, e.g., five heat spreaders 2216a through 2216e, for controlling the flow of heat within associated temperature control zones 2214. In one example, heat spreaders 2216 may be provided on a different PCB layer as droplet operations electrodes 2212 (e.g., backside layer or layer adjacent to electrode layer). Heat spreaders 2216 may be used to heat temperature control zones 2214 to the same temperature or to different temperatures. Temperature control zones 2214 that are heated to the same temperature may be thermally coupled. In one example, three different temperature control zones, such as three temperature control zones used for PCR assays, may be used. In this example, heat spreader 2216a may be used to heat a temperature control zone 2214a to a temperature T1 that is suitable for performing certain process steps. Heat spreaders 2216b and 2216d may be used to heat temperature control zones 2214b and 2214d to a second temperature T2 that is suitable for performing other process steps. Heat spreaders 2216c and 2216e may be used to heat temperature control zones 2214c and 2214e to a third temperature T3 that is suitable for performing yet other process steps. One or more reaction droplets (not shown) may be transported on droplet operations electrodes 2212 using droplet operations into and out of temperature control zones 2214 (e.g., cycling between temperatures T1, T2, and T3).

FIG. 22B shows one example of implementing the co-located temperature control zones and associated heat spreaders that are described in FIG. 22A. In this example, one or more heater elements 2218 may be used to provide heat to heat spreaders 2216. For example, five heater elements 2218a through 2218e may be patterned directly underneath heat spreaders 2216 on bottom substrate 2210. Heater elements 2218a through 2218e may, for example, be resistive heaters. Bottom substrate 2210 may also include one or more thermometers 2220, e.g., thermometers 2220a through 2220e. Thermometers 2220 may, for example, be used as temperature sensors used to monitor and regulate the temperature of heat spreaders 2216. Thermometers 2220 could, for example, be selected from thermistors, metallic resistive temperature detectors, thermocouples and the like.

FIG. 22C shows another example of implementing the co-located temperature control zones and associated heat spreaders that are described in FIG. 22A. In this example, heater elements 2218 may be thermoelectric heat pumps (e.g., Peltier device) that are used to control the flow of heat between adjacent heat spreaders 2216 and one or more ambient heatsinks 2222, e.g., heatsinks 2222a and 2222b. In this example, eight heater elements 2218, e.g., heater elements 2218a through 2218h may be used to control the flow of heat between adjacent heat spreaders 2216 and heatsinks 2222. Heater elements 2218 may, for example, be thin film Peltier devices, such as the Peltier devices commercially available from Nextreme.

FIG. 23A illustrates a top view of an example of a portion of a droplet actuator 2300 and illustrate a method for manipulating or controlling a temperature gradient along a path of droplet operations electrodes. In this example, controlled thermal resistance is provided by the geometry of a copper heat spreading pad (heat spreader) relative to the surrounding dielectric material (e.g., FR4 with high thermal resistance). The copper heat spreading pad is used to form a temperature gradient along a path of droplet operations electrodes within a temperature control zone on a droplet actuator. Any suitable heat source may be applied to the heat spreading pad.

Droplet actuator 2300 may include a bottom substrate 2310. Bottom substrate 2310 may, for example, be a PCB that includes a dielectric layer such as FR4. Bottom substrate 2310 may include an arrangement of droplet operations electrodes 2312 (e.g., electrowetting electrodes). Droplet operations are conducted atop droplet operations electrodes 2312 on a droplet operations surface. Bottom substrate 2310 may also include a heat spreader 2314 for controlling the flow of heat within a certain temperature control region (not shown).

In one example, heat spreader 2314 is a copper heat spreading pad. Further, heat spreader 2314 may be provided on a different PCB layer as droplet operations electrodes 2312 (e.g., backside layer or layer adjacent to electrode layer). In another example, heat spreader 2314 may be provided on the same PCB layer as droplet operations electrodes 2312. Heat spreader 2314 may be formed in a V-shape such that a temperature gradient is formed along a path of droplet operations electrodes 2312. Heat spreader 2314 may, for example, be heated using a single heating element (not shown). In some embodiments, the heat spreading pad or pads have a shape and/or arrangement selected to produce a substantially linear gradient along a path of droplet operations electrodes. In some embodiments, heat spreaders are shaped in the form of a "U" and arranged such that a temperature gradient is formed along the path of droplet operations electrodes, wherein one or more heater elements is coupled to each "U" shaped heat spreader.

In one example, a single heating element 2313 may be positioned at the narrow end of the V-shaped heat spreader 2314. The temperature of heat spreader 2314 is substantially the same along the V-shaped geometry of heat spreader 2314.

As the distance from droplet operations electrodes 2312 to heat spreader 2314 increases, the thermal resistance provided by the dielectric material (e.g., FR4) on bottom substrate 2310 increases and a predictable and linear temperature gradient may be formed. In one example, the temperature gradient along droplet operations 2312 may change in 10-degree increments at each droplet operations electrode 2312. For example, the temperature gradient may change from about 100 DC at the narrow end of the V-shaped heat spreader 2314 to about 60° C. at the wide end of the V-shaped heat spreader 2314.

FIG. 23B illustrates a top view of an example of a portion of a droplet actuator 2350 that includes an arrangement of multiple heat spreaders 2314 that are described in FIG. 23A. In this example, an arrangement of one or more heat spreaders 2314 and corresponding droplet operations electrodes 2312 are aligned in tandem on droplet actuator 2350.

FIG. 24 illustrates a top view of an example of a portion of a droplet actuator 2400 and illustrates another method for forming a temperature gradient along a path of droplet operations electrodes. In this example, the dimensions of a copper heat spreading pad (heat spreader) may be used to control the thermal resistance along a path of droplet operations electrodes and establish a temperature gradient. By controlling the width of the copper trace, e.g., from about 1 mm to about 0.5 mm wide, the amount of heat loss may be controlled along the path of droplet operations electrodes.

Droplet actuator 2400 may include a bottom substrate 2410. Bottom substrate 2410 may, for example, be a PCB. Bottom substrate 2410 may include an arrangement of droplet operations electrodes 2412 (e.g., electrowetting electrodes). Droplet operations are conducted atop droplet operations electrodes 2412 on a droplet operations surface. A heat spreader 2414 may be provided on bottom substrate 2410 for controlling the flow of heat within a certain temperature control region (not shown). In one example, heat spreader 2414 is a copper heat spreading pad. Heat spreader 2414 may be a V-shaped copper trace formed of segments 2416, 2418, and 2420. In one example, segment 2420 of the V-shaped heat spreader 2414 may, for example, be from about 1 mm to about 0.5 mm wide. Heat spreader 2414 may, for example, be heated using a single heating element 2422 positioned in proximity to segment 2418 of the V-shaped heat spreader 2414.

The arrangement of heat spreader 2414 is such that a temperature gradient is formed along a path of droplet operations electrodes 2412. In one example, heating element 2422 may be used to heat segment 2418 to a temperature of about 100° C. As segment 2418 is heated, heat is conducted along segment 2420 to segment 2416 and a temperature gradient is formed between segment 2418 and 2416. The temperature gradient may, for example, change from about 100° C. at segment 2418 to about 50° C. at segment 2416 of heat spreader 2414.

Heat from segment 2418 may also be conducted by droplet operations electrodes 2412. Thermal resistance in this heat conducting pathway may be dominated by the gaps between each droplet operations electrode 2412, where heat must flow through the dielectric material, e.g., FR4, with high thermal resistance. In one example, the gaps between each droplet operations electrode 2412 may be about 0.127 mm.

In another embodiment, one or more heat sinks (not shown) along the arrangement of droplet operations electrodes 2412 may be used to control the flow of heat on droplet actuator 2400.

7.8 Heat Transfer

The invention provides devices and methods for generating heat off-actuator and transferring the heat to designated temperature control zones on a droplet actuator. In one embodiment, the invention provides devices and methods for generating resistive heat off-actuator and transferring the heat to certain temperature control zones on a droplet actuator. In another embodiment, the invention provides devices and methods for transferring radiative heat to certain temperature control zones on a droplet actuator. Alternatively, heat may be generated at a surface of the droplet operations substrate using surface mounted resistors which are mounted to the substrate itself.

7.8.1 Resistive Heat Transfer

In one example, a resistive heater mounted to a spring-loaded bulk metallic conductor (e.g., aluminum cylinder) may be used to generate and transfer heat to a designated temperature control zone on a droplet actuator. FIG. 25 illustrates a perspective view of a resistive heating device 2500 that includes resistive heaters mounted to spring-loaded metallic conductors. Heating device 2500 may include a mechanical support or body 2510 that includes one or more openings 2512 of sufficient size and shape (e.g. cylindrical shape) to accommodate one or more heater assemblies 2514, respectively. Mechanical support or body 2510 may, for example, be formed of a plastic material. In one embodiment, three openings 2512 are provided in mechanical support or body 2510 to accommodate three heater assemblies 2514a, 2514b, and 2514c. Each heater assembly 2514 may include a resistive heater 2516 that is attached to a bulk metallic conductor 2518, Metallic conductor 2518 may, for example, be an aluminum cylinder. Metallic conductor 2518 with resistive heater 2516 attached thereto may be mounted on a spring 2520 positioned in opening 2512. In operation, spring 2520 is used to hold heater assembly 2514 by spring force against the outside surface of the bottom substrate of a droplet actuator (not shown). Heat from resistive heater 2516 is transferred through metallic conductor 2518 to a temperature control zone on a droplet actuator (not shown).

In another example, a heater device that includes a flex heater with a copper heat spreader may be used to generate and control heat transfer to a designated temperature control zone on a droplet actuator. Examples of flexible heater circuits include polyimide heaters, such as KAPTON® polyimide heaters; silicone rubber heaters (foil); silicone rubber heaters (wire-wound); thermal-clear transparent heaters; mica heaters; all-polyimide heaters; and PTFE (TEFLON™) heaters; all available from Minco, Inc., Minneapolis, Minn.

In this example, an elastomeric pad (e.g., a neoprene pad or a rubber pad) coupled with a rigid support (e.g., delrin, aluminum) may be used to position and contact the flex heater circuit to the bottom substrate (e.g. the PCB) of a droplet actuator.

FIG. 26 illustrate a perspective view of another example of a heating device 2600. In this example, heating device 2600 includes one or more flex heater assemblies. Heater device 2600 may include a rigid support or body 2610 that has one or more openings or clearance regions for accepting one or more flex heater assemblies 2612 that are mounted on respective elastomeric pads 2618 The elastomeric pads 2618 are fitted into the respective openings or clearance regions of rigid support or body 2610. Rigid support or body 2610 may, for example, be formed of a rigid material, such as delrin, aluminum, and plastic. Elastomeric pads 2618 may, for example, be formed of neoprene or rubber.

In one embodiment, three openings or clearance regions are provided in rigid support or body 2610 to accept three flex heater assemblies 2612a, 2612b, and 2612c and their respective elastomeric pads 2618a, 2618b, and 2618c. Each flex heater assembly 2612 may include a flexible lead 2614 for making an electrical connection to a heater circuit 2616. In one example, each heater circuit 2616 may be a flex heater circuit with an integrated copper heat spreader. Because flex heater circuits may be custom made, the polyimide dielectric layer may be patterned with other highly resistive metallic materials such as constantan, stainless steel, or inconel. By using highly resistive materials, a large amount of heat may be generated in a small area of the droplet actuator. The elastomeric pads 2618 are used to support the heater circuit 2616-end of flex heater assemblies 2612.

The positions of flex heater assemblies 2612 in rigid support or body 2610 correspond to the positions of heating zones of a droplet actuator (not shown) for which heating device 2600 is designed. In operation, the heater circuits 2616 of flex heater assemblies 2612 of heating device 2600 are pressed against, for example, the bottom substrate of the droplet actuator. In this way, heat from each heater circuit 2616 is transferred directly to a corresponding temperature control zone of the droplet actuator. Portions of rigid support body may also be used to support other bodies used for integrated functions, such as manipulation of magnetic beads in the droplet operations gap.

In yet another example, resistive heat transfer may be accomplished through spring pins connecting an electrowetting effector board and droplet actuator. The electrowetting effector board includes an array of small spring pins that make electrical contact with the microfluidic chip. The electrowetting effector board communicates the signals that control droplet movement from the instrument to the droplet actuator. An example of an electrowetting effector board is described below in FIGS. 27A and 27B.

FIGS. 27A and 27B illustrate side views of an example of a portion of an electrowetting effector board 2700 configured for generation of resistive heat and illustrate the alignment of the effector board with a droplet actuator for resistive heat transfer. As shown in FIG. 27A, electrowetting effector board 2710 may, for example, be a PCB that includes a copper trace 2712 and a spring pin 2714. A heating element 2716 may be electrically coupled to copper trace 2712. Heating element 2716 may, for example, be a Kapton flex heater or a typical foil or thin film resistor.

Referring to FIG. 27B, electrowetting effector board 2700 may be aligned with a droplet actuator 2718. Droplet actuator 2718 may, for example, include a PCB that includes a copper trace 2720. Copper trace 2720 may, for example, be positioned with a certain temperature control zone of droplet actuator 2718. The alignment of electrowetting effector board 2700 and droplet actuator 2718 is such that spring pin 2714 contacts copper trace 2720. As spring pin 2714 makes contact with copper trace 2720, heat generated from heating element 2716 is transferred to copper trace 2720 of droplet actuator 2718.

In another example, a different set of spring pins may be used for resistive heat transfer. In this example, effector board 2700 may be a separate heater board.

7.8.2 Radiative Heat Transfer

The invention provides devices and methods for transferring radiative heat to certain temperature control zones on a droplet actuator. Because radiative heat is used, contact between a heat source and the droplet actuator is not required.

FIG. 28 illustrates a side view of an example of a portion of a droplet actuator 2800 that is configured for radiative heat transfer to a temperature control zone on a droplet actuator. Droplet actuator 2800 may include a bottom substrate 2810. Bottom substrate 2810 may, for example, be a PCB that includes a dielectric layer 2812 (e.g., FR4). At least one droplet operations electrode 2814 (e.g., electrowetting electrode) may be patterned atop dielectric layer 2812. A heat conductor 2816 may be patterned on the backside of dielectric layer 2812 and opposite from droplet operations electrode 2814. Heat conductor 2816 may, for example, be a copper heat conductor. Droplet operations electrode 2814 and heat conductor 2816 are thermally connected by a via 2818, which may be a copper via. Attached (bonded) to heat conductor 2816 is a blackbody 2820. Blackbody 2820 may, for example, be an infrared (IR) absorbing blackbody. An infrared heat source 2822 may be positioned in proximity (e.g., about 2 mm from) blackbody 2820. Heat source 2822 may, for example, be a laser diode or an IR LED.

In operation, infrared radiation from heat source 2822 is absorbed by blackbody 2820 and transferred as heat through heat conductor 2816 and via 2818 to droplet operations electrode 2814. As with all other embodiments of the invention, thermometer (not shown) may be attached (e.g., taped using tape) to conductor 2816 and used to monitor temperature.

7.9 Temperature Control by Droplet Positioning

The invention provides method for controlling the temperature of a droplet by transporting the droplet from one temperature region to another temperature control region (position dithering) on a droplet actuator. By repeatedly transporting a droplet between temperature regions (e.g., two temperature regions), a droplet temperature may be achieved that is between the temperatures of the two temperature regions.

FIG. 29A illustrates an example of a portion of a droplet actuator 2900 for controlling the temperature of a droplet by position dithering. Droplet actuator 2900 may include a bottom substrate 2910. Bottom substrate 2910 may, for example, be a PCB. Bottom substrate 2910 may include an arrangement of droplet operations electrodes 2912 (e.g., electrowetting electrodes). Droplet operations are conducted atop droplet operations electrodes 2912 on a droplet operations surface. Droplet actuator 2900 may include one or more temperature regions 2914, e.g., two temperature regions 2914a and 2914b. Temperature regions 2914a and 2914b may be separated spatially to achieve a thermal gradient between the two zones. The temperature of a droplet may be controlled and maintained by positioning the droplet at a certain location along the thermal gradient between the two temperature regions 2914a and 2914b. Bottom substrate 2910 may include one or more heat spreaders (copper heat spreading pads) 2916, e.g., heat spreaders 2916a and 2916b, for controlling the flow of heat within associated temperature regions 2914a and 2914b.

In one example, temperature region 2914a may be heated to a temperature of about 100° C. Temperature region 2914b may be heated to a temperature of about 60° C. Because of the thermal gradient between temperature regions 2914a and 2914b, a certain droplet operations electrode 2912 located therebetween and along the thermal gradient may be at an intermediate temperature relative to temperature regions 2914a and 2914b. FIGS. 29B and 29C below are examples of schematic diagrams related to the thermal control of droplet actuator 2900.

FIG. 29B illustrates a schematic diagram of an example of a thermal circuit 2950 for droplet actuator 2900 of FIG. 29A that is configured for position dithering. Thermal circuit 2950 is an example of a circuit representing the thermal gradient between, for example, the two temperature regions 2914a and 2914b. For example, $T_{HOT}$ may be 100° C., which is the temperature at temperature region 2914a, and $T_{COLD}$ may be 60° C., which is the temperature at temperature region 2914b.

FIG. 29C illustrates a schematic view of an example of an electrical equivalent circuit 2970 for position dithering used for droplet temperature control on droplet actuator 2900 of FIG. 29A. Electrical equivalent circuit 2970 represents position dithering as a means of droplet temperature control. In one example, $C_{COPPER}$=0.15 $C_{DROPLET}$ to 0.5 $C_{DROPLET}$, where the larger number may account for other copper connected to the droplet operations electrode through, for example, a via. The following observations may be made: A sizable voltage can be developed at $V_1$ $R_{AMBIENT}$ is relatively high or if a large current (heat flux) is pushed. $R_{AMBIENT}$ is the overall resistance to electrical ground. $R_{POLYIMIDE}$ will typically keep $V_1$ from ever reaching $V_{COLD}$ (or $V_{HOT}$ when switched to that path). There will be some loss across the dielectric layer. The $C_{COPPER}$ capacitors typically charge about 2 times to about 6.5 times faster than the CDROPLET capacitor. In order to prevent $V_1$ from experiencing temperature excursions near $V_{HOT}$ and $V_{COLD}$ (which may be important for PCR and other thermal control applications), the switching speed of the droplet between two positions may need to be significantly faster then the $C_{DROPLET}$ time constant. Otherwise, the temperature excursions need to be controlled by setting $V_{HOT}$ and $V_{COLD}$.

7.10 Systems

Referring to FIGS. 1 through 30, it will be appreciated that various aspects of the invention may be embodied as a method, system, or computer program product. Aspects of the invention may take the form of hardware embodiments, software embodiments (including firmware, resident software, micro-code, etc.), or embodiments combining software and hardware aspects that may all generally be referred to herein as a "circuit," "module" or "system." Furthermore, the methods of the invention may take the form of a computer program product on a computer-usable storage medium having computer-usable program code embodied in the medium.

Any suitable computer useable medium may be utilized for software aspects of the invention. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include some or all of the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission medium such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Computer program code for carrying out operations of the invention may be written in an object oriented programming language such as Java, Smalltalk, C++ or the like. However, the computer program code for carrying out operations of the invention may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the Internet using an Internet Service Provider).

Certain aspects of invention are described with reference to various methods and method steps. It will be understood that each method step can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the methods.

The computer program instructions may also be stored in a computer-readable memory that can direct a computer or other programmable data processing apparatus to function in a particular manner, such that the instructions stored in the computer-readable memory produce an article of manufacture including instruction means which implement various aspects of the method steps.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing various functions/acts specified in the methods of the invention.

8 CONCLUDING REMARKS

The foregoing detailed description of embodiments refers to the accompanying drawings, which illustrate specific embodiments of the invention. Other embodiments having different structures and operations do not depart from the scope of the invention. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the invention may be changed without departing from the scope of the invention. Furthermore, the foregoing description is for the purpose of illustration only, and not for the purpose of limitation.

I claim:

1. A droplet actuator device comprising:
    a. a bottom substrate and a top substrate separated from each other to form a gap therebetween;
    b. an arrangement of droplet operations electrodes on one of or both of the bottom and/or top substrates configured for conducting droplet operations thereon; and
    c. one or more heat-spreader-expanded temperature control zones in the gap, wherein each of the one or more heat-expanded temperature zones is established by at least:

(i) one or more heater elements in proximity to and aligned with one or more of the droplet operations electrodes in the arrangement of droplet operations electrodes in a manner which permits establishment of temperature control in the gap in the vicinity of the one or more droplet operations electrodes; and (ii) a heat spreader comprising a metal layer structure included with one of or both of the bottom and/or top substrates and distinct from the droplet operations electrodes, wherein the heat spreader is arranged to spread heat generated from the one or more heater elements along a droplet operations electrode path comprising the one or more droplet operations electrodes, and wherein the heat spreader is distinct from the one or more heater elements and is configured to spread heat and maintain a more uniform temperature gradient within the one or more heat-spreader-expanded temperature control zones relative to a corresponding droplet actuator device lacking the heat spreader.

2. The droplet actuator device of claim 1, wherein the bottom substrate comprises a PCB.

3. The droplet actuator device of claim 2, wherein the PCB comprises a dielectric layer.

4. The droplet actuator device of claim 1, wherein the arrangement of droplet operations electrodes comprise electrowetting electrodes.

5. The droplet actuator device of claim 2, wherein the arrangement of droplet operations electrodes are arranged on the PCB, and the heat spreader and the arrangement of droplet operations electrodes are provided on a same layer on the PCB.

6. The droplet actuator device of claim 1, wherein the heat spreader is copper.

7. The droplet actuator device of claim 5, wherein the heat spreader is positioned adjacent to the one or more droplet operations electrodes.

8. The droplet actuator device of claim 2, wherein the arrangement of droplet operations electrodes are arranged in a layer on the PCB, and the heat spreader is provided on a different layer on the PCB than the arrangement of droplet operations electrodes.

9. The droplet actuator device of claim 8, wherein the heat spreader is provided on a layer on a backside of the PCB that is opposite to the layer of the arrangement of droplet operations electrodes.

10. The droplet actuator device of claim 8, wherein the heat spreader is provided on a layer on the PCB adjacent to the arrangement of droplet operations electrodes arranged on the PCB.

11. The droplet actuator device of claim 1, comprising at least two heat-spreader-expanded temperature control zones, wherein the heat spreaders are configured to heat the at least two heat-spreader-expanded temperature control zones to a same or different temperatures.

12. The droplet actuator device of claim 11, wherein the at least two heat-spreader-expanded temperature control zones heated to the same temperature are thermally coupled.

13. The droplet actuator device of claim 1, wherein the one or more heater elements provide heat to the heat spreader.

14. The droplet actuator device of claim 8, wherein the one or more heater elements are positioned directly underneath the heat spreader.

15. The droplet actuator device of claim 1, wherein one or more of the one or more heater elements comprises a resistive heater.

16. The droplet actuator device of claim 1, wherein the one or more heater elements comprise thermoelectric heat pumps.

17. The droplet actuator device of claim 1, further comprising thermistors to monitor and regulate the temperature of the heat spreader.

18. The droplet actuator device of claim 1, wherein the heat spreader is shaped to form a temperature gradient along a path of the one or more droplet operations electrodes.

19. The droplet actuator device of claim 18, wherein the heat spreader is shaped in the form of a "V" such that a substantially linear temperature gradient is formed along the path of the one or more droplet operations electrodes, wherein one of the one or more heater elements is positioned at the narrow end of the "V" shaped heat spreader.

20. The droplet actuator device of claim 18, wherein the heat spreader is shaped in the form of a "U" and arranged such that a temperature gradient is formed along the path of the one or more droplet operations electrodes, wherein one of the one or more heater elements is coupled to the "U" shaped heat spreader.

21. The droplet actuator device of claim 1, wherein the gap comprises oil.

22. The droplet actuator device of claim 1, wherein the gap comprises silicone oil.

* * * * *